(12) United States Patent
Shenoy et al.

(10) Patent No.: US 7,615,610 B2
(45) Date of Patent: Nov. 10, 2009

(54) MODIFIED TRAFFICKING PATTERNS FOR ARRESTIN AND G-PROTEIN-COUPLED RECEPTORS VIA ARRESTIN-UBIQUITIN CHIMERA

(75) Inventors: Sudha Shenoy, Durham, NC (US); Robert J. Lefkowitz, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 10/543,122

(22) PCT Filed: Jan. 26, 2004

(86) PCT No.: PCT/US2004/002029

§ 371 (c)(1),
(2), (4) Date: Apr. 20, 2006

(87) PCT Pub. No.: WO2004/067716

PCT Pub. Date: Aug. 12, 2004

(65) Prior Publication Data

US 2006/0263828 A1    Nov. 23, 2006

Related U.S. Application Data

(60) Provisional application No. 60/442,403, filed on Jan. 24, 2003.

(51) Int. Cl.
*C07K 19/00* (2006.01)
*C07K 14/47* (2006.01)
*C12N 15/11* (2006.01)
*G01N 33/566* (2006.01)

(52) U.S. Cl. ............... 530/350; 536/23.4; 435/7.1

(58) Field of Classification Search .............. None
See application file for complete search history.

(56) References Cited

U.S. PATENT DOCUMENTS

| | | |
|---|---|---|
| 3,654,090 A | 4/1972 | Schuurs |
| 3,850,752 A | 11/1974 | Schuurs et al. |
| 4,016,043 A | 4/1977 | Schuurs et al. |
| 4,341,761 A | 7/1982 | Ganfield et al. |
| RE31,006 E | 8/1982 | Schuurs et al. |
| 4,399,121 A | 8/1983 | Albarella et al. |
| 4,427,783 A | 1/1984 | Newman et al. |
| 4,444,887 A | 4/1984 | Hoffmann |
| 4,451,570 A | 5/1984 | Royston et al. |
| 4,466,917 A | 8/1984 | Nussenzweig et al. |
| 4,472,500 A | 9/1984 | Milstein et al. |
| 4,491,632 A | 1/1985 | Wands et al. |

(Continued)

OTHER PUBLICATIONS

Wells (1990) Biochemistry 29(37): 8509-8517.*

(Continued)

*Primary Examiner*—Bridget E Bunner
*Assistant Examiner*—Zachary C Howard
(74) *Attorney, Agent, or Firm*—Gargi Talukder; David J. Brezner; Morgan Lewis & Bockius LLP

(57) ABSTRACT

The present invention relates to a modified arrestin which includes an arrestin molecule and a ubiquitin molecule. This modified arrestin has an increased affinity for a GPCR, and traffics with the GPCR into endosomes. The present invention further relates to a method of screening compounds and sample solutions for a GPCR agonist, antagonist, inverse agonist, or desensitization active compound. The modified arrestin is useful in the methods of the present invention.

9 Claims, 21 Drawing Sheets

U.S. PATENT DOCUMENTS

| | | | |
|---|---|---|---|
| 4,493,795 | A | 1/1985 | Nestor et al. |
| 4,493,890 | A | 1/1985 | Morris |
| 5,625,048 | A | 4/1997 | Tsien et al. |
| 5,777,079 | A | 7/1998 | Tsien et al. |
| 5,891,646 | A | 4/1999 | Barak et al. |
| 6,066,476 | A | 5/2000 | Tsien et al. |
| 6,110,693 | A | 8/2000 | Barak et al. |

OTHER PUBLICATIONS

Ngo et al (1994) "The Protein Folding Problem and Tertiary Structure Prediction, Chapter 14: Computational Complexity Protein Structure Prediction, and the Levinthal Paradox" pp. 433-440 and 492-495 only.*

Bork (2000) Genome Research 10:398.*

Skolnick et al (2000) Trends in Biotech. 18(1): 34.*

Doerks et al (1998) Trends in Genetics 14(6): 248.*

Smith et al (1997) Nature Biotechnology 15:1222.*

Brenner (1999) Trends in Genetics 15(4): 132.*

Bork et al (1996) Trends in Genetics 12(10): 425.*

Angers, S., et al., "Detection $\beta_2$-adrenergic receptor dimerization in living cells using bioluminescence resonance energy transfer (BRET)," *Proc. Natl. Acad. Sci. USA* 97(7):3684-3689 (Mar. 2000).

Claing, A., et al., "$\beta$-Arrestin-mediated ADP-ribosylation factor 6 activation and $\beta_2$-adrenergic receptor endocytosis," *J. Biol. Chem.* 276(45):42509-42513 (Nov. 2001) (first pub'd online Aug. 30, 2001).

Cong, M., et al., "Binding of the $\beta_2$ adrenergic receptor to N-ethylmaleimide-sensitive factor regulates receptor recycling," *J. Biol. Chem.* 276(48):45145-45152 (Nov. 2001) (first pub'd online Sep. 27, 2001).

Edge, M., et al., "Total synthesis of a human leukocyte interferon gene," *Nature* 292(5825):756-762 (Aug. 1981).

Govers, R., et al., "Identification of a novel ubiquitin conjugation motif, required for ligand-induced internalization of the growth hormone receptor," *EMBO J.* 18(1):28-36 (Jan. 1999).

Hershko, A., et al., "The ubiquitin system," *Annu. Rev. Biochem.* 67:425-479 (1998).

Hicke, L., et al., "Ubiquitination of a yeast plasma membrane receptor signals its ligand-stimulated endocytosis," *Cell* 84(2):277-287 (Jan. 1996).

Jay, E., et al., "Chemical synthesis of a biologically active gene for human immune interferon-$\gamma$. Prospect for site-specific mutagenesis and structure- function studies," *J. Biol. Chem.* 259(10):6311-6317 (May 1984).

Krupnick, J., et al., Arrestin/clathrin interaction. Localization of the clathrin binding domain of nonvisual arrestins to the carboxy terminus *J. Biol. Chem.* 272(23):15011-15016 (Jun. 1997).

Laporte, S., et al., "The $\beta$2-adrenergic receptor/$\beta$arrestin complex recruits the clathrin adaptor AP-2 during endocytosis," *Proc. Natl. Acad. Sci. USA* 96(7):3712-3717 (Mar. 1999).

Lefkovitz, R., "G protein-coupled receptors. III. New roles for receptor kinases and $\beta$-arrestins in receptor signaling and desensitization," *J. Biol. Chem.* 273(30):18677-18680 (Jul. 1998).

Luttrell, L., et al. "$\beta$-arrestin-dependent formation of $\beta$2 adrenergic receptor-Src protein kinase complexes," *Science* 283(5402):655-661 (Jan. 1999).

Luttrell, L., et al., "Activation and targeting of extracellular signal-regulated kinases by $\beta$-arrestin scaffolds," *Proc. Natl. Acad. Sci. USA* 98(5):2449-2454 (Feb. 2001) (first pub'd online Feb. 20, 2001).

Mori, S., et al., "Identification of an ubiquitin-ligation system for the epidermal-growth-factor receptor—herbimycin A induces in vitro ubiquitination in rabbit-reticulocyte lysate," *Eur. J. Biochem.* 247(3):1190-1196 (Aug. 1997).

Mori, S., et al., "Degradation process of ligand-stimulated platelet-derived growth factor $\beta$-receptor involves ubiquitin-proteasome proteolytic pathway," *J. Biol. Chem.* 270(49):29447-29452 (Dec. 1995).

Nambiar, K., et al., "Total synthesis and cloning of a gene coding for the ribonuclease S protein," *Science* 223(4642):1299 (Mar. 1984).

Niman, H., et al., "Generation of protein-reactive antibodies by short peptides is an event of high frequency: implications for the structural basis of immune recognition," *Proc. Natl. Acad. Sci. USA* 80(16):4949-4953 (Aug. 1983).

Noren, C., et al., "A general method for site-specific incorporation of unnatural amino acids into proteins," *Science* 244(4901):182-188 (Apr. 1989).

Oakley, R., et al., "Differential affinities of visual arrestin, $\beta$arrestin1, and $\beta$arrestin2 for G protein-coupled receptors delineate two major classes of receptors," *J. Biol. Chem.* 275(22):17201-17210 (Jun. 2000).

Oakley, R., et al., "Molecular determinants underlying the formation of stable intracellular G protein-coupled receptor-$\beta$ -arrestin complexes after receptor endocytosis," *J. Biol Chem.* 276(22):19452-19460 (Jun. 2001) (first pub'd online Mar. 9, 2001).

Perry, S., et al., "Arresting developments in heptahelical receptor signaling and regulation," *Trends Cell Biol.* 12(3):130-138 (Mar. 2002).

Phonphok, Y., et al., "Stabilization of clathrin coated vesicles by amantadine, tromantadine and other hydrophobic amines," *FEBS Lett.* 281(1-2):188-190 (Apr. 1991).

Roth, A., et al., "Ubiquitination of the yeast a-factor receptor," *J. Cell. Biol.* 134(3):661-674 (Aug. 1996).

Shenoy, S., et al., "Regulation of receptor fate by ubiquitination of activated beta 2-adrenergic receptor and beta-arrestin," *Science* 294(5545):1307-1313 (Mar. 2001) (first pub'd online Oct. 4, 2001).

Tohgo, A., et al., "$\beta$-Arrestin scaffolding of the ERK cascade enhances cytosolic ERK activity but inhibits ERK-mediated transcription following angiotensin AT1a receptor stimulation," *J. Biol. Chem.* 277(11):9429-9436 (Mar. 2002) (first pub'd online Jan. 2, 2002).

Wang, C., et al., "TAK1 is a ubiquitin-dependent kinase of MKK and IKK," *Nature* 412(6844):346-351 (Jul. 2001).

Wang, Y., el al., "Down-regulation of protease-activated receptor-1 is regulated by sorting nexin 1," *Mol. Biol. Cell* 13(6):1965-1976 (Jun. 2002).

Zheng, B., et al., "RGS-PX1, a GAP for G$\alpha_s$ and sorting nexin in vesicular," *Science* 294(5548):1939-1942 (Nov. 2001).

* cited by examiner

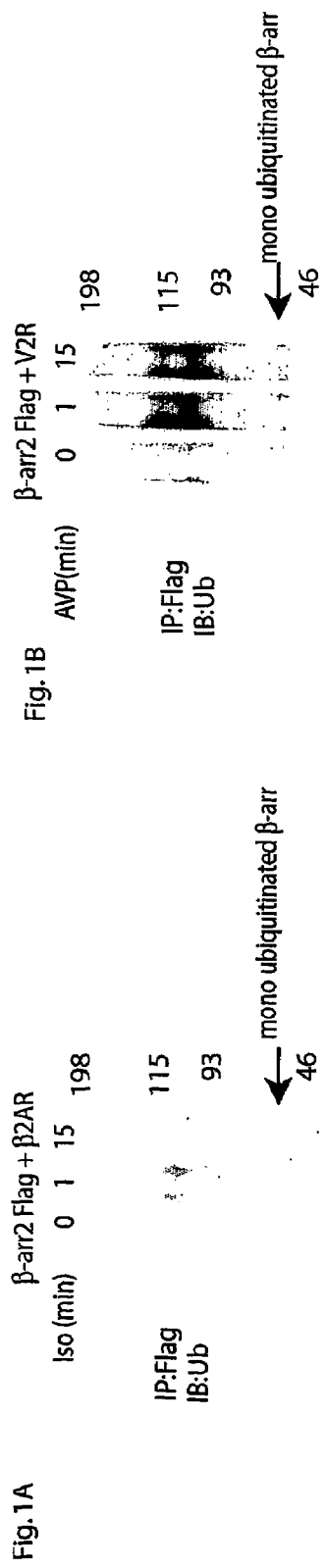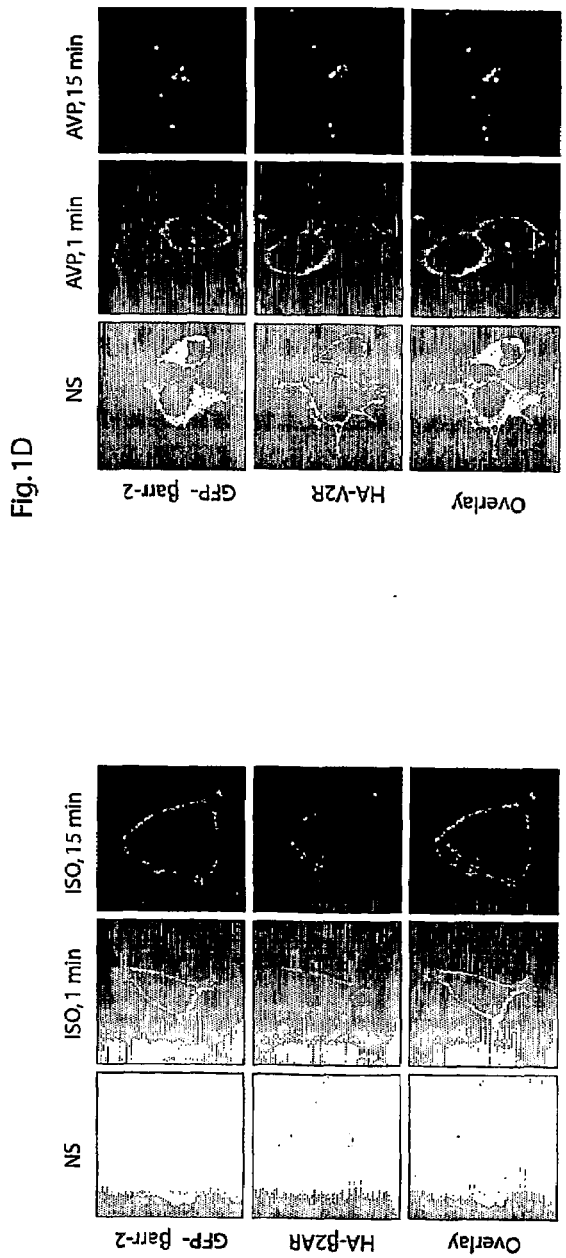

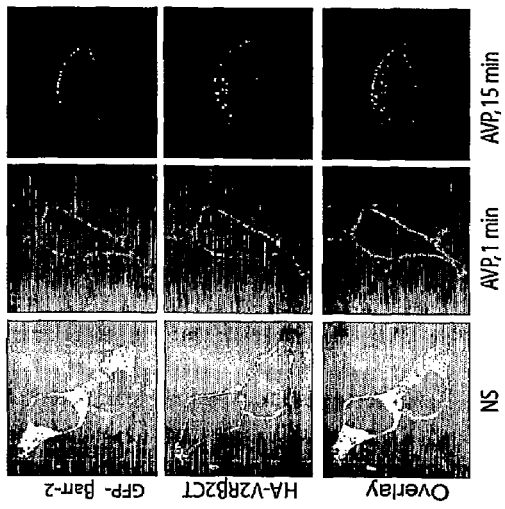
Fig. 2B
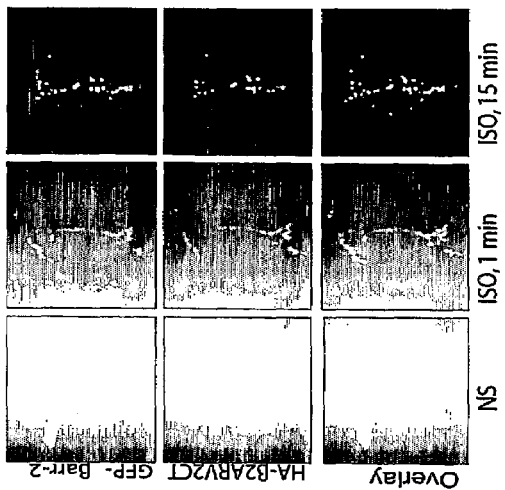
Fig. 2A
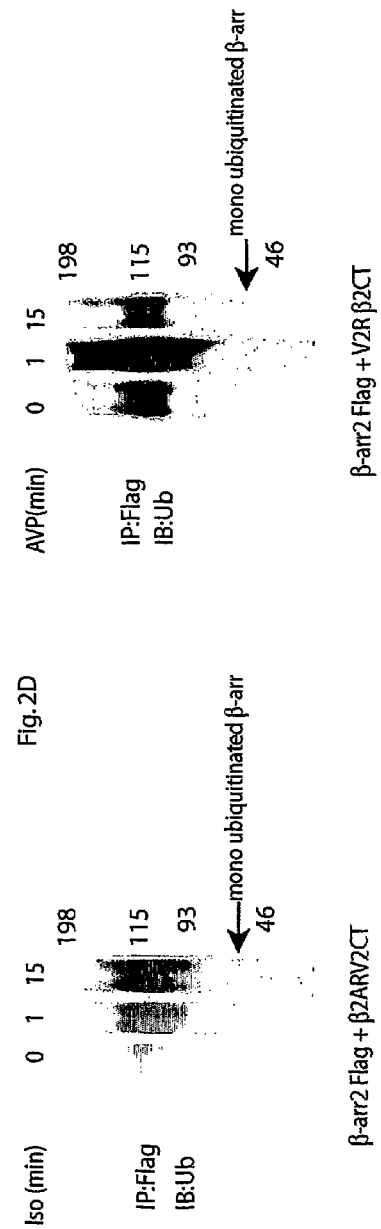

Fig. 3A
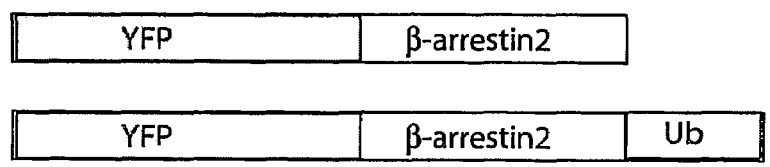
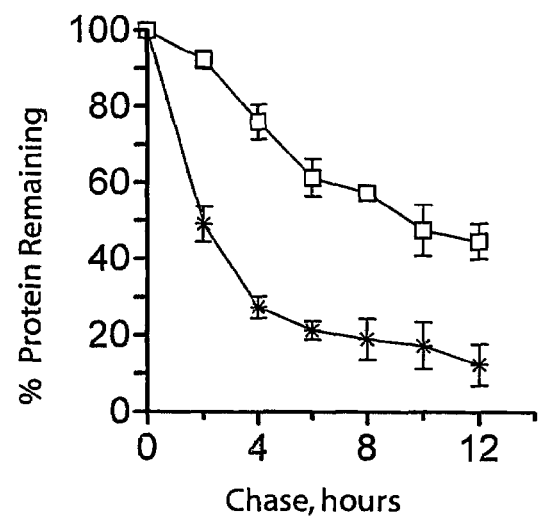

FIG. 8A

EYFP-BARR2-Ub

```
661/221                                 691/231
CTG CTG GAG TTC GTG ACC GCC GCC GGG ATC ACT CTC GGC ATG GAC GAG CTG TAC AAG TCC
 L   L   E   F   V   T   A   A   G   I   T   L   G   M   D   E   L   Y   K   S
721/241                                 751/251
GGA CTC AGA TCT CGA GCT CAA GCT TCG AAT TCT GCA GTC GAC GGT ACC ACG CGC ACC
 G   L   R   S   R   A   Q   A   S   N   S   A   V   D   G   T   T   R   T
1/1                                     31/11
ATG GGT GAA AAA CCC GGG ACC AGG GTC TTC AAG AAG TCG AGC CCT AAC TGC AAG CTC ACC
 M   G   E   K   P   G   T   R   V   F   K   K   S   S   P   N   C   K   L   T
61/21                                   91/31
GTG TAC TTG GGC AAG CGT GAC TTT GTG GAT CAC TTG GAC AAA GTG GAT CCT GTC GAT GGT
 V   Y   L   G   K   R   D   F   V   D   H   L   D   K   V   D   P   V   D   G
121/41                                  151/51
GTG GTG CTT GTG GAT CCT GAC TAC TTG AAG GAC CGG AAA GTG TTT GTG ACC CTC ACC TGT
 V   V   L   V   D   P   D   Y   L   K   D   R   K   V   F   V   T   L   T   C
181/61                                  211/71
GCC TTC CGC TAT GGC CGA GAA GAC CTG GAT GTA CTG GGC CTG TCT TTC CGC AAA GAT CTG
 A   F   R   Y   G   R   E   D   L   D   V   L   G   L   S   F   R   K   D   L
241/81                                  271/91
TTC ATC GCC ACC TAC CAG GCC TTC CCC CCC ATG CCC AAC CCA CCT CGG CCC CCC ACC CGC
 F   I   A   T   Y   Q   A   F   P   P   M   P   N   P   P   R   P   P   T   R
301/101                                 331/111
CTA CAG GAC CGA CTG CTG AAG AAG TTG GGC CAG CAT GCC CAC CCC TTT TTT TTC ACA ATA
 L   Q   D   R   L   L   K   K   L   G   Q   H   A   H   P   F   F   F   T   I
361/121                                 391/131
CCC CAG AAT TTG CCT TGC TCC GTC ACA CTG CAG CCA GGA CCG GAG GAC ACA GGG AAG GCC
 P   Q   N   L   P   C   S   V   T   L   Q   P   G   P   E   D   T   G   K   A
421/141                                 451/151
TGT GGA GTA GAC TTT GAG ATT CGA GCC TTC TGT GCC AAA TCT ATA GAA GAA AAA AGC CAC
 C   G   V   D   F   E   I   R   A   F   C   A   K   S   I   E   E   K   S   H
481/161                                 511/171
AAA AGG AAC TCC GTG CGG CTT ATC ATC AGA AAG GTA CAG TTT GCT CCT GAG ACA CCC GGC
 K   R   N   S   V   R   L   I   I   R   K   V   Q   F   A   P   E   T   P   G
541/181                                 571/191
CCC CAG CCA TCA GCT GAA ACC ACA CGC CAC TTC CTC ATG TCT GAC CGG AGG TCC CTG CAC
 P   Q   P   S   A   E   T   T   R   H   F   L   M   S   D   R   R   S   L   H
601/201                                 631/211
CTA GAG GCT TCC CTG GAC AAA GAG CTG TAC TAC CAT GGG GAA CCC CTC AAT GTC AAC GTC
 L   E   A   S   L   D   K   E   L   Y   Y   H   G   E   P   L   N   V   N   V
661/221                                 691/231
CAC GTC ACC AAC AAT TCT GCC AAG ACC GTC AAG AAG ATC AGA GTG TCT GTG AGA CAG TAT
 H   V   T   N   N   S   A   K   T   V   K   K   I   R   V   S   V   R   Q   Y
721/241                                 751/251
GCC GAC ATT TGC CTC TTC AGC ACC GCG CAG TAC AAG TGT CCT GTG GCT CAG CTT GAA CAA
 A   D   I   C   L   F   S   T   A   Q   Y   K   C   P   V   A   Q   L   E   Q
781/261                                 811/271
GAT GAC CAG GTG TCT CCC AGT TCC ACA TTC TGC AAG GTG TAC ACC ATA ACC CCG CTG CTC
 D   D   Q   V   S   P   S   S   T   F   C   K   V   Y   T   I   T   P   L   L
841/281                                 871/291
AGT GAC AAC CGA GAG AAG CGT GGC CTT GCC CTT GAT GGG CAA CTC AAG CAC GAA GAC ACC
 S   D   N   R   E   K   R   G   L   A   L   D   G   Q   L   K   H   E   D   T
901/301                                 931/311
AAC CTG GCT TCC AGC ACC ATT GTG AAG GAG GGA GCC AAC AAG GAG GTG CTG GGA ATC CTA
 N   L   A   S   S   T   I   V   K   E   G   A   N   K   E   V   L   G   I   L
961/321                                 991/331
GTA TCC TAC AGG GTC AAG GTG AAG CTG GTG GTG TCT CGA GGG GGT GAT GTC TCC GTG GAG
 V   S   Y   R   V   K   V   K   L   V   V   S   R   G   G   D   V   S   V   E
1021/341                                1051/351
CTA CCT TTC GTC CTA ATG CAC CCC AAG CCC CAC GAC CAC ATC ACC CTT CCC CGA CCC CAG
 L   P   F   V   L   M   H   P   K   P   H   D   H   I   T   L   P   R   P   Q
1081/361                                1111/371
TCA GCC CCC CGG GAA ATA GAC ATC CCT GTG GAT ACC AAC CTC ATT GAA TTC GAT ACC AAC
 S   A   P   R   E   I   D   I   P   V   D   T   N   L   I   E   F   D   T   N
1141/381                                1171/391
TAT GCC ACA GAC GAC GAC ATC GTG TTT GAG GAC TTT GCG AGG CTT CGG CTG AAG GGG ATG
 Y   A   T   D   D   D   I   V   F   E   D   F   A   R   L   R   L   K   G   M
1201/401                                1231/410
```

FIG. 8B

```
AAG GAT GAC GAC TGT GAT GAC CAG TTC TGC GTC GAC CAG ATC TTC GTG AAG ACT CTG
 K   D   D   D   C   D   D   Q   F   C   V   D   Q   I   F   V   K   T   L
22/8                                    52/18
ACT GGT AAG ACC ATC ACC CTC GAG GTG GAG CCC AGT GAC ACC ATC GAG AAT GTC AAG GCA
 T   G   K   T   I   T   L   E   V   E   P   S   D   T   I   E   N   V   K   A
82/28                                   112/38
AAG ATC CAA GAT AAG GAA GGC ATT CCT CCT GAT CAG CAG AGG TTG ATC TTT GCC GGA AAA
 K   I   Q   D   K   E   G   I   P   P   D   Q   Q   R   L   I   F   A   G   K
142/48                                  172/58
CAG CTG GAA GAT GGT CGT ACC CTG TCT GAC TAC AAC ATC CAG AAA GAG TCC ACC TTG CAC
 Q   L   E   D   G   R   T   L   S   D   Y   N   I   Q   K   E   S   T   L   H
202/68
CTG GTA CTC CGT CTC AGA GGT GGG TGA
 L   V   L   R   L   R   G   G   ***
```

FIG. 9A

```
EYFP-BARR2-Ub48
661/221                                    691/231
CTG CTG GAG TTC GTG ACC GCC GCC GGG ATC ACT CTC GGC ATG GAC GAG CTG TAC AAG TCC
 L   L   E   F   V   T   A   A   G   I   T   L   G   M   D   E   L   Y   K   S
721/241                                    751/251
GGA CTC AGA TCT CGA GCT CAA GCT TCG AAT TCT GCA GTC GAC GGT ACC ACG CGC ACC
 G   L   R   S   R   A   Q   A   S   N   S   A   V   D   G   T   T   R   T
1/1                                        31/11
ATG GGT GAA AAA CCC GGG ACC AGG GTC TTC AAG AAG TCG AGC CCT AAC TGC AAG CTC ACC
 M   G   E   K   P   G   T   R   V   F   K   K   S   S   P   N   C   K   L   T
61/21                                      91/31
GTG TAC TTG GGC AAG CGT GAC TTT GTG GAT CAC TTG GAC AAA GTG GAT CCT GTC GAT GGT
 V   Y   L   G   K   R   D   F   V   D   H   L   D   K   V   D   P   V   D   G
121/41                                     151/51
GTG GTG CTT GTG GAT CCT GAC TAC TTG AAG GAC CGG AAA GTG TTT GTG ACC CTC ACC TGT
 V   V   L   V   D   P   D   Y   L   K   D   R   K   V   F   V   T   L   T   C
181/61                                     211/71
GCC TTC CGC TAT GGC CGA GAA GAC CTG GAT GTA CTG GGC CTG TCT TTC CGC AAA GAT CTG
 A   F   R   Y   G   R   E   D   L   D   V   L   G   L   S   F   R   K   D   L
241/81                                     271/91
TTC ATC GCC ACC TAC CAG GCC TTC CCC CCC ATG CCC AAC CCA CCT CGG CCC CCC ACC CGC
 F   I   A   T   Y   Q   A   F   P   P   M   P   N   P   P   R   P   P   T   R
301/101                                    331/111
CTA CAG GAC CGA CTG CTG AAG AAG TTG GGC CAG CAT GCC CAC CCC TTT TTT TTC ACA ATA
 L   Q   D   R   L   L   K   K   L   G   Q   H   A   H   P   F   F   F   T   I
361/121                                    391/131
CCC CAG AAT TTG CCT TGC TCC GTC ACA CTG CAG CCA GGA CCG GAG GAC ACA GGG AAG GCC
 P   Q   N   L   P   C   S   V   T   L   Q   P   G   P   E   D   T   G   K   A
421/141                                    451/151
TGT GGA GTA GAC TTT GAG ATT CGA GCC TTC TGT GCC AAA TCT ATA GAA GAA AAA AGC CAC
 C   G   V   D   F   E   I   R   A   F   C   A   K   S   I   E   E   K   S   H
481/161                                    511/171
AAA AGG AAC TCC GTG CGG CTT ATC ATC AGA AAG GTA CAG TTT GCT CCT GAG ACA CCC GGC
 K   R   N   S   V   R   L   I   I   R   K   V   Q   F   A   P   E   T   P   G
541/181                                    571/191
CCC CAG CCA TCA GCT GAA ACC ACA CGC CAC TTC CTC ATG TCT GAC CGG AGG TCC CTG CAC
 P   Q   P   S   A   E   T   T   R   H   F   L   M   S   D   R   R   S   L   H
601/201                                    631/211
CTA GAG GCT TCC CTG GAC AAA GAG CTG TAC TAC CAT GGG GAA CCC CTC AAT GTC AAC GTC
 L   E   A   S   L   D   K   E   L   Y   Y   H   G   E   P   L   N   V   N   V
661/221                                    691/231
CAC GTC ACC AAC AAT TCT GCC AAG ACC GTC AAG AAG ATC AGA GTG TCT GTG AGA CAG TAT
 H   V   T   N   N   S   A   K   T   V   K   K   I   R   V   S   V   R   Q   Y
721/241                                    751/251
GCC GAC ATT TGC CTC TTC AGC ACC GCG CAG TAC AAG TGT CCT GTG GCT CAG CTT GAA CAA
 A   D   I   C   L   F   S   T   A   Q   Y   K   C   P   V   A   Q   L   E   Q
781/261                                    811/271
GAT GAC CAG GTG TCT CCC AGT TCC ACA TTC TGC AAG GTG TAC ACC ATA ACC CCG CTG CTC
 D   D   Q   V   S   P   S   S   T   F   C   K   V   Y   T   I   T   P   L   L
841/281                                    871/291
AGT GAC AAC CGA GAG AAG CGT GGC CTT GCC CTT GAT GGG CAA CTC AAG CAC GAA GAC ACC
 S   D   N   R   E   K   R   G   L   A   L   D   G   Q   L   K   H   E   D   T
901/301                                    931/311
AAC CTG GCT TCC AGC ACC ATT GTG AAG GAG GGA GCC AAC AAG GAG GTG CTG GGA ATC CTA
 N   L   A   S   S   T   I   V   K   E   G   A   N   K   E   V   L   G   I   L
961/321                                    991/331
GTA TCC TAC AGG GTC AAG GTG AAG CTG GTG GTG TCT CGA GGC GGG GAT GTC TCC GTG GAG
 V   S   Y   R   V   K   V   K   L   V   V   S   R   G   G   D   V   S   V   E
1021/341                                   1051/351
CTA CCT TTC GTC CTA ATG CAC CCC AAG CCC CAC GAC CAC ATC ACC TTG CCC CGA CCC CAG
 L   P   F   V   L   M   H   P   K   P   H   D   H   I   T   L   P   R   P   Q
1081/361                                   1111/371
TCA GCC CCC CGG GAA ATA GAC ATC CCT GTG GAT ACC AAC CTC ATT GAA TTC GAT ACC AAC
 S   A   P   R   E   I   D   I   P   V   D   T   N   L   I   E   F   D   T   N
1141/381                                   1171/391
TAT GCC ACA GAC GAC GAC ATC GTG TTT GAG GAC TTT GCG AGG CTT CGG CTG AAG GGG ATG
 Y   A   T   D   D   D   I   V   F   E   D   F   A   R   L   R   L   K   G   M
1201/401                                   1231/410
```

FIG. 9B

```
AAG GAT GAC GAC TGT GAT GAC CAG TTC TGC GTC GAC CAG ATT TTC GTC AAG ACT TTG
 K   D   D   D   C   D   D   Q   F   C   V   D   Q   I   F   V   K   T   L
22/8                                    52/18
ACC GGT AAA ACC ATA ACA TTG GAA GTT GAA TCT TCC GAT ACC ATC GAC AAC GTT AAG TCG
 T   G   K   T   I   T   L   E   V   E   S   S   D   T   I   E   N   V   K   S
82/28                                   112/38
AAA ATT CAA GAC AAG GAA GGT ATC CCT CCA GAT CAA CAA AGA TTG ATC TTT GCC GGT AGG
 K   I   Q   D   K   E   G   I   P   P   D   Q   Q   R   L   I   F   A   G   R
142/48                                  172/58
CAG CTA GAA GAC GGT AGA ACG CTG TCT GAT TAC AAC ATT CAG AAG GAG TCC ACC TTA CAT
 Q   L   E   D   G   R   T   L   S   D   Y   N   I   Q   K   E   S   T   L   H
202/68
CTT GTG CTA AGG CTA AGA GGT GGT TGA
 L   V   L   R   L   R   G   G   ***
```

FIG. 10A

EGFP-BARR2-Ub48
661/221                                    691/231
CTG CTG GAG TTC GTG ACC GCC GCC GGG ATC ACT CTC GGC ATG GAC GAG CTG TAC AAG TCC
 L   L   E   F   V   T   A   A   G   I   T   L   G   M   D   E   L   Y   K   S
721/241                                    751/251
GGA CTC AGA TCT CGA GCT CAA GCT TCG AAT TCT GCA GTC GAC GGT ACC ACG CGC ACC
 G   L   R   S   R   A   Q   A   S   K   S   A   V   D   G   T   T   R   T
1/1                                        31/11
ATG GGT GAA AAA CCC GGG ACC AGG GTC TTC AAG AAG TCG AGC CCT AAC TGC AAG CTC ACC
 M   G   E   K   P   G   T   R   V   F   K   K   S   S   P   N   C   K   L   T
61/21                                      91/31
GTG TAC TTG GGC AAG CGT GAC TTT GTG GAT CAC TTG GAC AAA GTG GAT CCT GTC GAT GGT
 V   Y   L   G   K   R   D   F   V   D   H   L   D   K   V   D   P   V   D   G
121/41                                     151/51
GTG GTG CTT GTG GAT CCT GAC TAC TTG AAG GAC CGG AAA GTG TTT GTG ACC CTC ACC TGT
 V   V   L   V   D   P   D   Y   L   K   D   R   K   V   F   V   T   L   T   C
181/61                                     211/71
GCC TTC CGC TAT GGC CGA GAA GAC CTG GAT GTA CTG GGC CTG TCT TTC CGC AAA GAT CTG
 A   F   R   Y   G   R   E   D   L   D   V   L   G   L   S   F   R   K   D   L
241/81                                     271/91
TTC ATC GCC ACC TAC CAG GCC TTC CCC CCC ATG CCC AAC CCA CCT CGG CCC CCC ACC CGC
 F   I   A   T   Y   Q   A   F   P   P   M   P   N   P   P   R   P   P   T   R
301/101                                    331/111
CTA CAG GAC CGA CTG CTG AAG AAG TTG GGC CAG CAT GCC CAC CCC TTT TTT TTC ACA ATA
 L   Q   D   R   L   L   K   K   L   G   Q   H   A   H   P   F   F   F   T   I
361/121                                    391/131
CCC CAG AAT TTG CCT TGC TCC GTC ACA CTG CAG CCA GGA CCG GAG GAC ACA GGG AAG GCC
 P   Q   N   L   P   C   S   V   T   L   Q   P   G   P   E   D   T   G   K   A
421/141                                    451/151
TGT GGA GTA GAC TTT GAG ATT CGA GCC TTC TGT GCC AAA TCT ATA GAA GAA AAA AGC CAC
 C   G   V   D   F   E   I   R   A   F   C   A   K   S   I   E   E   K   S   H
481/161                                    511/171
AAA AGG AAC TCC GTG CGG CTT ATC ATC AGA AAG GTA CAG TTT GCT CCT GAG ACA CCC GGC
 K   R   N   S   V   R   L   I   I   R   K   V   Q   F   A   P   E   T   P   G
541/181                                    571/191
CCC CAG CCA TCA GCT GAA ACC ACA CGC CAC TTC CTC ATG TCT GAC CGG AGG TCC CTG CAC
 P   Q   P   S   A   E   T   T   R   H   F   L   M   S   D   R   R   S   L   H
601/201                                    631/211
CTA GAG GCT TCC CTG GAC AAA GAG CTG TAC TAC CAT GGG GAA CCC CTC AAT GTC AAC GTC
 L   E   A   S   L   D   K   E   L   Y   Y   H   G   E   P   L   N   V   N   V
661/221                                    691/231
CAC GTC ACC AAC AAT TCT GCC AAG ACC GTC AAG AAG ATC AGA GTG TCT GTG AGA CAG TAT
 H   V   T   N   N   S   A   K   T   V   K   K   I   R   V   S   V   R   Q   Y
721/241                                    751/251
GCC GAC ATT TGC CTC TTC AGC ACC GCG CAG TAC AAG TGT CCT GTG GCT CAG CTT GAA CAA
 A   D   I   C   L   F   S   T   A   Q   Y   K   C   P   V   A   Q   L   E   Q
781/261                                    811/271
GAT GAC CAG GTG TCT CCC AGT TCC ACA TTC TGC AAG GTG TAC ACC ATA ACC CCG CTG CTC
 D   D   Q   V   S   P   S   S   T   F   C   K   V   Y   T   I   T   P   L   L
841/281                                    871/291
AGT GAC AAC CGA GAG AAG CGT GGC CTT GCC CTT GAT GGG CAA CTC AAG CAC GAA GAC ACC
 S   D   N   R   E   K   R   G   L   A   L   D   G   Q   L   K   H   E   D   T
901/301                                    931/311
AAC CTG GCT TCC AGC ACC ATT GTG AAG GAG GGA GCC AAC AAG GAG GTG CTG GGA ATC CTA
 N   L   A   S   S   T   I   V   K   E   G   A   N   K   E   V   L   G   I   L
961/321                                    991/331
GTA TCC TAC AGG GTC AAG GTG AAG CTG GTG GTG TCT CGA GGC GGG GAT GTC TCC GTG GAG
 V   S   Y   R   V   K   V   K   L   V   V   S   R   G   G   D   V   S   V   E
1021/341                                   1051/351
CTA CCT TTC GTC CTA ATG CAC CCC AAG CCC CAC GAC CAC ATC ACC CTT CCC CGA CCC CAG
 L   P   F   V   L   M   H   P   K   P   H   D   H   I   T   L   P   R   P   Q
1081/361                                   1111/371
TCA GCC CCC CGG GAA ATA GAC ATC CCT GTG GAT ACC AAC CTC ATT GAA TTC GAT ACC AAC
 S   A   P   R   E   I   D   I   P   V   D   T   N   L   I   E   F   D   T   N
1141/381                                   1171/391
TAT GCC ACA GAC GAC GAC ATC GTG TTT GAG GAC TTT GCG AGG CTT CGG CTG AAG GGG ATG
 Y   A   T   D   D   D   I   V   F   E   D   F   A   R   L   R   L   K   G   M
1201/401                                   1231/410

FIG. 10B

```
AAG GAT GAC GAC TGT GAT GAC CAG TTC TGC GTC GAC CAG ATC TTC GTG AAG ACT CTG
 K   D   D   D   C   D   D   Q   F   C   V   D   Q   I   F   V   K   T   L
22/8                                    52/18
ACT GGT AAG ACC ATC ACC CTC GAG GTG GAG CCC AGT GAC ACC ATC GAG AAT GTC AAG GCA
 T   G   K   T   I   T   L   E   V   E   P   S   D   T   I   E   N   V   K   A
82/28                                       112/38
AAG ATC CAA GAT AAG GAA GGC ATT CCT CCT GAT CAG CAG AGG TTG ATC TTT GCC GGA AGA
 K   I   Q   D   K   E   G   I   P   P   D   Q   Q   R   L   I   F   A   G   R
142/48                                      172/58
CAG CTG GAA GAT GGT CGT ACC CTG TCT GAC TAC AAC ATC CAG AAA GAG TCC ACC TTG CAC
 Q   L   E   D   G   R   T   L   S   D   Y   N   I   Q   K   E   S   T   L   H
202/68
CTG GTA CTC CGT CTC AGA GGT GGG TGA
 L   V   L   R   L   R   G   G   ***
```

FIG. 11A  Human G Protein Coupled Receptor Family
(Receptors known as of January, 1999)

| CLASS | LIGAND | NUMBER | TISSUE | PHYSIOLOGY | THERAPEUTICS |
|---|---|---|---|---|---|
| Class I Rhodopsin like | | | | | |
| | •Amine | | | | |
| | ·Acetylcholine (muscarinic & nicotinic) | 5 | Brain, Nerves, Heart | Neurotransmitter | Acuity, Alzheimer's |
| | ·Adrenoceptors | | | | |
| | ·Alpha Adrenoceptors | 6 | Brain, Kidney, Lung | Gluconeogenesis | Diabetes, Cardiovascular |
| | ·Beta Adrenoceptors | 3 | Kidney, Heart | Muscle Contraction | Cardiovascular, Respiratory |
| | ·Dopamine | 5 | Brain, Kidney, GI | Neurotransmitter | Cardiovascular, Parkinson's |
| | ·Histamine | 2 | Vascular, Heart, Brain | Vascular Permeability | Anti-inflammatory, Ulcers |
| | ·Serotonin (5-HT) | 16 | Most Tissues | Neurotransmitter | Depression, Insomnia, Analgesic |
| | •Peptide | | | | |
| | ·Angiotensin | 2 | Vascular, Liver, Kidney | Vasoconstriction | Cardiovascular, Endocrine |
| | ·Bradykinin | 1 | Liver, Blood | Vasodilation, | Anti-inflammatory, Asthma |
| | ·C5a anaphylatoxin | 1 | Blood | Immune System | Anti-inflammatory |
| | ·Fmet-leu-phe | 3 | Blood | Chemoattractant | Anti-inflammatory |
| | ·Interleukin-8 | 1 | Blood | Chemoattractant | Anti-inflammatory |
| | ·Chemokine | 6 | Blood | Chemoattractant | Anti-inflammatory |
| | ·Orexin | 2 | Brain | Fat Metabolism | Obesity |
| | ·Nociceptin | 1 | Brain | Bronchodilator, Pain | Airway Diseases, Anesthetic |
| | ·CCK (Gastrin) | 2 | Gastrointestinal | Motility, Fat Absorption | Gastrointestinal, Obesity, Parkinson's |
| | ·Endothelin | 2 | Heart, Bronchus, Brain | Muscle Contraction | Cardiovascular, Respiratory |
| | ·Melanocortin | 5 | Kidney, Brain | Metabolic Regulation | Anti-inflammatory, Analgesics |
| | ·Neuropeptide Y | 5 | Nerves, Intestine, Blood | Neurotransmitter | Behavior, Memory, Cardiovascular |
| | ·Neurotensin | 1 | Brain, | CNS | Cardiovascular, Analgesic |

FIG. 11B

| | | | |
|---|---|---|---|
| ·Opioid | 3 | Brain, | CNS | Depression, Analgesic |
| ·Somatostatin | 5 | Brain, Gastrointestinal | Neurotransmitter | Oncology, Alzheimer's |
| ·Tachykinin (Substance P, NKA₁) | 3 | Brain Nerves | Neurohormone | Depression, Analgesic |
| ·Thrombin | 3 | Platelets, Blood Vessels | Coagulation | Anti-coagulant, Anti-inflammatory |
| ·Vasopressin-like | 4 | Arteries, Heart, Bladder | Water Balance | Anti-diuretic, Diabetic Complications |
| ·Galanin | 1 | Brain, Pancreas | Neurotransmitter | Analgesics, Alzheimer's |
| ·Hormone protein | | | | |
| ·Follicle stimulating hormone | 1 | Ovary, Testis | Endocrine | Infertility |
| ·Lutropin-choriogonadotropic | 1 | Ovary, Testis | Endocrine | Infertility |
| ·Thyrotropin | 1 | Thyroid | Endocrine | Thyroidism, Metabolism |
| ·(Rhod)opsin | | | | |
| ·Opsin | 5 | Eye | Photoreception | Ophthalmic Diseases |
| ·Olfactory | 4(~1000) | Nose | Smell | Olfactory Diseases |
| ·Prostanoid | | | | |
| ·Prostaglandin | 5 | Arterial, Gastrointestinal | Vasodilation, Pain | Cardiovascular, Analgesic |
| ·Lysophosphatidic Acid | 2 | Vessels, Heart, Lung | Inflammation | Cancer, Anti-Inflammatory |
| ·Sphingosine-1-phosphate | 2 | Most Cells | Cell proliferation | Cancer |
| ·Leukotriene | 1 | White Blood Cells, Bronchus | Inflammation | Asthma, Rheumatoid Arthritis |
| ·Prostacyclin | 1 | Arterial, Gastrointestinal | Platelet Regulation | Cardiovascular |
| ·Thromboxane | 1 | Arterial, Bronchus | Vasoconstriction | Cardiovascular, Respiratory |
| ·Nucleotide-like | | | | |
| ·Adenosine | 4 | Vascular, Bronchus | Multiple Effects | Cardiovascular, Respiratory |
| ·Purinoceptors | 4 | Vascular, Platelets | Relaxes Muscle | Cardiovascular, Respiratory |
| ·Cannabis | 2 | Brain | Sensory Perception | Analgesics, Memory |
| ·Platelet activating factor | 1 | Most Peripheral Tissues | Inflammation | Anti-inflammatory, Anti-asthmatic |

FIG. 11C

| | | | |
|---|---|---|---|
| | ·Gonadotropin-releasing hormone like | | |
| | ·Gonadotropin-releasing hormone | 1 | Reproductive Organs, Pituitary | Reproduction | Prostate Cancer, Endometriosis |
| | ·Thyrotropin-releasing hormone | 1 | Pituitary, Brain | Thyroid Regulation | Metabolic Regulation |
| | ·Growth hormone- inhibiting factor | 1 | Gastrointestinal | Neuroendocrine | Oncology, Alzheimer's |
| | ·Melatonin | 1 | Brain, Eye, Pituitary | Neuroendocrine | Regulation of Circadian Cycle |
| ·Class II Secretin like | | | | | |
| | ·Secretin | 1 | Gastrointestinal, Heart | Digestion | Obesity, Gastrointestinal |
| | ·Calcitonin | 1 | Bone, Brain | Calcium Resorption | Osteoporosis |
| | ·Corticotropin releasing factor/urocortin | 1 | Adrenal, Vascular, Brain | Neuroendocrine | Stress, Mood, Obesity |
| | ·Gastric inhibitory peptide (GIP) | 1 | Adrenals, Fat Cells | Sugar/Fat Metabolism | Diabetes, Obesity |
| | ·Glucagon | 1 | Liver, Fat Cells, Heart | Gluconeogenesis | Cardiovascular |
| | ·Glucagon-like Peptide 1 (GLP-1) | 1 | Pancreas, Stomach, Lung | Gluconeogenesis | Cardiovascular, Diabetes, Obesity |
| | ·Growth hormone-releasing hormone | 1 | Brain | Neuroendocrine | Growth Regulation |
| | ·Parathyroid hormone | 1 | Bone, Kidney | Calcium Regulation | Osteoporosis |
| | ·PACAP | 1 | Brain, Pancreas, Adrenals | Metabolism | Metabolic Regulation |
| | ·Vasoactive intestinal polypeptide (VIP) | 1 | Gastrointestinal | Motility | Gastrointestinal |
| ·Class III | | | | | |
| | ·Metabotropic Glutamate | 7 | Brain | Sensory Perception | Hearing, Vision |
| | ·GABA$_B$ | 1 | Brain | Neurotransmitter | Mood Disorders |
| | ·Extracellular Calcium Sensing | 1 | Parathyroid, Kidney, GI Tract | Calcium Regulation | Cataracts, GI Tumors |

FIG. 11D

G protein-coupled receptors:
(Division into Class A
Or Class B)

1. A1 adenosine receptor [Homo sapiens]. ACCESSION AAB25533
   npivyaf riqkfrvtfl kiwndhfrcq pappidedlp eerpdd
   Class A 2. adrenergic, alpha -1B-, receptor [Homo sapiens]. ACCESSION NP_000670
   npiiypcsskefkrafvrilgcqcrgrgrrrrrrrrrlggcaytyrpwtrggslersqsrkdslddsgsclsgsqrtlpsaspspgylgr
   gapppvelcafpewkapgallslpapeppgrrgrhdsgplftfklltepespgtdggasnggceaaadvangqpgfksnmpla
   pgqf
   Class A 3. adrenergic receptor alpha-2A [Homo sapiens]. ACCESSION AAG00447
   npviytifnhdfrrafkkilcrgdrkriv
   Class A 4. alpha-2B-adrenergic receptor - human. ACCESSION A37223
   npviytifnqdfrrafrrilcrpwtqtaw
   Class A 5. alpha-2C-adrenergic receptor - human. ACCESSION A31237
   npviytvfnqdfrpsfkhilfrrrrrgfrq
   Class A 6. beta-1-adrenergic receptor [Homo sapiens]. ACCESSION NP_000675
   npiiycrspdfrkafqgllccarraarrrhathgdrprasgclarpgpppspgaasdddddddvvgatpparllepwagcnggaa
   adsd ssldepcrpgfaseskv
   Class A 7. beta-2 adrenergic receptor. ACCESSION P07550
   npliycrspdfriafqellclrrsslkaygngyssngntgeqsgyhveqekenkllcedlpgtedfvghqgtvpsdnidsqgrncs
   tndsll
   Class A 8. dopamine receptor D1 [Homo sapiens]. ACCESSION NP_000785
   npiiyafnadfrkafstllgcyrlcpatnnaietvsinnngaamfsshheprgsiskecnlvyliphavgssedlkkeeaagiarpl
   eklspalsvildydtdvslekiqpitqngqhpt
   Class A 9. D(2) dopamine receptor. ACCESSION P14416
   npiiyttfniefrkaflkilhc
   Class A

FIG. 11E 10. d3 dopamine receptor - human. ACCESSION G01977
npviyttfniefrkaflkilsc
   Class A 11. dopamine receptor D4 - human. ACCESSION DYHUD4
npviytvfnaefrnvfrkalracc
   Class A 12. dopamine receptor D5 - human. ACCESSION DYHUD5
npviyafnadfqkvfaqllgcshfcsrtpvetvnisnelisynqdivflhkeiaaayihmmpnavtpgnrevdndeeegpfdrm
fqiyqtspdgdpvaesvweldcegeisldkitpftpngfh
   Class A 13. muscarinic acetylcholine receptor M1 [Homo sapiens]. ACCESSION NP_000729
npmcyalcnkafrdtfrllllcrwdkrrwrkipkrpgsvhrtpsrqc
   Class A 14. muscarinic acetylcholine receptor M2 [Homo sapiens]. ACCESSION NP_000730
npacyalcnatfkktfkhllmchyknigatr
   Class A 15. muscarinic acetylcholine receptor M3 [Homo sapiens].
npvcyalcnktfrttfkmlllcqcdkkkrrkqqyqqrqsvifhkrapeqal
   Class A 16. muscarinic acetylcholine receptor M4 [Homo sapiens]. ACCESSION NP_000732
npacyalcnatfkktfrhlllcqyrnigtar
   Class A 17. m5 muscarinic receptor. locus HUMACHRM ACCESSION AAA51569
npicyalcnrtfrktfkmlllcrwkkkkveeklywqgnsklp
   Class A 18. 5-hydroxytryptamine (serotonin) receptor 1A [Homo sapiens]. ACCESSION
BAA90449
npviyayfnkdfqnafkkiikckf
   Class A 19. 5-hydroxytryptamine (serotonin) receptor 1B [Homo sapiens]. ACCESSION
BAA94455
npiiytmsnedfkqafhklirfkcts
   Class A

FIG. 11F 20. 5-hydroxytryptamine (serotonin) receptor 1E [Homo sapiens]. ACCESSION BAA94458
npllytsfnedfklafkklircre
Class A 21. OLFACTORY RECEPTOR 6A1. ACCESSION O95222
npiiyclrnqevkralccilhlyqhqdpdpkkgsrnv
Class A 22. OLFACTORY RECEPTOR 2C1. ACCESSION O95371
npliytlrnmevkgalrrllgkgrevg
Class A 23. angiotensin receptor 1 [Homo sapiens]. ACCESSION NP_033611
nplfygflgkkfkryflqllkyippkakshsnlsfkmstlsyrpsdnvssstkkpapcfeve
Class B 24. angiotensin receptor 2 [Homo sapiens]. ACCESSION NP_000677
npflycfvgnrfqqklrsvfrvpitwlqgkresmscrkssslremetfvs
Class B 25. interleukin 8 receptor beta (CXCR2) [Homo sapiens]. ACCESSION NM_001557
NPLIYAFIGQKFRHGLLKILAIHGLISKDSLPKDSRPSFVGSSSGHTSTTL
Class B 26. cx3c chemokine receptor 1 (cx3cr1) (fractalkine receptor) ACCESSION P49238
npliyafagekfrrylyhlygkclavlcgrsvhvdfsssesqrsrhgsvlssnftyhtsdgdallll
Class B 27. neurotensin receptor - human. ACCESSION S29506
n pilynlvsanfrhiflatlaclcpvwrrrrkrpafsrkadsvssnhtlssnatretly
Class B 28. SUBSTANCE-P RECEPTOR (SPR) (NK-1 RECEPTOR) (NK-1R). ACCESSION P25103
npiiycclndrfrlgfkhafrccpfisagdyeglemkstrylqtqgsvykvsrlettistvvgaheeepedgpkafpssldltsncssrsdskt mtesfsfssnvls
Class B 29. vasopressin receptor type 2 [Homo sapiens]. ACCESSION AAD16444
npwiyasfsssvsselrsllccargrtppslgpqdescttassslakdtss
Class B 30. thyrotropin-releasing hormone receptor - human. ACCESSION JN0708
npviynlmsqkfraafrklcnckqkptekpanysvalnysvikesdhfstelddittvtdtylsatkvsfddtclasevsfsqs
Class B

FIG. 11G

31. oxytocin receptor - human. ACCESSION A55493
    npwiymlftghlfhelvqrflccsasylkgrrlgetsaskksnsssfvlshrsssqrscsqpsta
    Class B 32. neuromedin U receptor 1 [Homo sapiens]. ACCESSION AAG24793
    npvlyslmssrfretfqealclgacchrlrprhsshslsrmttgstlcdvgslgswvhplagndgpeaqqetdps
    Class B 33. gastrin receptor. ACCESSION AAC37528
    nplvycfmhrrfrqacletcarccprpprarpralpdedpptpsiaslsrlsyttistlgpg
    Class B 34. galanin receptor 3 [Homo sapiens]. ACCESSION 10879541
    nplvyalasrhfrarfrrlwpcgrrrhrarralrrvrpassgppgcpgdarpsgrllagggqgpepregpvhggeaargpe
    Class A 35. edg-1 - human. ACCESSION A35300
    npiiytltnkemrrafirimscckcpsgdsagkfkrpiiagmefsrsksdnsshpqkdegdnpetimssgnvnsss
    Class A 36. central cannabinoid receptor [Homo sapiens]. ACCESSION NP_057167
    npiiyalrskdlrhafrsmfpscegtaqpldnsmgdsdclhkhannaasvhraaescikstvkiakvtmsvstdtsaeal
    Class A 37. delta opioid receptor - human. ACCESSION I38532
    npvlyafldenfkrcfrqlcrkpcgrpdpssfsrpreatarervtactpsdgpggggraa
    Class A 38. proteinase activated receptor 2 (PAR-2) human. ACCESSION P55085
    dpfvyyfvshdfrdhaknallcrsvrtvkqmqvsltskkhsrksssyssssttvktsy
    Class B 39. vasopressive intestinal peptide receptor (VIPR) rat. ACCESSION NM_012685
    NGEVQAELRRKWRRWHLQGVLGWSSKSQHPWGGSNGATCSTQVSMLTRVSPSA
    RRSSSFQAEVSLV
    Class B

MODIFIED TRAFFICKING PATTERNS FOR ARRESTIN AND G-PROTEIN-COUPLED RECEPTORS VIA ARRESTIN-UBIQUITIN CHIMERA This application is a U.S. National Phase of International Application No PCT/US04/02029, filed Jan. 6, 2004 and claims priority to U.S. Ser. No. 60/442,403 filed on Jan. 24, 2003, the contents of both of which are incorporated by reference in their entirety.

This work was supported by National Institutes of Health Grant 2R01 HL16037 and therefore the government may have certain rights to the invention.

FIELD OF THE INVENTION

The present invention relates to modified arrestins and arrestin chimeras. The arrestin chimeras of the present invention include arrestins that have been modified by ubiquitination, that is, the addition of an ubiquitin molecule or moiety to the arrestin. The arrestin chimeras can be modified by addition of a label molecule to the ubiquitinated arrestin. The invention also relates to methods of detecting G-protein-coupled receptor (GPCR) activity and methods of assaying GPCR activity using the arrestin chimeras and the modified arresting. The present invention also provides methods for identifying compounds that interact with the components of the GPCR regulatory pathway and methods for identifying ligands of GPCR's.

BACKGROUND OF THE INVENTION

G protein-coupled receptors (GPCRs) are cell surface proteins that translate hormone or ligand binding into intracellular signals. GPCRs are found in all animals, insects, and plants. GPCR signaling plays a pivotal role in regulating various physiological functions including phototransduction, olfaction, neurotransmission, vascular tone, cardiac output, digestion, pain, and fluid and electrolyte balance. Although they are involved in various physiological functions, GPCRs share a number of common structural features. They contain seven membrane domains bridged by alternating intracellular and extracellular loops and an intracellular carboxyl-terminal tail of variable length.

The magnitude of the physiological responses controlled by GPCRs is linked to the balance between GPCR signaling and signal termination. The signaling of GPCRs is controlled by a family of intracellular proteins called arrestins. Arrestins bind GPCRs, including those that have been agonist activated and bind more tightly to those that have been phosphorylated by G protein-coupled receptor kinases (GRKs) than those that are not.

Receptors, including GPCRs, have historically been targets for drug discovery and therapeutic agents because they bind ligands, hormones, and drugs with high specificity. Approximately fifty percent of the therapeutic drugs in use today target or interact directly with GPCRs. See e.g., Jurgen Drews, (2000) "Drug Discovery: A Historical Perspective," *Science* 287:1960-1964.

Although only several hundred human GPCRs are known, it is estimated that more than a thousand GPCRs exist in the human genome. Of these known GPCRs, many are orphan receptors that have yet to be associated with a function or specific ligands.

There is a continuing need for increasingly more accurate, easy to interpret methods of detecting G protein-coupled receptor activity and methods of assaying GPCR activity. One method, as disclosed in Barak et al., U.S. Pat. Nos. 5,891,646 and 6,110,693, uses a cell expressing a GPCR and a conjugate of an arrestin and a label molecule, the contents of which patents are incorporated by reference in their entirety.

In some instances, naturally occurring GPCRs do not provide optimal conditions for association with arrestin for easy detection. Accordingly, for those receptors that do not exhibit optimal conditions for association with arrestin, there is a need to increase affinity of the naturally occurring GPCRs with arrestin to provide for a more sensitive assay. Two distinct patterns of arrestin trafficking within the cell have been delineated resulting in the classification of GPCRs as follows: Class A (e.g. β2AR, α1b adrenergic receptor, μ opioid receptor, endothelin1A and dopamine D1A receptors) where arrestin interacts with the receptor at the cell surface but does not endocytose into vesicles, thus showing a transient interaction with the receptor, and class B (e.g. V2R, angiotensin AT1a, neurotensin1, thyrotropin releasing hormone and neurokinin NK-1 receptors) in which β-arrestins and receptor traffic together from the cell membrane to endocytic vesicles. These two classes of receptors also differ with regard to their affinity for different arrestin isoforms. In addition, Class A receptors preferentially bind β-arrestin2 whereas class B receptors bind to β-arrestin1 and β-arrestin2 with equal affinity.

β-arrestin-binding leads to the uncoupling of the receptor from its cognate G-proteins, causing dampening or desensitization of GPCR signaling via the downstream second messenger molecules. Recently, novel adaptor and scaffold functions of arrestins have been discovered. Thus, while terminating G-protein signals, arrestin binding can initiate new signalwaves from GPCRs. For example, β-arrestins serve as adaptors, which bring nonreceptor tyrosine kinases such as Src, to form signaling complexes with the internalizing receptor. β-arrestins function as GPCR-regulated scaffolds for MAPK modules such as ASK-MKK4-JNK3 and RAF-MEKERKI/2. In addition, arrestins interact with proteins of the endocytic machinery, such as clathrin, β-adaptin subunit2 of the AP2 complex, and Arf-6 and thus promote internalization of receptors via clathrin-coated vesicles.

Ubiquitination, in vivo, is a post-translational attachment of one or more ubiquitin molecules to the lysines of substrate proteins has been implicated to play a role in the internalization of yeast pheromone receptors and in the endocytosis of several mammalian cell-surface receptors. The prototypic mammalian GPCR, β2AR is also ubiquitinated in an agonist and β-arrestin-dependent manner. It appears that receptor ubiquitination is not crucial for its internalization but is essential for proper trafficking to lysosomes for degradation. On the other hand, β2AR internalization requires the agonist promoted ubiquitin modification of the adaptor protein β-arrestin2 catalyzed by a RING domain containing E3-ubiquitin ligase Mdm2.

Ubiquitin is a 76-amino acid residue monomeric protein so named because it is abundant in all eukaryotes and very highly conserved from yeast to humans. There are very few amino acid residue differences from species to species in the various ubiquitins in nature. Ubiquitin is normally associated with the degradation pathway of cytosolic proteins in proteosomes. The covalent binding of ubiquitin to a protein is normally the first step in marking a protein for degradation. Ubiquitination of a protein occurs by an energy dependent process that transfers ubiquitin from an ubiquitin-protein ligase (E3) to the ε-amino group of a lysine on the target protein. Normally, the isopeptide bond formed between the lysine of a protein to be degraded and ubiquitin can be removed by appropriate peptidases. Polyubiquitin chains can often form on a protein via isopeptide bonds at a Lys (usually LYS 48) of ubiquitin and the C-terminal carboxyl group of the following ubiquitin. Additionally, attachment of ubiquitin at LYS 63 of ubiquitin is implicated to play a role in ubiquitin dependant endocytosis. It is clear therefore; that it would be useful to improve the binding of arrestin to a GPCR in order to improve the arrestin mediated detection of activated or inhibited GPCRs and in one embodiment that GPCR would be a Class A GPCR. In U.S. Ser. No. 09/993,844 incorporated herein by reference, a method of improving the binding affinity of arrestin and a GPCR is disclosed involving modifying the GPCR by genetically changing the sequence of the carboxy terminal tail of the GPCR to include a higher number of phosphorylation sites. This is an extremely useful technique but does require the modification of each GPCR requiring improved binding affinity and such modification are not ideal because they have the potential to change the ligand binding properties of the receptor.

Therefore, in view of the aforementioned deficiencies attendant with prior art methods of detecting G protein-coupled receptor activity, it should be apparent that there still exists a need in the art for methods to improving the binding affinity of arrestin to GPCRs without the need to make modifications to each individual GPCR.

SUMMARY OF THE INVENTION

The present invention relates to a modified arrestins as defined herein. The modified arrestin will have both an ubiquitin moiety and a label molecule attached to arrestin. The ubiquitin moiety can be permanently fixed or can be attached with a desired level of affinity such that it is either permanently ubiquitinated or can be accessible for deubiquitination by attachment to a LYS. The invention also relates to arrestin and ubiquitin that are expressed as a chimera linked via an amide bond at the 5' end of one protein to the 3' end of the other.

The present invention further relates to the polypeptide sequences of modified arrestins, the nucleic acid sequences encoding modified arrestins, expression vectors comprising the nucleic acid sequence encoding a modified arrestin operably linked to an expression control sequence, and host cells expressing one or more modified arrestins of the present invention.

The modified arrestins of the present invention include arrestins that have been modified to have one or more sites of ubiquitination. It also includes chains of 2 or more ubiquitin molecules attached to an arrestin. The modified arrestins of the present invention have an increased affinity for GPCRs, especially for Class A GPCR's. This increased affinity for GPCRs improves their performance in assays that monitor GPCR activity. These modified arrestins are constructed such that the ubiquitination is properly positioned on the arrestin molecule to enhance the modified arrestins' affinity for GPCRs.

In another aspect, the present invention extends to arrestins that have an increased affinity to GPCRs. By increased affinity, the arrestin of the present invention remains associated with the GPCRs and traffics with the receptor into endosomes, as opposed to dissociating at or near the plasma membrane.

The present invention relates to all members of the herein disclosed arrestin family.

The modified arrestins of the present invention include arrestins with ubiquitin or an active fragment thereof ligated together to obtain an arrestin ubiquitin chimera. The modified arrestin is then made by attaching a label molecule to the arrestin-ubiquitin chimera. Both the arrestin and the ubiquitin may include one or more additions, substitutions, mutations, or deletions of amino acid residues. The ubiquitin is located at the 5' or 3' end of the expressed arrestin. Exemplary DNA sequences of the modified arrestin is show in FIGS. 8, 9, and 10.

An additional aspect of the present invention is a host cell that expresses at least one modified arrestin of the present invention. The host cell may also contain one or more expressed GPCRs. The host cell may be a mammalian, bacterial, yeast, fungal, plant, insect, or animal cell, and may be deposited on a substrate.

A further aspect of the present invention is a substrate having deposited thereon a plurality of cells that express at least one modified arrestin of the present invention. The host cells deposited on the substrate may also express one or more GPCRs.

A further aspect of the present invention is a method of screening compounds and sample solutions for GPCR agonist, antagonist, inverse agonist, or desensitization activity. Compounds and sample solutions may be screened by a method comprising using a modified arrestin of the present invention. Preferably, a cell is provided that expresses at least one modified arrestin of the present invention and that further comprises expression of one or more GPCRs. The sample compounds or sample solutions are provided and the cells are exposed to the sample compounds or solutions. Interaction of the modified arrestin protein with the GPCR along the translocation pathway is detected. In the methods of the present invention, the GPCRs may also be conjugated with a label molecule.

An additional aspect of the present invention is a method for identifying ligands of GPCRs. Such ligands may be natural or synthetic agonists or antagonists, and serve to modulate the activity of the GPCR. GPCRs have been implicated in a number of disease states, which are detailed below, and as such, modulation of GPCR activity is useful in the amelioration of effects of those diseases. Likewise, also included in the invention are the compounds identified by the methods.

Another aspect of the invention relates to methods of treating a human or non-human subject suffering from a GPCR-related disease. Such treatment can be performed either by administering to a subject in need of such treatment, an amount of the agonists or antagonists identified by the present method sufficient to treat the GPCR-related disease, or at least to lessen the symptoms thereof. Treatment may also be effected by administering to the subject the naked modified nucleic acid sequences of the invention, such as by direct injection, microprojectile bombardment, delivery via liposomes or other vesicles, or by means of a vector that can be administered by one of the foregoing methods. Gene delivery in this manner may be considered gene therapy.

Yet another aspect of the invention relates to methods of diagnosing a GPCR-related dysfunction or disorder in a human or non-human subject using the modified arrestin of the present invention. Such diagnosis may be performed using a molecule capable of detecting a GPCR or the nucleic acid encoding the GPCR in a sample from a subject. Such molecules include ligands. In addition, nucleic acid probes may be used to detect the sequences encoding a GPCR in a subject, such that alterations in the sequence thereof may be correlated with a dysfunction or disorder.

The present invention also relates to a recombinant DNA molecule or cloned gene, or a degenerate variant thereof, which encodes a modified arrestin of the invention. The nucleic acid molecule, in particular a recombinant DNA molecule or cloned gene, encoding the modified arrestin may have a nucleotide sequence or may be complementary to a DNA sequence shown in FIG. 8, 9, or 10 (SEQ ID NOS:1-2).

The present invention also includes modified arrestins having the activities noted herein, and that display the amino acid sequences set forth and described above and selected from SEQ ID NOS: 2, 4 and 6.

In a further embodiment of the invention, the full DNA sequence of the recombinant DNA molecule or cloned gene so determined may be operatively linked to an expression control sequence that may be introduced into an appropriate host. The invention accordingly extends to unicellular hosts transformed with the cloned gene or recombinant DNA molecule comprising a DNA sequence encoding the present modified arrestins, and more particularly, the complete DNA sequence determined from the sequences set forth above and in SEQ ID NOS: 1, 3 and 5.

According to other features of certain embodiments of the present invention, a recombinant expression system is provided to produce biologically active animal or human modified arrestins.

The concept of the modified arrestins contemplates that specific factors exist for binding to specific GPCRs with improved affinity especially for Class A GPCRs. Accordingly, the exact structure of each arrestin will understandably vary so as to achieve this desired level of affinity.

In addition to identifying agonists and antagonists of the GPCR to which the modified arrestin has affinity for, the present method can also be used for identifying compounds that target membrane-bound proteins, such as GPCRs, to endosomes. Likewise, the method can be used to detect GPCRs with altered endosome targeting, and for detecting endosome-related disease states.

In another aspect of the invention, the modified arrestin may be used for delivering a molecule or drug into a cell, by binding of the modified arrestin to a GPCR where the molecule or drug binds to the ligand-binding portion of the GPCR, followed by endocytosis of the GPCR-drug-modified arrestin complex.

The present invention naturally contemplates several means for preparation of the modified arresting, including as illustrated herein known recombinant techniques, and the invention is accordingly intended to cover such synthetic preparations within its scope. The isolation of the cDNA and amino acid sequences disclosed herein facilitates the reproduction of the modified arrestins by such recombinant techniques, and accordingly, the invention extends to expression vectors prepared from the disclosed DNA sequences for expression in host systems by recombinant DNA techniques, and to the resulting transformed hosts.

The invention includes an assay system for screening of potential drugs effective to modulate GPCR activity of target mammalian cells by interrupting or potentiating the action of the GPCR subsequent to ligand binding. In one instance, the test drug could be administered to a cellular sample with the ligand that activates GPCRs, or an extract containing the GPCR.

The assay system could more importantly be adapted to identify drugs or other entities that are capable of binding to a GPCRs, either at the plasma membrane or in the cytoplasm, thereby inhibiting or potentiating GPCR activity. Such assay would be useful in the development of drugs that would be specific against particular cellular activity, or that would potentiate such activity, in time or in level of activity.

In yet a further embodiment, the invention contemplates antagonists of the activity of a GPCR. In particular, an agent or molecule that inhibits interaction with a G protein or subsequent activation of second messengers. The diagnostic utility of the present invention extends to the use of the present modified arrestins in assays to screen for drugs suitable to treat GPCR related diseases.

The present invention includes an assay system that may be prepared in the form of a test kit for the quantitative analysis of the extent of the presence of a GPCR, and for analysis of the affinity for modified arrestin thereof, or to identify drugs or other agents that modulate their activity. The system or test kit may comprise a label molecule component prepared by one of the radioactive and/or enzymatic techniques discussed herein or any other label molecule as desired, coupling a label to the GPCR, their agonists and/or antagonists, or antibodies thereto, and one or more additional immunochemical reagents, at least one of which is a free or immobilized ligand, capable either of binding with the labeled component, its binding partner, one of the components to be determined or their binding partner(s).

In yet another embodiment, the present invention relates to certain therapeutic methods which would be based upon the activity of the GPCR(s), its (or their) subunits, or active fragments thereof, or upon agents or other drugs determined to possess the same activity to which the modified arrestin binds. A first therapeutic method is associated with the prevention of the manifestations of conditions causally related to or following from the binding activity of the GPCR or its subunits, and comprising administering an agent capable of modulating the production and/or activity of the GPCR or fragments thereof, either individually or in mixture with each other in an amount effective to prevent the development of those conditions in the host. For example, drugs or other binding partners to the GPCR or proteins may be administered to inhibit or potentiate GPCR activity. Also, the blockade of the action of specific kinases and/or phosphates in the GPCR-associated cascade of reactions presents a method for potentiating the activity of the GPCR that would concomitantly potentiate therapies based on GPCR activation.

More specifically, the therapeutic method generally referred to herein could include the method for the treatment of various pathologies or other cellular dysfunctions and derangements by the administration of pharmaceutical compositions that may comprise effective inhibitors or enhancers of activation of the GPCR or its subunits or fragments, or other equally effective drugs developed for instance by a drug screening assay prepared and used in accordance with a further aspect of the present invention. For example, drugs or other binding partners to the GPCR to which the modified arrestin binds, may be administered to inhibit or potentiate GPCR activity. Also, the blockade of the action of specific kinases or phosphates in the phosphorylation cascade of the GPCR presents a method for modulating the activity of the GPCR that would concomitantly potentiate therapies based on GPCR activation.

Accordingly, it is a principal object of the present invention to provide a modified arrestin and its subunits in purified form that exhibits certain characteristics and activities associated with GPCR binding to a ligand.

It is a further object of the present invention to provide agonists, antagonists, and antibodies to GPCRs and its subunits, and methods for their preparation, including recombinant means.

It is a further object of the present invention to provide a method for detecting the presence of a GPCR, and its subunits using a modified arrestin in mammals in which invasive, spontaneous, or idiopathic pathological states are suspected to be present.

It is a further object of the present invention to provide a method and associated assay system for screening substances such as drugs, agents and the like, potentially effective in either mimicking the activity or combating the adverse effects of a GPCR binding to ligands in mammals.

It is a still further object of the present invention to provide a method to control the amount or activity of a GPCR, especially a Class A GPCR, so as to treat or avert the adverse consequences of invasive, spontaneous or idiopathic pathological states.

It is a still further object of the present invention to provide pharmaceutical compositions for use in therapeutic methods which comprise or are based upon the modified arrestin which binds to a GPCR.

It is a further object of this invention to provide modified arrestins that have a greater affinity for GPCRs than non-modified arrestin.

It is still further an object of this invention to provide modified arrestins that have an improved affinity for Class A GPCRs.

It is even further an object of this invention to provide modified arrestins that bind to Class A GPCRs wherein the bound complex internalizes into endosomes.

Other objects and advantages will become apparent to those skilled in the art from a review of the ensuing description that proceeds with reference to the following illustrative drawings.

BRIEF DESCRIPTION OF THE DRAWINGS

FIG. 1 β-arrestin ubiquitination and deubiquitination parallel its association with and dissociation from GPCR Endogenous β2AR (A) or over expressed V2R (B) in COS-7 cells were stimulated with the agonist 10 μM isoproterenol (Iso) or 1 μM AVP for the indicated times and over expressed β-arrestin2Flag was immunoprecipitated with anti-FLAG beads and the IP probed for ubiquitinated forms using Ub antibody (Santa Cruz). HRP linked mouse IgG (Amersham) was used as the secondary antibody. Unmodified β-arrestin-flag has a mobility of approximately 51 kDa. The monoubiquitinated band of β-arrestin (~60 kDa) is indicated in both cases. The blots are representative of three independent experiments. C) Isoproterenol stimulated trafficking of β-arrestin2-GFP. βarrestin2-GFP and HAβ2AR were co-expressed in HEK293 cells. After stimulation or not with I μM isoproterenol, cells were fixed using paraformaldehyde. HA epitope was stained with a monoclonal antibody, 12CA5, followed by a secondary antibody to mouse IgG conjugated to Texas Red. The proteins were visualized by confocal microscopy, βarrestin (green channel), β2AR (red channel). Colocalization of the two proteins is seen in the overlay panels. The images are representative of three similar experiments. D) AVP stimulated trafficking of GFP-β-arrestin2. β-arrestin2-GFP and HAV2R were co-expressed in HEK293 cells. After stimulation or not with 1 μM arginine-vassopressin (AVP) cells were fixed using paraformaldehyde.

Figure 3B:
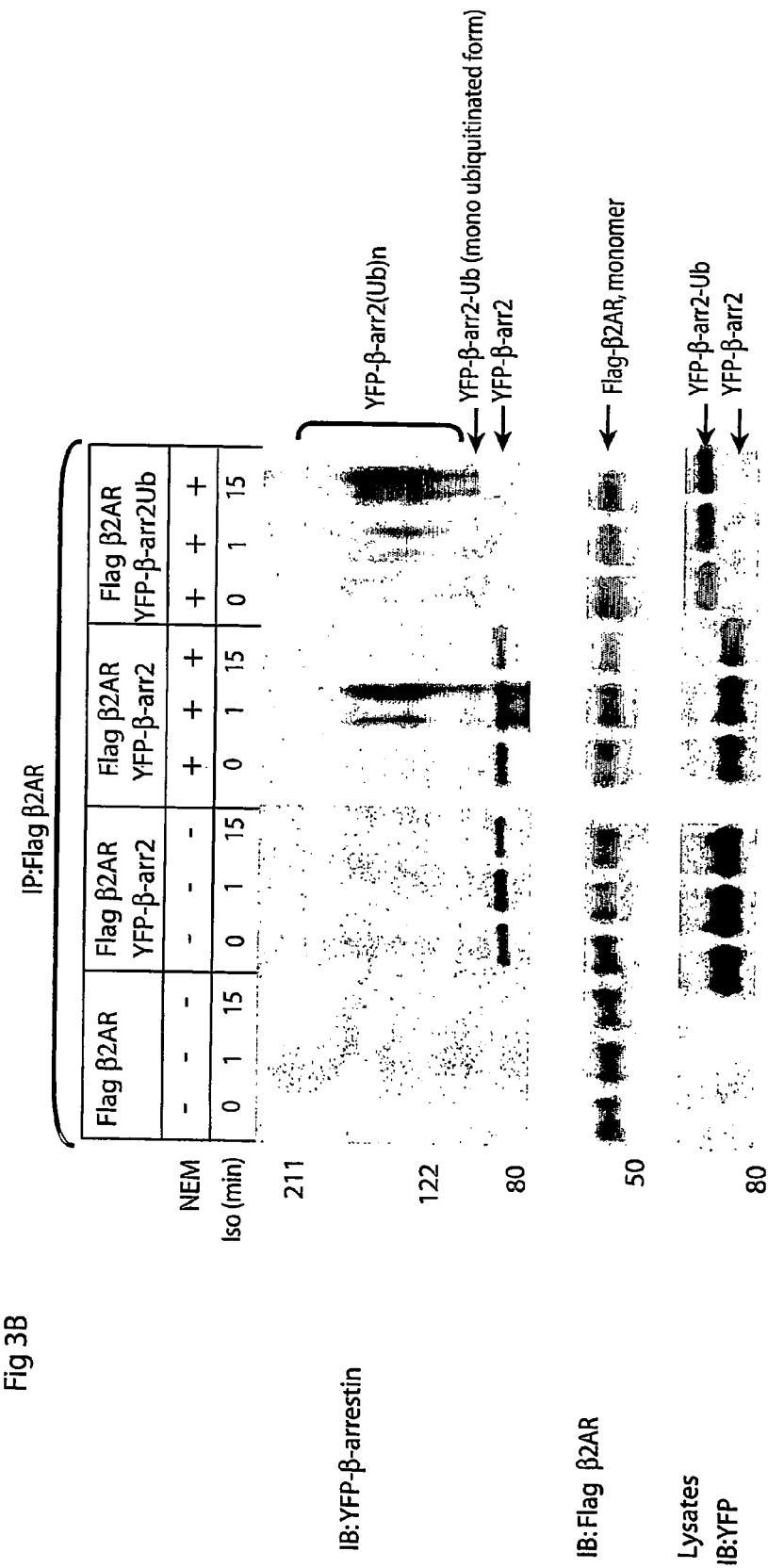

Antibody staining and protein visualization was following the same procedure as in (C).

FIG. 2 The GPCR tail-residues govern both trafficking and ubiquitination patterns of β-arrestin2 Trafficking of GFP-β-arrestin2 with the chimeric GPCRs β2ARV2CT (A) and V2Rβ2CT (B). HEK-293 cells were transiently transfected with β-arrestin2-GFP and HA-tagged receptor. After agonist treatment or not, cells were fixed, permeabilized and stained with 12CA5 and Texas Red conjugated antimouse antibody. Shown are confocal images of receptor immunofluorescence, (red) and β-arrestin-GFP fluorescence (green). Colocalization of β-arrestin and receptor is seen (yellow) in the overlay. Confocal images are representative of three similar experiments. C) β2ARV2CT dependent β-arrestin ubiquitination. COS-7 cells over expressing β2ARV2CT and β-arrestin2Flag were stimulated or not with 10 μM isoproterenol for the indicated times and β-arrestin was immunoprecipitated with anti FLAG affinity beads. The IP was probed with Ub antibody to detect ubiquitinated forms of β-arrestin. The blot is representative of three independent experiments. D) Time course of β-arrestin ubiquitination dependent on V2Rβ2CT stimulation. COS-7 cells over expressing V2R (β2CT and β-arrestin2Flag were stimulated or not with 1 μM AVP. β-arrestin was immunoprecipitated and the IP was probed with Ub antibody. The "blot is representative of three independent experiments.

FIG. 3 Characterization of YFP-β-arrestin-Ub chimeric protein

A) Stability of the ubiquitin chimera in COS-7 cells. Over expressed YFP-β-arrestin2 or YFP-β-arrestin2-Ub was immunoprecipitated with GFP-agarose beads or Al CT antibody beads as described in the "Methods" section. The bands on the autorad were quantitated using Fluorimager and graphically represented in the figure. The zero time point represents 100% protein. The graph is an average of three independent experiments. B) Interaction of β-arrestin2-Ub chimera with β2AR. Flag-β2AR was coexpressed with either YFP-β-arrestin2 or YFP-β-arrestin2-Ub in COS-7 cells. After stimulation or not the receptor was immunoprecipitated with anti-Flag beads in the absence (left panels) or presence (right panels) of the inhibitor NEM; the IP was blotted for YFP-β-arrestins with a monoclonal antibody to GFP (top panel). The middle panel shows the amount of receptor as detected by anti-flag antibody M2. The lower panel shows the expression levels of YFP-β-arrestins in whole-cell extracts as detected by the GFP-monoclonal antibody. The blots are representative of similar blots from three independent experiments.

FIG. 4 Intracellular trafficking patterns of YFP-β-arrestin and YFP-β-arrestin-Ub HEK-293 cells were transiently transfected with either YFP-β-arrestin2 or YFP-β-arrestin2-Ub along with β2AR (A) or V2Rβ2CT (B). Cells were starved for one hour in serum free media. The distribution of YFP-β-arrestin2 and YFP-β-arrestin2-Ub was visualized before and after treatment with 10 μM isoproterenol(A) or AVP (B). Shown are representative confocal images of YFP-fluorescence followed in the same HEK-293 cells treated for 2, 15 and 30 min at 37° C.

FIG. 5 YFP-9-arrestin2-Ub but not YFP-β-arrestin colocalizes in endocytic vesicles with β 2AR.

HEK-293 cells were transiently transfected with HA-β2AR and YFP-βarrestin2 (A) or YFP-β-arrestin2-Ub (B). After isoproterenol treatment or not the cells were fixed, permeabilized and stained for receptor with the primary antibody 12CA5 and secondary antibody anti mouse IgG conjugated to Texas Red. Shown are confocal images where receptor is visualized in the Red channels and β-arrestin in the green channels. Colocalization of two proteins is seen as yellow in the overlay. The results are representative of three independent experiments.

Figure 6A:
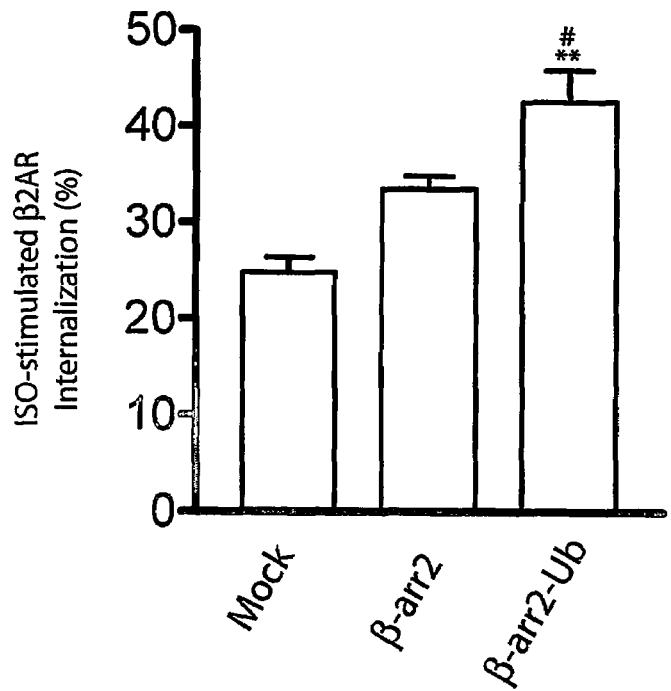

FIG. 6 Effect of chimeric a-arrestin-Ub on sequestration of GPCRs.

HEK-293 cells were transiently transfected with Flag-β2AR (A) and V2R (B). In each case the receptor was cotransfected with vector plasmid (mock), (β-arrestin2, or (β-arrestin2-Ub. After serum starvation cells were treated with 10 μM isoproterenol (A) or 1 μM AVP (B) for 30 minutes at 37° C. Cell-surface receptors before and after agonist treatment were determined by Flow cytometry. Data in (A) is the mean±SEM of seven independent experiments done in triplicate. Data in (B) is the mean±SEM of five independent experiments done in triplicate. # P<0.05 vs. β-arrestin2; ** P<0.001 vs. Mock, one way ANOVA, with Tukey multiple comparison.

FIG. 7 Effect of chimeric β-arrestin-Ub on degradation of GPCRs HEK-293 cells were transiently transfected with Flag-β2AR (A) and β2ARV2CT (B).

In each case the receptor was cotransfected with vector plasmid (mock), β-arrestin2, or β-arrestin2-Ub. After serum starvation cells were treated with 10 μM isoproterenol for 24 hours at 37° C. 125 I CYP binding was done on whole cells as described in the Methods section to determine the receptor numbers with and without agonist treatment. The results are the mean±SEM of 3-5 experiments. * P<0.01 vs Mock, # P<0.05 vs β-arr2, one way ANOVA with Tukey multiple comparison.

FIG. 8A-8B Amino acid and nucleic acid sequences of the EYFP-Barr2-Ub construct (SEQ ID NOS:1-2).

FIG. 9A-9B Amino acid and nucleic acid sequences of the EYFP-Barr2-Ub48 construct (SEQ ID NOS:3-4).

FIG. 10A-10B Amino acid and nucleic acid sequences of the EGFPBarr2Ub48 construct (SEQ ID NOS:5-6).

FIG. 11A-11G is an illustrative, non-limiting list of known receptors, including the amino acid sequence for their carboxyl terminal tails and appropriate classification. FIG. 11A lists receptors from the Human G Protein Coupled Receptor Family divided into Class I, Class II or Class III. FIG. 11B lists G-protein coupled receptors divided into Class A or Class B. For the Class B receptor examples, the residues that may function as clusters of phosphorylation sites are shown in bolded italics (SEQ ID NOS: 7-45).

DETAILED DESCRIPTION OF THE PREFERRED EMBODIMENTS

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (2000)]; "Immobilized Cells And Enzymes" [IRL Press, (1986)]; B. Perbal, "A Practical Guide To Molecular Cloning" (1984).

Unless otherwise stated, the following terms used in the specification and claims have the meanings given below:

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

A DNA "coding sequence" is a double-stranded DNA sequence that is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to a probe of the present invention, is defined as a molecule comprised of two or more ribonucleotides, preferably more than three. Its exact size will depend upon many factors that, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, noncomplementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

It should be appreciated that also within the scope of the present invention are DNA sequences encoding modified arrestins having the same amino acid sequence as arrestin or ubiquitin, but which are degenerate to another sequence. By "degenerate to" is meant that a different three-letter colon is used to specify a particular amino acid.

"Arrestin" means all types of naturally occurring and engineered variants of arrestin, including, but not limited to, visual arrestin (sometimes referred to as Arrestin 1), β-arrestin I (sometimes referred to as Arrestin 2), and β-arrestin 2 (sometimes referred to as Arrestin 3). Arrestin includes arrestin from all sources including mammals and humans.

By "Translocation pathway" is meant the trafficking patterns made by arrestin in response to the membrane receptor such as the GPCR. This includes movement within the cells of arrestin to and from the receptor as well as movement to other areas of the cells including to clathrin pits, in and to vesicles, to sites of degradation and the like.

"Class A receptor" means a GPCR that does not have one or more sites of phosphorylation, preferably clusters of phosphorylation sites, properly positioned in its carboxyl-terminal tail such that it does not recruit rat βarrestin-2 to endosomes in HEK-293 cells under conditions as described in U.S. Pat. No. 5,891,646 and Oakley, et al. "Differential Affinities of Visual Arrestin, βArrestin1, and (βArrestin2 for G Protein-coupled Receptors Delineate Two Major Classes of Receptors," *Journal of Biological Chemistry*, Vol 275, No. 22, pp 17201-17210, Jun. 2, 2000, the contents of which are hereby incorporated by reference in their entirety. Receptors are classified as Class B on the basis of their interactions with naturally-occurring rat β-arrestin 2 isoforms as described in the above, and may be predicted based on the amino acid residues in their carboxyl-terminal tails.

"Class B receptor" means a GPCR that has one or more sites of phosphorylation, preferably clusters of phosphorylation sites, properly positioned in its carboxyl-terminal tail such that it does recruit rat β-arrestin-2 to endosomes in HEK-293 cells under conditions as described in U.S. Pat. No. 5,891,646 and Oakley, et al. "Differential Affinities of Visual Arrestin, βArrestin1, and βArrestin2 for G Protein-coupled Receptors Delineate Two Major Classes of Receptors," *Journal of Biological Chemistry*, Vol 275, No. 22, pp 17201-17210, Jun. 2, 2000, the contents of which are hereby incorporated by reference in their entirety. Receptors are classified as Class B on the basis of their interactions with naturally-occurring rat β-arrestin 2 isoforms as described in the above, and may he predicted based on the amino acid residues in their carboxyl-terminal tails.

"DACs" mean any desensitization active compounds. Desensitization active compounds are any compounds that influence the GPCR desensitization mechanism by either stimulating or inhibiting the process. DACs influence the GPCR desensitization pathway by acting on any cellular component of the process, as well as any cellular structure implicated in the process, including but not limited to, arrestins, GRKs, GPCRs, AP-2 protein, clathrin, protein phosphatases, and the like. DACs may include, but are not limited to, compounds that inhibit arrestin translocating to a GPCR, compounds that inhibit arrestin binding to a GPCR, compounds that stimulate arrestin translocating to a GPCR, compounds that stimulate arrestin binding to a GPCR, compounds that inhibit GRK phosphorylation of a GPCR, compounds that stimulate GRK phosphorylation of a GPCR, compounds that inhibit protein phosphatase dephosphorylation of a GPCR, compounds that stimulate protein phosphatase dephosphorylation of a GPCR, compounds that regulate the release of arrestin from a GPCR, antagonists of a GPCR, inverse agonists and the like. DACs preferably inhibit or stimulate the GPCR desensitization process without binding to the same ligand-binding site of the GPCR as traditional agonists and antagonists of the GPCR. DACs act independently of the GPCR, i.e. they do not have high specificity for one particular GPCR or one particular type of GPCRs.

"Label molecule" means any detectable molecule capable of improved detection by spectroscopic, photochemical, biochemical, immunochemical, radiochemical, electrical, and optical means, including but not limited to, fluorescence, phosphorescence, radioactivity, and bioluminescence when compared with the detection of the molecule to which the label molecule is attached. In one embodiment, the label molecule makes detection of the moiety it is attached to, e.g. the arrestin ubiquitin complex, easier than without the label molecule. Label molecules include, but are not limited to GFP, YFP, luciferase, rhodamine-conjugated antibody, and the like.

In the instance where the label molecule is a radioactive label or marker of the arrestin is used, such as the isotopes $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re are used, known currently available counting procedures may be utilized. In the instance where the label molecule is an enzyme, detection may be accomplished by any of the presently utilized colorimetric, spectrophotometric, fluorospectrophotometric, amperometric or gasometric techniques known in the art.

"GFP" means Green Fluorescent Protein that refers to various naturally occurring forms of GFP that may be isolated from natural sources or genetically engineered, as well as artificially modified, GFPs. GFPs are well known in the art. See, for example, U.S. Pat. Nos. 5,625,048; 5,777,079; and 6,066,476. It is well understood in the art that GFP is readily interchangeable with other fluorescent proteins, isolated from natural sources or genetically engineered or modified, including but not limited to, yellow fluorescent proteins (YFP), red fluorescent proteins (RFP), cyan fluorescent proteins (CFP), UV excitable fluorescent proteins, or any wavelength in between regardless of whether in the visible spectrum or not.

By "arrestin chimera" is meant the expression product resulting from the chimeric expression of both arrestin and ubiquitin thus forming an arrestin ubiquitin or ubiquitin-arrestin chimera.

"Modified arrestin" means an arrestin that has one or more ubiquitin moieties and a label molecule associated or attached to the arrestin. Attachment or association can be by covalent, peptide or like bonds. It also includes one or more modifications in the amino acid sequence of the arrestin, label molecule or ubiquitin from wild type sequences or structures. Modifications in the amino acid sequence include mutations of one or more amino acids, insertion of one or more amino acids, deletion of one or more amino acids, and substitutions of one or more amino acids in which one or more amino acids are deleted and one or more amino acids are added in place of the deleted amino acids which do not substantially change its activity. By "ubiquitin moiety" is meant the active wild type or synthetic ubiquitin or active fragment or active extended sequence thereof. It further includes mutations to the amino acid sequence that conserves the ubiquitin activity although it may change the affinity of the molecule for the arrestin. It also includes multiple copies of ubiquitin directly attached to arrestin or other ubiquitin molecules or chain attached to other ubiquitin molecules. Polyubiquitin chains are normally formed by isopeptide bonds at a Lys position (frequently Lys 48) with the C-terminal carboxyl group of the following ubiquitin. Ability to form polyubiquitin chains can be accomplished by addition or subtraction of Lys in adjacent ubiquitin molecules. The ubiquitin moiety is attached to the arrestin in any convenient manner. In one embodiment the ubiquitin is attached to the arrestin such that normal removal by isopeptidases does not occur. This is essentially a permanent to semi-permanent attachment. In other embodiments the number and affinity of attachments by ubiquitin is varied by known means to give a desired rate of ubiquitin removal in vivo. Thus a desired cycling rate or attachment to a given GPCR can be achieved. The ubiquitin moiety that is selected is done so that the GPCR binds modified arrestin with sufficient and desired affinity to recruit modified arrestin bound to a GPCR into endosomes.

"Unknown or Orphan Receptor" means a GPCR whose function and/or ligands are unknown.

"Downstream" means toward a carboxyl-terminus of an amino acid sequence, with respect to the amino-terminus.

"Upstream" means toward an amino-terminus of an amino acid sequence, with respect to the carboxyl-terminus.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces βturns in the protein's structure. A LYS may be introduced as a specific ubiquitin binding site on either the arrestin or the label molecule.

Two amino acid sequences are "substantially homologous" when at least about 70% of the amino acid residues (preferably at least about 80%, and most preferably at least about 90 or 95%) are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce some feature of pathology such as for example, elevated blood pressure, respiratory output, etc.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well-known formulae, wherein hybridization is typically 10-20 C below the predicted or determined Tm with washes of higher stringency, if desired.

The present invention is related to modified arresting, polypeptides of modified arresting, nucleic acid molecules that encode the modified arresting, vectors containing the nucleic acid molecules that encode the modified arresting, vectors enabling the nucleic acid construction of the modified arresting, and cells containing modified arrestins. The invention further relates to assay systems using the modified arresting, assay systems using the cells containing modified arresting, compounds identified using the assay systems, methods of treatment using the compounds identified, methods of disease diagnosis using the assay systems, and kits containing assay reagents of the present invention and cells of the present invention. The invention also may relate to antisense and treatment techniques.

Mutations can be made in the modified arrestin such that a particular codon is changed to a codon that codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

In a particular embodiment, the modified arrestins of the present invention recruit GPCRs to endosomes within approximately 15 minutes of agonist stimulation.

The modified arrestins of the present invention comprise a conjugate of arrestin, an ubiquitin moiety and a label molecule. The present inventors have discovered that an arrestin-ubiquitin moiety complex have an increased affinity for GPCRs regardless of phosphorylation of the GPCR and colocalize in endosomes after stimulation with agonist. The present inventors have discovered that the modified arrestins of the present invention are useful in assays for screening compounds that may alter G protein-coupled receptor (GPCR) activity. Examples of assays in which the present invention may be used include, but are not limited to, those as described in U.S. Pat. Nos. 5,891,646 and 6,110,693, the disclosures of which are hereby incorporated by reference in their entireties. Additional examples of assays in which the present invention may be used include, but are not limited to, assays using Fluorescent Resonance Energy Transfer (FRET) and assays using Bioluminescence Resonance Energy Transfer (BRET) technology as described in Angers, S., Salahpour, A., Joly, E., Hilairet, S., Chelsky, "β-2 adrenergic receptor dimerization in living cells using bioluminescence resonance energy transfer (BRET)," *Proc. Natl. Acad. Sci. USA* 97, 7: 3684-3689.

By way of example, the present inventors have identified three major classes of GPCRs for known receptors: Class A receptors, Class B receptors, and receptors with virtually non-existent carboxyl-terminal tails. The receptors are classified accordingly based on their interactions with and affinity for rat β-arrestin-2 in HEK-293 cells as described above, and may be predicted based on the amino acid residues in their carboxyl-terminal tail and the length of their carboxyl-terminal tail. As defined above, Class B receptors have one or more sites of phosphorylation, preferably clusters of phosphorylation sites, properly positioned in their carboxyl-terminal tails such that they recruit rat β-arrestin-2 to endosomes in HEK-293 cells. Also as defined above, Class A receptors do not have one or more sites of phosphorylation, preferably clusters of phosphorylation sites, properly positioned in their carboxyl-terminal tails such that they do not recruit βarrestin-2 to endosomes in HEK-293 cells. Receptors with virtually nonexistent carboxyl-terminal tails include, for example, olfactory and taste receptors. In FIG. 11 is an illustrative, non-limiting list of known receptors, including the amino acid sequence for their carboxyl terminal tails and appropriate classification. For the Class B receptor examples, the residues that may function as clusters of phosphorylation sites are shown in bolded italics.

It has been discovered that after agonists bind and activate GPCRs, G protein-coupled receptor kinases (GRKs) phosphorylate clusters of serine and threonine residues located in the third intracellular loop or the carboxylterminal tail of the GPCRs. After phosphorylation, an arrestin protein associates with the GRK-phosphorylated receptor and uncouples the receptor from its cognate G protein. The interaction of the arrestin with the phosphorylated GPCR terminates GPCR signaling and produces a nonsignaling, desensitized receptor. Where no phosphorylation occurs or little occurs as in Class A receptors arrestin is not recruited to GPCRs in any significant amounts. In such cases the present invention is thus useful to bind to such a non-phosphorylated GPCR and recruit it to an endosome.

The present inventors have discovered that the stability of the interaction of arrestin with a GPCR is not solely dependant on the GPCR phosphorylation of the carboxy tail. When the modified arrestin has an enhanced affinity for a GPCR, the GPCR/arrestin complex is stable, remains intact and is internalized into endosomes. When the arrestin does not have an enhanced affinity for a GPCR, the GPCR/arrestin complex tends not to be stable and arrestin is not recruited into endosomes with the GPCR. Arrestins, which have an enhanced affinity for a GPCR and thus the GPCR/arrestin complex remains intact, recycle and resensitize slowly or in some cases where the ubiquitin is stably attached, not at all. In contrast, GPCRs that dissociate from arrestin at or near the plasma membrane recycle rapidly.

The present inventors have discovered that the ability of arrestin to remain associated with GPCRs can be increased by ubiquitination of the arrestin that is attaching an ubiquitin moiety to the arrestin prior to recruitment by a GPCR. Permanent attachment of the ubiquitin moiety leads to permanent desensitization of the particular GPCR. These modified arrestins may be useful in assaying GPCR activity.

GPCRs have been implicated in a number of disease states, including, but not limited to cardiac indications such as angina pectoris, essential hypertension, myocardial infarction, supraventricular and ventricular arrhythmias, congestive heart failure, atherosclerosis, renal failure, diabetes, respiratory indications such as asthma, chronic bronchitis, bronchospasm, emphysema, airway obstruction, upper respiratory indications such as rhinitis, seasonal allergies, inflammatory disease, inflammation in response to injury, rheumatoid arthritis, chronic inflammatory bowel disease, glaucoma, gastrointestinal indications such as acid/peptic disorder, erosive esophagitis, gastrointestinal hypersecretion, mastocytosis, gastrointestinal reflux, peptic ulcer, Zollinger-Ellison syndrome, pain, obesity, bulimia nervosa, depression, obsessive-compulsive disorder, neurodegenerative diseases such as Parkinson's Disease and Alzheimer's Disease, multiple sclerosis, Epstein-Barr infection and cancer. As such, modulation of arrestin binding is a mechanism for ameliorating these disease states.

Modified Arrestins

The present invention is related to modified arrestins. Modified arrestins of the present invention comprises the addition of an ubiquitin moiety bound or associated with arrestin. It also includes the attachment of a label molecule as a fusion protein or any other attachment method that allows the arrestin to remain active after attachment. The present inventors have determined that the addition of ubiquitin moieties to arrestin increases the affinity of arrestin to binding to a GPCR.

GPCRs that lack one or more sites of phosphorylation, preferably clusters of phosphorylation, properly positioned within the carboxyl terminal tail form GPCR/arrestin complexes that are less stable and dissociate at or near the plasma membrane. These GPCRs are typically Class A receptors, olfactory receptors, taste receptors, and the like. However, the present inventors have discovered that stable GPCR/arrestin complexes may be achieved with arrestins modified to include an ubiquitin moiety when expressed. In one embodiment the ubiquitin is attached such that it may not be deubiquitinated. In another embodiment multiple ubiquitin molecules are attached to the arrestin.

The present invention includes the polypeptide sequences of these modified arresting. The modified arrestins of the present invention include arrestins that have been modified to have one or more ubiquitin molecules and a label molecule bonded or associated thereto. The polypeptide sequences of the modified arrestins of the present invention also include sequences having one or more additions, deletions, substitutions, or mutations. These mutations are preferably substitution mutations made in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. The present invention should be considered to include sequences containing conservative changes which do not significantly alter the activity or binding characteristics of the resulting protein.

The present invention further includes isolated nucleic acid molecules that encode modified arrestins. It should be appreciated that also within the scope of the present invention are DNA sequences encoding modified arrestins which code for a modified arrestin having the same amino acid sequence as the modified arrestins, but which are degenerate. By "degenerate to" it is meant that a different three-letter codon is used to specify a particular amino acid.

By way of example, a Class A receptor or an orphan receptor will bind a modified arrestin similar to wild type arrestin binding Class B receptor. Further, receptors having virtually non-existent carboxyl-terminal tails, for example, olfactory receptors and taste receptors, will tightly bind the modified arresting.

Modified arrestins may be generated by molecular biological techniques standard in the genetic engineering art, including but not limited to, polymerase chain reaction (PCR), restriction enzymes, expression vectors, plasmids, and the like.

As may be shown by standard receptor binding assays, the modified arrestins are essentially indistinguishable from their wild-type counterparts except for an increased affinity for GPCRs and thus an increased stability of their complex with a GPCR and in their ability to traffic and in their decreased ability to recycle and resensitize. For example, the modified arrestins are appropriately expressed in the cytoplasm, and possess increased affinity for GPCRs without changing the GPCRs affinity for binding of agonists or ligands, and provide the appropriate downstream signaling in response to agonist activation. However, the modified arrestins have an increased affinity for GPCRs and thus form a more stable complex with GPCRs than their wildtype counterparts and may remain bound to GPCRs when trafficking to endosomes. They may even remain permanently bound to the GPCR thus removing the GPCR permanently from activity. It is also possible that these modified arrestins could thus be used to treat a disease state when less of a particular GPCR in circulation could reduce or ameliorate the disease symptoms.

The cells used in the methods of assaying of the present invention may comprise a modified arrestin. The modified arrestin comprises a conjugate of an arrestin-ubiquitin moiety chimera and a label molecule. In the cells and methods of the present invention, the cells may also comprise a GPCR or other membrane receptor compatible with arrestin.

All forms of arrestin, naturally occurring and engineered variants, including but not limited to, visual arrestin, β-arrestin 1 and β-arrestin 2, may be used in the present invention. The modified arrestins of the present invention may interact to a detectable level with all forms of GPCRs.

Label molecules that may be used to conjugate with the arrestin include, but are not limited to, molecules that are detectable by spectroscopic, photochemical, biochemical, immunochemical, electrical, radioactive, and optical means, including but not limited to bioluminescence, phosphorescence, and fluorescence. These label molecules should be a biologically compatible molecule and should not compromise the ability of the arrestin to interact with the GPCR system and the interaction of the arrestin with the GPCR system must not compromise the ability of the label molecule to be detected. One embodiment of label molecules are optically detectable molecules, including optically detectable proteins, such that they may be excited chemically, mechanically, electrically, or radioactively to emit fluorescence, phosphorescence, or bioluminescence. Other embodiments of label molecules are inherently fluorescent molecules, such as fluorescent proteins, including, for example, Green Fluorescent Protein (GFP). The label molecule may be conjugated to the arrestin protein by methods as described in Barak et al. (U.S. Pat. Nos. 5,891,646 and 6,110,693). The label molecule may be conjugated to the arrestin at the front-end, at the back-end, or in the middle. The label molecule could also be conjugated to the ubiquitin moiety.

When the arrestin chimera is conjugated with a label molecule, proximity of the GPCR with the arrestin chimera may be readily detected. In addition, if the arrestin chimera is conjugated with a label molecule, compartmentalization of the GPCR with the arrestin may be readily confirmed.

Another aspect of the present invention is a method for permanently attaching a ubiquitin molecule to a protein. In this method, the nucleic acid sequence encoding ubiquitin is added to the 5' or 3' of a nucleic acid sequence encoding the molecule of interest. Proteins in addition to arrestin may be modified in this manner.

Methods of Assaying GPCR Activity with Modified Arrestins

The modified arrestins of the present invention are useful in methods of assaying GPCR activity. The modified arrestins of the present invention may be used in assays to study GPCRs that have weaker than desired interactions or associations with arrestins and GPCRs that have unknown interactions or associations with arresting. Methods of the present invention that use the modified arrestins provide a sensitive assay and may provide for enhanced detection, for example, of arrestin/GPCRs in endosomes. The assays using the modified arrestins of the present invention may be useful for screening compounds and sample solutions for ligands, agonists, antagonists, inverse agonists, desensitization active compounds, and the like. Once identified, these compounds may be useful as drugs capable of modulating GPCR activity and useful in the treatment of one or more of the disease states in which GPCRs have been implicated.

In a preferred assay according to the present invention, cells are provided that express modified arrestins of the present invention and these cells may further contain an expressed GPCR.

An Arrestin-ubiquitin chimera coupled to a label molecule may be detected and monitored as it functions in the translocation pathway. The location of the modified arrestin may be detected, for example, evenly distributed in the cell cytoplasm, concentrated at a cell membrane, localized on endosomes, and the like. In response to agonist stimulation, the proximity of modified arrestin to a GPCR may be monitored, as well as the proximity to any other cell structure. For example, in response to agonist stimulation modified arrestin may be detected in proximity to GPCRs at a cell membrane, co-localized with a GPCR on endosomes, and the like.

The modified arrestins of the present invention have an increased affinity for GPCRs and provide a stable complex of the GPCR with the modified arrestin, and thereby promote colocalization of the GPCR with modified arrestin into endosomes. In the methods of assaying of the present invention, modified arrestin may be detected, for example, in the cytoplasm, concentrated in proximity to GPCRs at a cell membrane, concentrated in proximity to GPCRs, colocalized with a GPCR on endosomes, and the like. In one embodiment the modified arrestin may be detected colocalized with a GPCR on endosomes.

The association of modified arrestin with a GPCR at a cell membrane may be rapidly detected after agonist addition, for example, approximately 1 second to 2 minutes. The colocalization of modified arrestin with GPCR on endosomes may be detected within several minutes of agonist addition, for example, approximately 3 to 15 minutes, and may persist for extended periods of time, for example, after 1 hour. The association of modified arrestin with GPCR on endosomes may give a strong, readily recognizable signal. Under magnification of 40× objective lens, the signal may be doughnut-like in appearance. The signal resulting from the compartmentalization of arrestin and GPCR colocalized in endosomes vesicles is typically easy to detect and may persist for extended periods of time.

A method of assessing GPCR pathway activity of the present invention comprises (a) providing a cell that expresses at least one modified arrestin of the present invention and that further comprises a GPCR; (b) inducing translocation of the modified arrestin; and (c) detecting interaction of the modified arrestin with the GPCR along the translocation pathway.

Interaction of the modified arrestin with a GPCR may be detected, for example, in endosomes, concentrated in proximity to a cell membrane, and the like. Preferably, interaction of the modified arrestin with the GPCR is detected in endosomes. Interaction of modified arrestin with a GPCR in endosomes, may be detected within several minutes of agonist addition, for example, approximately 3 to 15 minutes, and may persist for extended periods of time, for example, after 1 hour. The association of modified arrestin with a GPCR in endosomes may give a strong, readily recognizable signal that persists for extended periods of time.

In a method of screening compounds for GPCR activity of the present invention a cell that expresses at least one modified arrestin is provided. The cell further expresses at least one GPCR. The cell is exposed to the compounds to be tested. The location of the modified arrestin within the cell is detected. The location of the modified arrestin within the cell in the presence of the compound is compared to the location of the modified arrestin within the cell in the absence of the compound, and a difference is correlated between (1) the location of the modified arrestin within the cell in the presence of the compound and (2) the presence of the location of the modified arrestin within the cell in the absence of the compound.

By way of example, compounds and sample solutions may be screened for GPCR agonist activity using the modified arrestins of the present invention. In this method, cells that express at least one GPCR and that further comprise a modified arrestin comprising a conjugate of an arrestin and ubiquitin bound to a label molecule are provided. The cells are exposed to compounds or sample solutions to be tested. It is detected whether interaction of the modified arrestin with the GPCR is increased after exposure to the test compound or solution, an increase in interaction being an indication that the compound or solution has GPCR agonist activity. Interaction of the modified arrestin with the GPCR may be detected in endosomes, in proximity to a cell membrane, and the like. The GPCR may also be conjugated to a label molecule, preferably at the carboxyl-terminus. Modifications to GPCRs should be chosen so as not to affect the GPCRs' natural affinity for agonists or ligands.

Also by way of example, compounds and sample solutions may be screened for GPCR antagonist or inverse agonist activity using the modified arrestins of the present invention. Cells that express at least one GPCR and that further comprise a modified arrestin comprising a conjugate of an arrestin and a ubiquitin moiety bound to a label molecule are provided. The cells are exposed to compounds or sample solutions to be tested and to a known agonist for the GPCR. It is detected whether interaction of the modified arrestin with the GPCR is decreased after exposure to the test compound or solution, a decrease in interaction being an indication that the compound or solution has GPCR antagonist or inverse agonist activity. Interaction of the modified arrestin with the GPCR may be detected in endosomes, in proximity to a cell membrane, and the like. The GPCR may also be conjugated to a label molecule, preferably at the carboxyl-terminus. As explained above, modifications to GPCRs should not affect the GPCRs' natural affinity for antagonists or inverse agonists.

Further by way of example, compounds and sample solutions may be screened for GPCR desensitization activity using the modified arrestins of the present invention. First cells that express at least one first GPCR and that further express a modified arrestin of the present invention comprising a conjugate of an arrestin and an ubiquitin bound to a label molecule are provided. The first cells are exposed to compounds or sample solutions to be tested and to a known agonist for the first GPCR. It is detected whether interaction of the modified arrestin with the first GPCR is decreased or not increased after exposure to the test compound or solution, a decrease or lack of increase in interaction being an indication that the compound or solution has GPCR desensitization activity. Interaction of the modified arrestin with the GPCR may be detected in endosomes, in proximity to a cell membrane, and the like. Then second cells that express at least one second GPCR and that further comprise a modified arrestin comprising a conjugate of an arrestin and a ubiquitin moiety bound to a label molecule are provided. The second GPCR is not related to the first GPCR. The second cells are exposed to the compounds or sample solutions to be tested and to a known agonist for the second GPCR. It is detected whether interaction of the modified arrestin with the second GPCR is decreased or not increased after exposure to the test compound or solution, a decrease or lack of increase in interaction being an indication that the compound or solution has GPCR desensitization activity independent of the GPCR expressed. Interaction of the modified arrestin with the GPCR may be detected in endosomes, in proximity to a cell membrane, and the like.

The methods of assessing GPCR pathway activity of the present invention also include cell-free assays. In cell-free assays of the present invention, a substrate having deposited thereon a GPCR is provided. A fluid containing a modified arrestin comprising a conjugate of an arrestin and an ubiquitin moiety bound to a label molecule is also provided. Translocation of the modified arrestin is induced and interaction of the modified arrestin with the GPCR is detected. The GPCR and modified arrestin may be obtained from whole cells and used in the cell-free assay after purification. The GPCR has arrestin binding sites and agonist binding sites and may be supported in a multilayer or bilayer lipid vesicle. The vesicle supporting the GPCR may be deposited on the substrate, and the GPCR may be supported in the lipid vesicle and deposited on the substrate such that the arrestin binding sites are exposed to modified arrestin and the receptor binding sites are accessible to agonists. The substrate may be any artificial substrate on which the GPCR may be deposited, including but not limited to, glass, plastic, diamond, ceramic, semiconductor, silica, fiber optic, diamond, biocompatible monomer, biocompatible polymer, polymer beads (including organic and inorganic polymers), and the like.

The present invention relates to the compounds identified as ligands, agonists, antagonists, inverse agonists, or DACs by the methods of assaying of the present invention. These compounds may be used to treat any one of the disease states in which GPCRs have been implicated. The compounds identified may be administered to a human or a non-human in therapeutically effective doses to treat or ameliorate a condition, disorder, or disease in which GPCRs have been implicated. A therapeutically effective dose refers to that amount of the compound sufficient to result in amelioration of symptoms of such a condition, disorder or disease.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of the compound (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to, the severity of the disease or condition, disorder, or disease, previous treatments, the general health and/or age of the subject, and other diseases present. Moreover, treatment of a subject with a therapeutically effective amount of the compounds can include a single treatment or, preferably, can include a series of treatments. In a preferred example, a subject is treated with the compound in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of the compound used for treatment may increase or decrease over the course of a particular treatment. Changes in dosage may result and become apparent from the results of diagnostic assays as described herein.

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral rectal or topical administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In certain embodiments, it may be desirable to administer the pharmaceutical compositions of the invention locally to the area in need of treatment. This may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

For topical application, the compounds may be combined with a carrier so that an effective dosage is delivered, based on the desired activity.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device maybe accompanied by instructions for administration.

Cell Types and Substrates

The cells of the present invention express at least one modified arrestin of the present invention. The cells may further express at least one GPCR. Cells useful in the present invention include eukaryotic and prokaryotic cells, including, but not limited to, bacterial cells, yeast cells, fungal cells, insect cells, nematode cells, plant cells, and animal cells. Suitable animal cells include, but are not limited to, HEK cells, HeLa cells, COS cells, and various primary mammalian cells. An animal model expressing a conjugate of an arrestin chimera and a label molecule throughout its tissues or within a particular organ or tissue type, may also be used in the present invention.

A substrate may have deposited thereon a plurality of cells of the present invention. The substrate may be any suitable biologically substrate, including but not limited to, glass, plastic, ceramic, semiconductor, silica, fiber optic, diamond, biocompatible monomer, or biocompatible polymer materials.

Methods of Detection

Methods of detecting the intracellular location of the modified arrestin molecule, the intracellular location of a GPCR fused to a label molecule, or interaction of the modified arrestin, with a GPCR or any other cell structure, including for example, the concentration of modified arrestin at a cell membrane, colocalization of modified arrestin with GPCR in endosomes, and the like, will vary dependent upon the label molecule(s) used. One skilled in the art readily will be able to devise detection methods suitable for the label molecule(s) used. For optically detectable molecules, any optical method may be used where a change in the fluorescence, bioluminescence, or phosphorescence may be measured due to a redistribution or reorientation of emitted light. Such methods include, for example, polarization microscopy, BRET, FRET, evanescent wave excitation microscopy, and standard or confocal microscopy.

In an embodiment of the invention arrestin-ubiquitin chimera may be further conjugated to GFP and the arrestin-GFP conjugate may be detected by confocal microscopy. In another embodiment, arrestin-ubiquitin conjugate may conjugated to a GFP and the GPCR may be conjugated to an immunofluorescent molecule, and the conjugates may be detected by confocal microscopy. In an additional embodiment, arrestin-ubiquitin conjugate may conjugated to a GFP and the carboxy-terminus of the GPCR may be conjugated to a luciferase and the conjugates may be detected by bioluminescence resonance emission technology. In a further preferred embodiment arrestin-ubiquitin may be conjugated to a luciferase and GPCR may be conjugated to a GFP, and the conjugates may be detected by bioluminescence resonance emission technology. The methods of the present invention are directed to detecting GPCR activity. The methods of the present invention allow enhanced monitoring of the GPCR pathway in real time.

Diagnostic and Therapeutic Treatments

The possibilities of both diagnostic and therapeutic that are raised by the existence of a GPCR derive from the fact that the factors appear to participate in direct and causal protein-protein interaction between a ligand thereto, and those factors that thereafter initiate an intracellular signal. As discussed earlier and elaborated further on herein, the present invention contemplates pharmaceutical intervention in the cascade of reactions in which the GPCR is implicated, to modulate the activity initiated by a GPCR.

Thus, in instances where it is desired to reduce or inhibit the activity resulting from a particular stimulus or factor, an appropriate inhibitor of the GPCR could be introduced to block the interaction of the GPCR with a ligand. Correspondingly, instances in which insufficient activation of a G protein or second messenger is taking place could be remedied by introduction of additional quantities of the GPCR or its chemical or pharmaceutical cognates, analogs, fragments and the like.

As discussed earlier, the GPCRs or their binding partners or other ligands or agents exhibiting either mimicry or antagonism to the GPCRs or control over their production, may be prepared in pharmaceutical compositions, with a suitable carrier and at a strength effective for administration by various means to a patient experiencing an adverse medical condition associated with GPCR activity for the treatment thereof. A variety of administrative techniques may be utilized, among them parenteral techniques such as subcutaneous, intravenous and intraperitoneal injections, catheterizations and the like. Average quantities of the GPCR agonist or antagonist may vary and in particular should be based upon the recommendations and prescription of a qualified physician or veterinarian.

Also, antibodies including both polyclonal and monoclonal antibodies, and drugs that modulate the production or activity of the GPCRs and/or their fragments or subunits may possess certain diagnostic applications and may for example, be utilized for the purpose of detecting and/or measuring conditions such as viral infection or the like. For example, the GPCR or fragments or subunits thereof may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or antagonize the activity(ies) of the GPCR of the invention may be discovered or synthesized, and may be used in diagnostic and/or therapeutic protocols.

The general methodology for making monoclonal antibodies by hybridomas is well known. Immortal, antibody-producing cell lines can also be created by techniques other than fusion, such as direct transformation of B-lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies produced against GPCR peptides can be screened for various properties; i.e., isotype, epitope, affinity, etc. Of particular interest are monoclonal antibodies that neutralize the activity of the GPCR or its subunits. Such monoclonals can be readily identified in GPCR assays. High affinity antibodies are also useful when immunoaffinity purification of native or recombinant modified GPCRs is possible.

Preferably, the anti-GPCR antibody used in the diagnostic methods of this invention is an affinity purified polyclonal antibody. More preferably, the antibody is a monoclonal antibody (mAb). In addition, it is preferable for the anti-GPCR antibody molecules used herein be in the form of Fab, Fab', $F(ab')_2$ or F(v) portions of whole antibody molecules.

As suggested earlier, the diagnostic method of the present invention comprises examining a cellular sample or medium by means of an assay including an effective amount of an antagonist to a GPCR/protein, such as an anti-GPCR antibody, preferably an affinity-purified polyclonal antibody, and more preferably a mAb. In addition, it is preferable for the anti-GPCR antibody molecules used herein be in the form of Fab, Fab', $F(ab')_2$ or F(v) portions or whole antibody molecules. As previously discussed, patients capable of benefiting from this method include those suffering from cancer, a pre-cancerous lesion, a viral infection or other like pathological derangement. Methods for isolating the GPCR and inducing anti-GPCR antibodies and for determining and optimizing the ability of anti-GPCR antibodies to assist in the examination of the target cells are all well known in the art.

Methods for producing polyclonal anti-polypeptide antibodies are well known in the art. See U.S. Pat. No. 4,493,795 to Nestor et al. A monoclonal antibody, typically containing Fab and/or $F(ab')_2$ portions of useful antibody molecules, can be prepared using the hybridoma technology described in *Antibodies—A Laboratory Manual*, Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with a GPCR.

Splenocytes are typically fused with myeloma cells using polyethylene glycol (PEG) 6000. Fused hybrids are selected by their sensitivity to HAT. Hybridomas producing a monoclonal antibody useful in practicing this invention are identified by their ability to immunoreact with the present GPCR and their ability to inhibit specified GPCR activity in target cells.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/l glucose, 20 mm glutamine, and 20% fetal calf serum. An exemplary inbred mouse strain is the Balb/c.

Methods for producing monoclonal anti-GPCR antibodies are also well known in the art. See Niman et al., *Proc. Natl. Acad. Sci. USA*, 80:4949-4953 (1983). Typically, the present GPCR or a peptide analog is used either alone or conjugated to an immunogenic carrier, as the immunogen in the before described procedure for producing anti-GPCR monoclonal antibodies. The hybridomas are screened for the ability to produce an antibody that immunoreacts with the GPCR or peptide analog.

The present invention further contemplates therapeutic compositions useful in practicing the therapeutic methods of this invention. A subject therapeutic composition includes, in admixture, a pharmaceutically acceptable excipient (carrier) and one or more of an agonist, antagonist, or DAC of the GPCR, as described herein as an active ingredient. In a preferred embodiment, the composition comprises a drug capable of modulating the specific binding of a GPCR with a ligand on a target cell.

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents that enhance the effectiveness of the active ingredient.

A GPCR agonist, antagonist, or DAC can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of modulation of GPCR activity desired. Precise amounts of active ingredient required to be administered depend on the judgment of the practitioner and are peculiar to each individual. However, suitable dosages may range from about 0.001 to 30, preferably about 0.01 to about 25, and more preferably about 0.1 to 20 milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

The therapeutic compositions may further include an effective amount of the GPCR agonist, antagonist, or DAC and one or more of the following active ingredients: an antibiotic, a steroid, and the like.

Expression of the Modified Arrestins

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col E1, pCR1, pBR322, pMB9 and their derivatives, plasmids such as RP4; phage DNAS, e.g., the numerous derivatives of phage λ, e.g., NM989, and other phage DNA, e.g., MI 3 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast a-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of E. coli, Pseudomonas, Bacillus, Streptomyces, fungi such as yeasts, plant cells, nematode cells, and animal cells, such as HEK-293, CHO, RII, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences of this invention on fermentation or in large-scale animal culture.

It is further intended that modified arrestin analogs may be prepared from nucleotide sequences of the protein complex/subunit derived within the scope of the present invention. Analogs, such as fragments, may be produced, for example, by pepsin digestion of arrestin material. Other analogs, such as muteins, can be produced by standard site-directed mutagenesis of arrestin coding sequences. Analogs exhibiting "GPCR activity" such as small molecules, whether functioning as promoters or inhibitors, may be identified by known in vivo and/or in vitro assays.

As mentioned above, a DNA sequence encoding a modified arrestin can be prepared synthetically rather than cloned. The DNA sequence can be designed with the appropriate codons for the arrestin amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, Nature, 292:756 (1981); Nambair et al., Science, 223:1299 (1984); Jay et al., J. Biol. Chem., 259:6311 (1984).

Synthetic DNA sequences allow convenient construction of genes that will express arrestin analogs or "muteins". Alternatively, DNA encoding muteins can be made by site-directed mutagenesis of native or modified GPCR genes or cDNAs, and muteins can be made directly using conventional polypeptide synthesis.

A general method for site-specific incorporation of unnatural amino acids into proteins is described in Christopher J. Noren, Spencer J. Anthony Cahill, Michael C. Griffith, Peter G. Schultz, Science, 244:182-188 (April 1989). This method may be used to create analogs with unnatural amino acids.

Diagnostic Applications

The present invention also relates to a variety of diagnostic applications, including methods for detecting the presence of stimuli such as the earlier referenced polypeptide ligands, by reference to their ability to elicit the activities that are mediated by GPCRs. As mentioned earlier, the GPCRs can be used to produce antibodies to itself by a variety of known techniques, and such antibodies could then be isolated and utilized as in tests for the presence of particular GPCR activity in suspect target cells. In particular, the antibodies may be utilized as in tests for the presence of GPCRs having point mutations that increase their affinity for arrestin in suspect target cells.

As described in detail above, antibody(ies) to the GPCR, can be produced and isolated by standard methods including the well-known hybridoma techniques. For convenience, the antibody(ies) to the GPCR will be referred to herein as $Ab_1$ and antibody(ies) raised in another species as $Ab_2$.

The presence of GPCRs, in cells can be ascertained by the usual immunological procedures applicable to such determinations. A number of useful procedures are known. Three such procedures which are especially useful utilize either the GPCR labeled with a detectable label, antibody Ab1 labeled with a detectable label, or antibody Ab2 labeled with a detectable label. The procedures may be summarized by the following equations wherein the asterisk indicates that the particle is labeled:

$$GPCR^* + Ab_1 = GPCR^* Ab_1 \qquad \text{A.}$$

$$GPCR + Ab^* = GPCR Ab_1^* \qquad \text{B.}$$

$$GPCR + Ab_1 + Ab_2^* = GPCR Ab_1 Ab_2^* \qquad \text{C.}$$

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody," or "DASD" procedure.

In each instance, the GPCR forms complexes with one or more antibody(ies) or binding partners and one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because $Ab_1$ raised in one mammalian species has been used in another species as an antigen to raise the antibody $Ab_2$. For example, $Ab_2$ may be raised in goats using rabbit antibodies as antigens. $Ab_2$ therefore would be anti-rabbit antibody raised in goats. For purposes of this description and claims, $Ab_1$ will be referred to as a primary or anti-GPCR antibody, and $Ab_2$ will be referred to as a secondary or anti-$Ab_1$ antibody.

The labels most commonly employed for these studies are radioactive elements, enzymes, chemicals that fluoresce when exposed to ultraviolet light, and others.

A number of fluorescent materials are known and can be utilized as labels. These include, for example, fluorescein, rhodamine, auramine, Texas Red, AMCA blue, GFP and Lucifer Yellow. A particular detecting material is anti-rabbit antibody prepared in goats and conjugated with fluorescein through an isothiocyanate.

The GPCR or its binding partner(s) can also be labeled with a radioactive element or with an enzyme. The radioactive label can be detected by any of the currently available counting procedures. The preferred isotope may be selected from $^3H$, $^{14}C$, $^{32}P$, $^{35}S$, $^{36}Cl$, $^{51}Cr$, $^{57}Co$ $^{58}Co$, $^{59}Fe$, $^{90}Y$ $^{125}I$ $^{131}I$, and $^{186}Re$.

Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

A particular assay system developed and utilized in accordance with the present invention is known as a receptor assay. In a receptor assay, the material to be assayed is appropriately labeled and then certain cellular test colonies are inoculated with a quantity of both the labeled and unlabeled material after which binding studies are conducted to determine the extent to which the labeled material binds to the cell receptors. In this way, differences in affinity between materials can be ascertained.

Accordingly, a purified quantity of the GPCR may be radiolabeled and combined, for example, with antibodies or other inhibitors thereto, after which binding studies would be carried out. Solutions would then be prepared that contain various quantities of labeled and unlabeled uncombined GPCR, and cell samples would then be inoculated and thereafter incubated. The resulting cell monolayers are then washed, solubilized and then counted in a gamma counter for a length of time sufficient to yield a standard error of <5%. These data are then subjected to Scatchard analysis after which observations and conclusions regarding material activity can be drawn. While the foregoing is exemplary, it illustrates the manner in which a receptor assay may be performed and utilized, in the instance where the cellular binding ability of the assayed material may serve as a distinguishing characteristic.

An assay useful and contemplated in accordance with the present invention is known as a "cis/trans" assay. Briefly, this assay employs two genetic constructs, one of which is typically a plasmid that continually expresses a particular receptor of interest (e.g., a GPCR) when transfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescence is then measured photometrically, and dose response curves are obtained and compared to those of known ligands. The foregoing protocol is described in detail in U.S. Pat. No. 4,981,784 and PCT International Publication No. WO 88/03168, for which purpose the artisan is referred.

Test Kits

In a further embodiment of this invention, commercial test kits suitable for use by a medical specialist may be prepared to determine the presence or absence of predetermined GPCR activity or predetermined GPCR activity capability in suspected target cells. In accordance with the testing techniques discussed above, one class of such kits will contain at least the labeled GPCR or its binding partner, for instance an antibody specific thereto, and directions, of course, depending upon the method selected, e.g., "competitive," "sandwich," "DASP" and the like. The kits may also contain peripheral reagents such as buffers, stabilizers, etc.

Accordingly, a test kit may be prepared for the demonstration of the presence or capability of cells for predetermined GPCR activity, comprising:

(a) a predetermined amount of at least one labeled immunochemically reactive component obtained by the direct or indirect attachment of the present GPCR or a specific binding partner thereto, to a detectable label;

(b) other reagents; and (c) directions for use of said kit.

More specifically, the diagnostic test kit may comprise:

(a) a known amount of the GPCR as described above (or a binding partner, or in the alternative, bound to a suitable tag, or plural such end products, etc. (or their binding partners) one of each;

(b) if necessary, other reagents; and (c) directions for use of said test kit.

In a further variation, the test kit may be prepared and used for the purposes stated above, which operates according to a predetermined protocol (e.g. "competitive," "sandwich," "double antibody," etc.), and comprises:

(a) a labeled component that has been obtained by coupling the GPCR to a detectable label;

(b) one or more additional immunochemical reagents of which at least one reagent is a ligand or an immobilized ligand, which ligand is selected from the group consisting of:

(i) a ligand capable of binding with the labeled component (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined; and (c) directions for the performance of a protocol for the detection and/or determination of one or more components of an immunochemical reaction between the GPCR and a specific binding partner thereto.

In accordance with the above, an assay system for screening potential drugs effective to modulate the activity of the GPCR may be prepared. The GPCRs and modified arrestins may be introduced into a test system, and the prospective drug may also be introduced into the resulting cell culture, and the culture thereafter examined to observe any changes in the GPCR activity (e.g., signaling, recycling, affinity for arrestin, and the like) in the cells.

The following examples are presented in order to more fully illustrate the preferred embodiments of the invention. They should in no way be construed, however, as limiting the broad scope of the invention.

EXAMPLES

β-Arrestin Ubiquitination and Deubiquitination Correlates with the Stability of GPCR-(β-Arrestin Complex During Agonist-Promoted Internalization Stimulation of β2AR in COS-7 cells with the agonist isoproterenol lead to robust ubiquitination of β-arrestin2 at about 1 minute after agonist treatment, and (FIG. 1A). However this ubiquitination signal diminished within 15 min. In contrast, stimulation of either V2vassopressin receptors or Angiotensin AT1 a receptor lead to a stable ubiquitination pattern (Fig I B, and data not shown). With these receptors β-arrestin2 was ubiquitinated robustly within 1 min but the signal did not diminish at 15 min. Interestingly βarrestin2 was both monoubiquitinated (see band indicated at Mr ~60 kDa in FIGS. 1 A and 1 B) and polyubiquitinated (attachment of first ubiquitin to the substrate lysine followed by formation of a polyubiquitin chain on the first ubiquitin) or possibly multi-ubiquitinated (ubiquitination of substrate at several lysines). Similar isoproterenol-stimulated ubiquitination pattern was also seen with the βarrestin1 isoform (not shown). A striking correlation was drawn between ubiquitination and intracellular trafficking patterns of β-arrestins with β2AR and V2R. As shown in FIGS. 1 C and 1 D, GFP-β-arrestin2 (top row) was uniformly distributed in the cytoplasm in unstimulated cells. The receptors middle row) were seen at the plasma membrane.

Within 1 min of respective stimuli, β-arrestin2 translocated to the plasma membrane in both cases. However at 15 minutes after stimulation, in the case of β2AR, the receptor alone was seen in the endocytic vesicles, with the β-arrestin still at the plasma membrane whereas in the case of V2R both β-arrestin and receptor were seen colocalized in endocytic vesicles (bottom row). Thus the ubiquitination and deubiduitination time course of β-arrestin paralleled its association with and dissociation from the two types of receptor.

Interaction of β-Arrestin with GPCR Tail Residues Governs Both Intracellular Trafficking and Ubiquitination Patterns of β-Arrestin.

The differing affinity of a class A versus a class B GPCR for β-arrestin has been attributed to the phosphorylation by GRKs of specific serine clusters in the tail region of the GPCR. Moreover, the exchange of the cytoplasmic tail residues between the two-receptor classes leads to reversal of the patterns of βarrestin affinity for the receptors as well as intracellular trafficking. As shown in FIG. 2A, a chimeric (β2ARV2CT with the first 341 amino acids of the β2AR (Met-1 to Cys341) fused to the last 29 amino acids of the V2R (Ala-343 to Ser371) interacted with β-arrestin more stably and hence after 15 min of isoproterenol stimulation, both the receptor and β-arrestin colocalized in endosomes. On the other hand the chimera V2RR2CT which contains the first 342 amino acids of the V2R (Met1-Cys342) fused to the last 72 amino acids of the β2AR (Leu342 to Leu 413) showed the transient β-arrestin-binding pattern of the β2AR and hence β-arrestin remained at the plasma membrane and receptor alone trafficked to endosomes (FIG. 2B).

If the ability of β-arrestin to remain ubiquitinated is dependent on its interaction with the GPCR, one might expect that the receptor cytoplasmic tail residues would govern the pattern of ubiquitination. To test this hypothesis, we determined the agonist promoted ubiquitination patterns of β-arrestin for the 2 chimeric receptors. As shown in FIG. 2C, 1 min isoproterenol stimulation of COS-7 cells expressing β2ARV2CT lead to a marked increase in β-arrestin ubiquitination which did not decrease at 15 min. In marked contrast the stimulation of the chimera V2Rβ2CT lead to a very robust increase in ubiquitination at 1 min of AVP treatment, but the signal returned to almost basal levels at 15 min (FIG. 2D). These results, together with the data shown in FIG. 1, strongly suggested that the ubiquitinated form of β-arrestin corresponded to the receptor-bound β-arrestin complex.

A Persistently Ubiquitinated Form of β-Arrestin2 Showed Enhanced Binding to GPCR.

Applicants' data suggest that β-arrestin2 translocated to the plasma membrane and became ubiquitinated within a minute of GPCR stimulation, but was deubiquitinated with differing kinetics depending upon the receptor. However, it is unknown whether deubiquitination was a cause or consequence of β-arrestin dissociation from the receptor. Applicants theorized that fusion of a ubiquitin moiety to the β-arrestin protein would provide a persistently ubiquitinated form of β-arrestin. If β-arrestin2 deubiquitination was the trigger for dissociation from the class A receptor, then the chimeric protein would not dissociate from the receptor and would show tighter binding to the class A receptor than wild type β-arrestin because it cannot be efficiently deubiquitinated. On the other hand, if deubiquitination of β-arrestin occurs after its dissociation from the receptor then there should be no alterations in β-arrestin-Ub binding or in its dissociation kinetics.

Since ubiquitinated proteins are substrates for proteasomal degradation, Applicants tested the stability of a β-arrestin-Ub chimeric protein (FIG. 3A). A comparison of the half-lives of YFP-β-arrestin2 and YFP-β-arrestin2-Ub is also shown in FIG. 3A. Wild type β-arrestin2 had a half-life of about 10-12 hours in COS-7 cells as determined by $_{35}S$ metabolic labeling. Not surprisingly, fusion of ubiquitin in frame to β-arrestin decreased its halflife to about 2 hours (FIG. 3A). Nonetheless the chimeric protein could be over expressed in sufficient amounts to be detected by antibody to both β-arrestin (not shown) and YFP (FIG. 3B).

Several research groups have demonstrated coimmunoprecipitation (in the presence or absence of chemical crosslinking reagents) of β-arrestin 2 with β2AR. However, under such experimental conditions only a modest increase of the protein interaction was observed upon agonist treatment. In contrast, as assessed by confocal microscopy with YFP or GFP tagged β-arrestin, within a few seconds of isoproterenol treatment, a major portion of the cytosolic β-arrestin moved to the plasma membrane and colocalized with the receptor. If (β-arrestin ubiquitination contributed to the stability of the GPCR-β-arrestin interaction, then coimmunoprecipitation done under conditions that preserve the ubiquitination of β-arrestin, such as treatment with NEM (which inactivates deubiquitinating enzymes) should result in a considerable increase in the amount of β-arrestin that coprecipitated with the receptor. This indeed is the case as shown in FIG. 3B which compares the amount of β-arrestin that coimmunoprecipitated with β2AR in the presence and absence of NEM. The laddering of bands as detected by the antibody to YFP-β-arrestin represented the multimerized as well as ubiquitinated forms of the β-arrestin protein. Note that these bands were not detectable at 15 minutes of agonist treatment with the wild type YFP-β-arrestin2 but were detectable with the chimeric protein, YFP-β-arrestin2-Ub. This was probably because the chimeric protein was not efficiently deubiquitinated as is the wild type, and hence was detectable as the receptor bound form of β-arrestin2. The 90-kDa band that corresponded to monoubiquitinated YFP-β-arrestin2 is indicated in the figure panel.

Expression of β-Arrestin-Ub Chimera Transforms a Class A Receptor to Class B with Respect to Intracellular Trafficking.

Figure 4A:
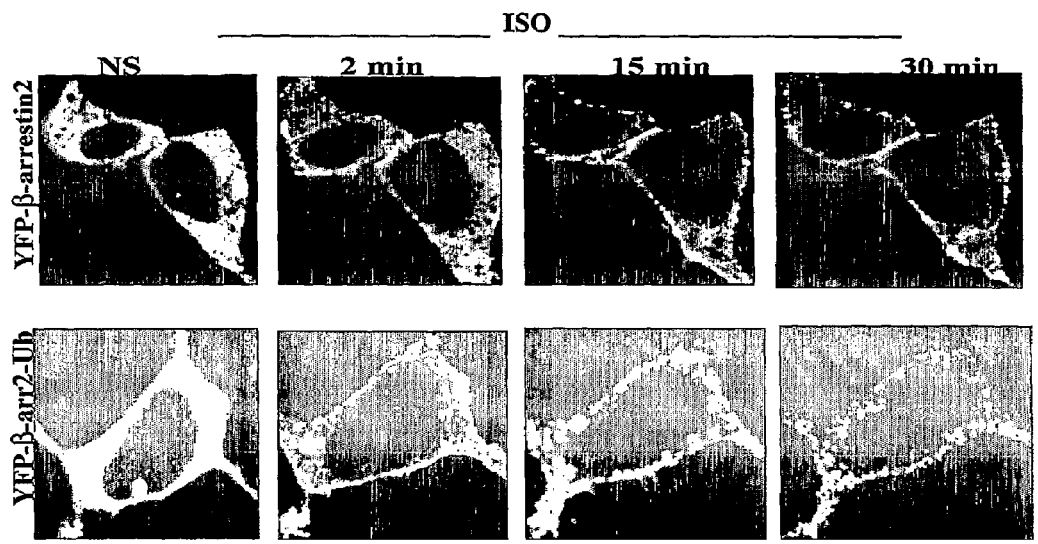

To determine whether β-arrestin-Ub chimeric protein influenced its trafficking Applicants utilized confocal microscopy to examine the fluorescent proteins in live cells. FIG. 4A illustrates the trafficking of wild type YFP-βarrestin2 in HEK293 cells transiently over expressing β2AR. In unstimulated cells, YFPβ-arrestin2 was homogeneously distributed in the cytoplasm. Within 2 min of isoproterenol treatment, β-arrestin was seen to concentrate at the plasma membrane. The distribution of YFP-β-arrestin was unaltered at 30 min of isoproterenol treatment (FIG. 4A upper panels). The punctate fluorescence of YFP-β-arrestin2 at the membrane was probably due to its localization in clathrin coated pits at the plasma membrane. A cytosolic distribution of YFP-β-arrestin2-Ub in unstimulated and plasma membrane localization in 2 min stimulated cells is shown in FIG. 4A, lower panels. However at 15 min, YFP-β-arrestin-Ub was seen to redistribute from the plasma membrane to endocytic vesicles. Longer agonist treatment resulted in a further increase in number as well as size of YFP-β-arrestin-Ub containing endocytic vesicles.

Figure 4B:
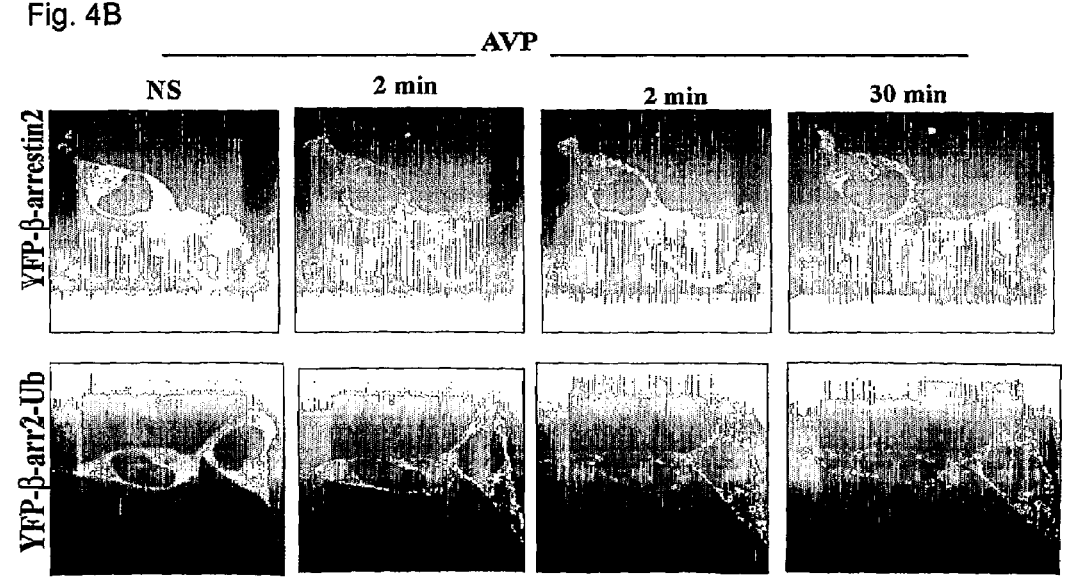

V2Rβ2CT is a chimeric receptor in which the class B pattern of trafficking and ubiquitination is converted to that of a class A receptor. (FIGS. 2B and 2D). Stimulation of V2Rβ2CT with AVP lead to the redistribution of YFP-β-arrestin2 to the plasma membrane in a punctate pattern like the β2AR (FIG. 4B upper panels) at 2 min. The YFPβ-arrestin2 remained at the plasma membrane at longer time points. On the other hand, YFP-β-arrestin-Ub, which translocated to the plasma membrane within 2 minutes of agonist, moved into endocytic vesicles as early as 15 min of AVP treatment (FIG. 4B lower panels). Addition of tail residues of β32AR (class A) to V2R (class B) conferred class A trafficking pattern to V2Rβ2CT chimeric receptor. As a further step, over expression of YFP-(β-arrestin2-Ub reverted the trafficking pattern back to that of class B. Thus a "double-reversal" of β-arrestin trafficking pattern was seen '30 with respect to V2Rβ2CT.

Figure 5A:
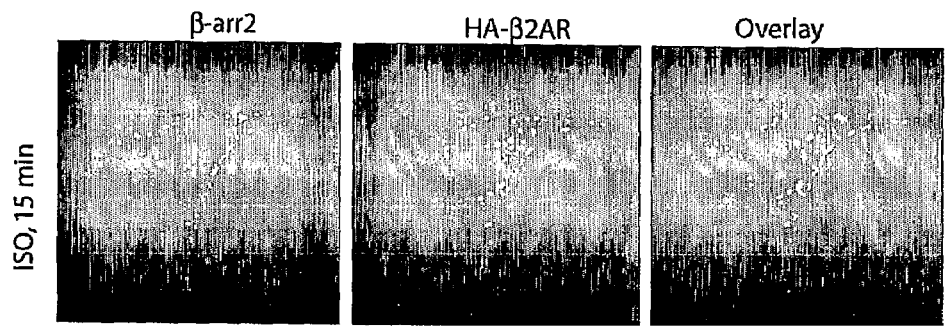
Figure 5B:
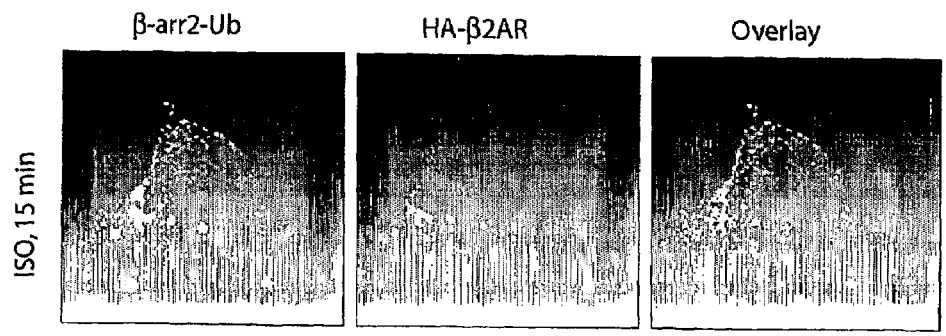

To determine whether the YFP-β-arrestin2-Ub in endocytic vesicles colocalized with the GPCR, Applicants examined the distribution of both β2AR and β-arrestin after 15 minutes of isoproterenol treatment (FIG. 5). In unstimulated cells receptor was seen at the plasma membrane and either YFP-β-arrestin or YFP-β-arrestin-Ub was seen uniformly distributed in the cytoplasm. Stimulation of cells with isoproterenol for 15 minutes resulted in the redistribution of β2AR (red) and YFP-β-arrestin2 (green) into small puncta at the plasma membrane, which likely represented colocalization of β2AR and YFP-β-arrestin in clathrin-coated pits at the membrane (FIG. 5A). Internalized receptors, seen as red vesicles in the cytoplasm, did not however contain any YFP-β-arrestin2, suggesting that β-arrestin2 dissociated from the receptor during or shortly after vesicle formation. FIG. 5B shows the distribution of β2AR and YFP-β-arrestin2-Ub after 15 min of isoproterenol treatment. In contrast to what was seen with wild type YFP-β-arrestin2, the YFP-β-arrestin-Ub chimera was seen to colocalize with the internalized β2AR. Further, very little staining of either protein was seen at the plasma membrane. Thus, an ubiquitinated form of β-arrestin2 can transform a class A receptor such as the β2AR into a class B receptor with respect to its pattern of internalization.

Effect of β-Arrestin-Ub on the Internalization and Degradation of β2AR.

Since β-arrestin2-Ub can form stable complexes with β2AR, Applicants tested whether this interaction had any effect on agonist stimulated receptor internalization. As shown FIG. 6A, β2AR internalization, as measured in HEK293 cells after a 30 min isoproterenol treatment, was 25±1.8%. Upon overexpression of β-arrestin2 and β-arrestin2-Ub the internalization increased to 33±1.6% and 44±3.5% respectively. Pretreatment of cells with 200 μM MDC, a known inhibitor of receptor movement to clathrin coated pits reduced this internalization by 45%, (data not shown) suggesting that the β-arrestin-Ub promoted internalization proceeds via clathrin coated vesicles.

Figure 6B:
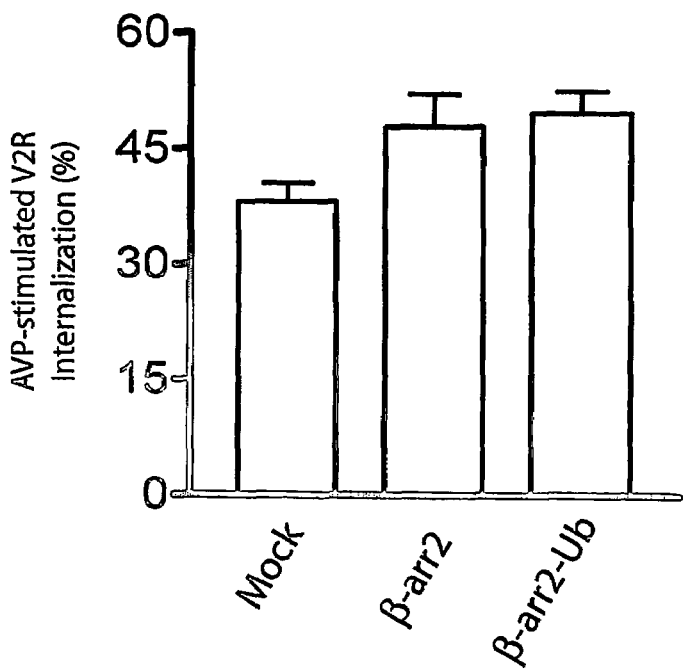

Over expression of β-arrestin-Ub did not however result in a similar enhancement of internalization of V2R over wild type β-arrestin as measured after 30 min of AVP stimulation (FIG. 6B). This result was expected since the ubiquitination of β-arrestin is stable with this receptor.

Figure 7A:
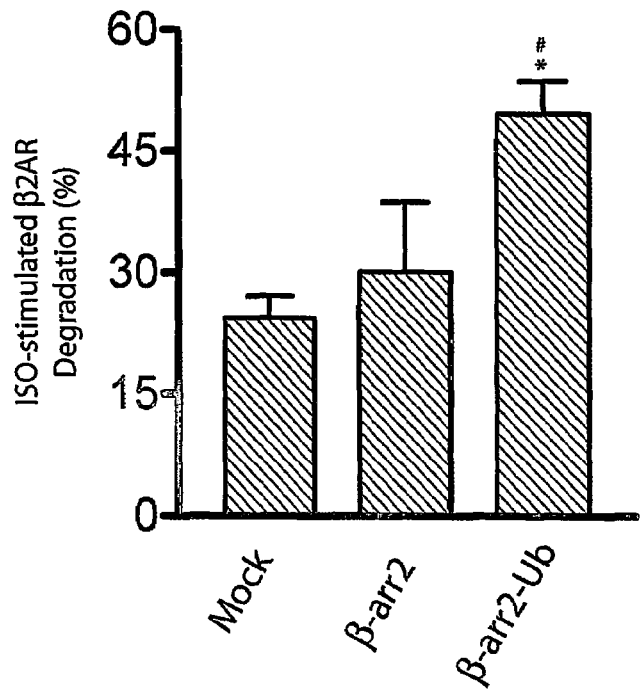
Figure 7B:
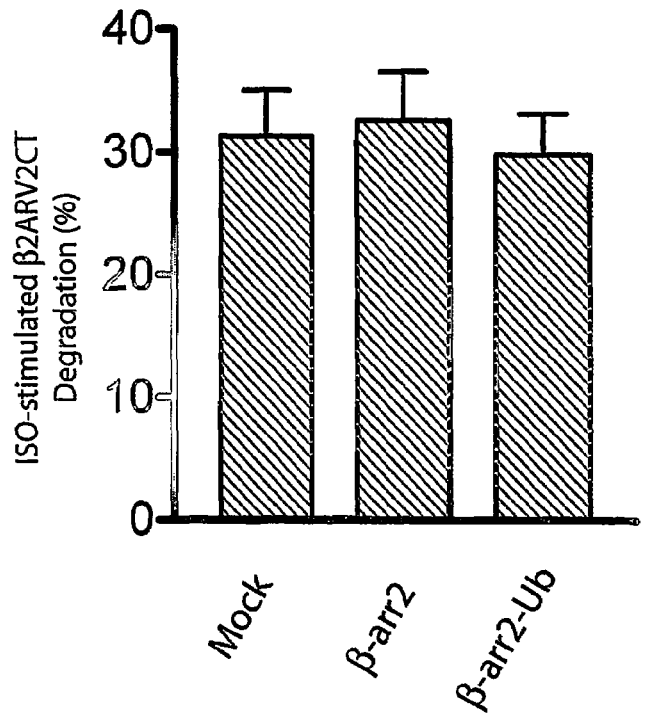

A short-term isoproterenol treatment of cells expressing β 2AR resulted in a decrease in the number of cell surface receptors without changing total cellular receptor levels. However, prolonged exposure to isoproterenol, for hours or days, resulted in a decline in the total receptor number, measurable by radioligand binding. In HEK 293 cells, after 24 hrs of isoproterenol treatment, over expressed β2AR levels decreased by about 25% (FIG. 7A). The amount of degradation increased with β-arrestin over expression by about 6-7%. On the other hand, the amount of receptor degradation doubled when β-arrestin2-Ub was coexpressed with the receptor. For comparison, Applicants measured the degradation of the β2ARV2CT chimera, which essentially mimics the properties of V2R with respect to endocytosis. However, no change in the degradation of β2ARV2CT was observed with β-arrestin2-Ub over expression (FIG. 7B). These data suggested that the ubiquitination status of β-arrestin influenced both the rate at which a given receptor was sequestered from the plasma membrane as well as the likelihood that it was sorted to lysosomes.

Binding of (β-arrestins to activated receptors leads to homologous receptor desensitization as well as to the recruitment of specialized endocytic machinery to internalize receptors. Both β-arrestin and the β2AR undergo agonist dependent ubiquitination. In the case of yeast a-factor receptor, ubiquitination appears to serve as an internalization signal. However, β2AR ubiquitination, which requires β-arrestin as an adaptor to recruit ubiquitination enzymes, is necessary for targeting of the receptors to lysosomes for degradation rather than for their internalization. Interestingly, β-arrestin ubiquitination catalyzed by Mdm2, a RING-type E3 ubiquitin ligase, is required for 12AR internalization.

The β2AR and the V2R are seven-membrane spanning receptors, which typify two very different patterns of receptor trafficking and β-arrestin interaction. Importantly, β2AR stimulation lead to a transient pattern of β-arrestin ubiquitination while V2R stimulation lead to stable β-arrestin ubiquitination, which parallels the intracellular trafficking interaction of β-arrestin with these two receptors. Exchanging the C-terminal domains of these two receptors reversed the ubiquitination patterns of β-arrestin. Agonist stimulation of the β2AR lead to the recruitment of β-arrestin to the cell membrane within a few seconds, where it was ubiquitinated. β2ARs then moved to clathrin coated pits and were internalized into vesicles within 15 min. This event was accompanied by the dissociation of β-arrestin from the receptor following its deubiquitination. This order of events was supported by the experiments done with a chimeric β-arrestin with ubiquitin fused to its carboxyl terminus. Stimulation of the β2AR with isoproterenol lead to the redistribution of this chimera to the plasma membrane where it colocalizes with the receptor. However, unlike its wild type counterpart, the ubiquitin chimera did not dissociate from the receptor but was seen to colocalize with the receptor in endocytic vesicles. If deubiquitination occurred after (β-arrestin dissociation, the ubiquitin chimera would have nevertheless dissociated from the receptor. Thus stable ubiquitination forced β-arrestin to move into endocytic vesicles with the receptor. However, this movement could also be due to its tighter association with the receptor as seen in the coimmunoprecipitation experiments done in the presence of inhibitors of deubiquitinating enzymes. Thus, Applicants' data indicated that when β-arrestin interacted with a class A receptor it was prone to deubiquitination, and this caused it to dissociate from the receptor at the plasma membrane.

The persistence of ubiquitin moieties on β-arrestin2 correlated with more robust sequestration of the β2AR, a class A receptor, and also lead to increased degradation of these receptors. Presumably, the presence of ubiquitinated β-arrestin in complex with internalized receptors lead to more efficient sorting of these internalized receptors to lysosomes. Whether this was the result of inhibition of receptor dephosphorylating enzymes, blocking the interaction of recycling proteins such as NSF, enhancing the interaction with sorting proteins such as the sorting nexins or some other mechanism remains to be determined.

The data thus revealed a previously unappreciated connection between the ubiquitin modification of arrestin and its trafficking pattern with distinct types of receptors. Recently, ubiquitination of adaptor proteins has been implicated as a trigger for downstream signaling pathways. It was shown that stimulation of IL-1 receptors recruits the adaptor TRAF. Dimerization and auto-ubiquitination of TRAF at the membrane triggers the Kinase TAK1 that can activate I kappa β kinase. Applicants have observed that agonist stimulation of receptors such as AT1A and V2R lead to sustained ubiquitination of β-arrestins. These receptors, when activated, are also known to engage pools of arrestin and active ERK-complexes in the cytoplasm. Arrestin ubiquitination may form a foundation for scaffolding of these signaling complexes on endosomes.

Materials—LipoFECTAMINE was from Life Technologies. FuGene 6 was from Roche Diagnostics. M2 anti FLAG affinity agarose beads, monodansylcadaverine (MDC), isoproterenol, arginine-vassopressin peptide, anti flag M1 antibody, FITC-anti-mouse secondary IgG were from Sigma. pEYFP-C1, anti-GFP monoclonal antibody were from Clontech. Ubiquitin antibody UbP4D1 was from Santa Cruz Biotechnology. Monoclonal antibody 12CA5 to HA epitope was from Boerringher-Mannheim. Easy tag™ express protein labeling mix[35S-], and [125I](-iodocyanopindolol were from NEN The expression plasmids for YFP-β-arrestin2-Wild Type, β2ARV2CT, V2Rβ2CT were provided by Dr. Marc Caron at Duke University.

The plasmids pCDNA3-β-arrestin2-Ub and pEYFPC1-β-arrestin2-Ub were constructed as follows: A 1250 base pair DNA fragment encoding βarrestin2 was amplified to contain 5'KpnI-Hind III and 3'Sal I ends; a 221 base pair DNA fragment encoding ubiquitin was amplified to contain 5'Sal I and 3'Xba I ends. The two fragments were ligated together with pcDNA3 with HindIII and XbaI ends to obtain β-arrestin2-Ub expression plasmid. A 1500 bp DNA fragment-encoding β-arrestin2-Ub was subcloned into the Kpnl and Apa I sites of pEYFPC1 vector to obtain the expression plasmid for YFP-β arrestin2-Ub. All constructs were verified by DNA Sequencing.

Cell Culture and Transfection—COS-7 and HEK293 cells were obtained from American Type Culture Collection. COS-7 cells were maintained in Dulbecco's modified Eagle's medium (Life Technologies, Inc.) supplemented with 10% Fetal Bovine Serum and 1% penicillin streptomycin and transiently transfected with LipoFECTAMINE reagent. HEK cells were maintained in Minimal Essential Medium supplemented with Fetal Bovine Serum and transiently transfected with FuGene 6 reagent.

Immunoprecipitation and Immunoblotting—To detect ubiquitinated β-arrestin2, β-arrestin2 with a C-terminal Flag epitope was transiently transfected into COS-7 cells. Cells were serum starved for at least 2 hrs and then stimulated or not for the stipulated times with the appropriate agonists. Cells were solubilized in a lysis buffer (LB) containing 50 mM Hepes (pH7.5), 0.5% NP40, 250 mM NaCl, 2 mM EDTA, 10% (v/v) glycerol, 1 mM sodium orthovanadate, 1 mM sodium fluoride, 1 mM phenylmethylsulfonyl fluoride, leupeptin (5 μg/ml) aprotinin (5 μg/ml), pepstatin A (1 μg/ml) benzaminidine (100 μM) 2 μM MG132 and 10 mM NEM. Soluble extracts were mixed with FLAG M2 affinity beads and rotated at 4° C. overnight. Nonspecific binding was eliminated by repeated washes with LB and bound protein was eluted with sample buffer containing SDS. The proteins were transferred to nitrocellulose membrane for western blotting. Chemiluminiscent detection was performed using SuperSignal® West Pico reagent (Pierce)

Metabolic labeling—COS-7 cells were transiently transfected with YFPβ-arrestin2 or YFP-β-arrestin2-Ub. Prior to labeling with isotope, the cells were washed 2 times with methionine and cysteine free media and incubated in this media for 10 minutes. Cells were incubated with radiolabel solution (DMEM, 10 mM HEPES pH 7.5, 2% dialyzed FBS, 300 μCi/mL of $_{35}$S) for 20 minutes at 37° C. after which the cells were washed 3 times with regular media and incubated in media for 0, 2, 4, 6, 8, 10, and 12 hours at 37° C. At the end of incubation at each time point, the cells were lysed in glycerol lysis buffer (above) and the protein immunoprecipitated with GFP-agarose beads (Santa Cruz) or Al CT antibody.

Receptor internalization—Flag or HA epitope tagged receptors expressed in HEK-293 cells in twelve-well dishes were treated with or without agonist for 30 min in serum-free medium at 37° C. Cell surface receptors were labeled with M1 Flag mAb or 12CA5 mAB, and fluorescein isothiocyanate conjugated goat antibody to mouse IgG as secondary antibody. Receptor internalization was quantified as loss of cell surface receptors, as measured by flow cytometry.

Receptor Degradation—Degradation assays were done with [125I]-(−)Iodocyanopindolol (125I GYP) radioligand binding as reported before (14) on whole cells gently resuspended in DMEM buffered with 10 mM Hepes (pH 7.5). Binding was performed in triplicate with 400 PM 125I CYP in the presence or absence of the hydrophobic antagonist propranolol (10 μM, to define nonspecific binding). Binding was terminated by rapid dilution and filtration on Whatman GFC glass fiber filters. For degradation assays incubation was at 30° C. for 30 min and receptor number (total specific 1251CYP binding sites) was determined after 24 hours of isoproterenol treatment and expressed as percent of receptor number assessed d in nonstimulated cells.

Confocal Microscopy—HEK-293 cells have a favorable morphology to examine sections of cytoplasm and nucleus simultaneously and hence were used in these experiments. HEK-293 cells on 10 cm dishes were transiently transfected with HA-β2AR, HA-V2R, HAβ2ARV2CT, or HAV2Rβ2CT, along with β-arr2-GFP, or YFP-βarrestin2, or YFP-β-arrestin2-Ub. Twenty-four hours post-transfection cells were plated on collagen-coated 35 mm glass bottom plates. Cells were starved for at least 2 hrs in serum free medium prior to stimulation. After stimulation cells were fixed with 4% paraformaldehyde. For visualizing HA-tagged receptors, fixed cells were permeabilized with 0.01% Triton in PBS containing 2% BSA for 20 min and incubated at room temperature with 12CA5 antibody at 1:500 dilution. The secondary antibody, antimouse IgG conjugated to TexasRed, followed this. Antibody incubations were done for one hour followed by repeated washes using PBS. Cells expressing low and equivalent levels of the fluorescent proteins were carefully selected to examine YFP-β-arrestins. Confocal images were obtained on Zeiss LSM510 laser scanning microscope using dual excitation (488, 568 nm) and emission (515-540 nm GFP,YFP; 590-610 nm, Texas red) filter sets. Live images were acquired using a heated (37° C.) microscope stage and collected sequentially using single line excitation (488 nm).

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

The following is a list of documents related to the above disclosure and particularly to the experimental procedures and discussions. The following documents, as well as any documents referenced in the foregoing text, should be considered as incorporated by reference in their entirety.

1. Lefkowitz, R. J. (1998) *J Biol Chem* 273(30), 18677-80.
2. Perry, S. J., and Lefkowitz, R. J. (2002) *Trends Cell Biol* 12(3), 130-8.
3. Luttrell, L. M., Ferguson, S. S., Daaka, Y., Miller, W. E., Maudsley, S., Della Rocca, G. J., Lin, F., Kawakatsu, H., Owada, K., Luttrell, D. K., Caron, M. G., and Lefkowitz, R. J. (1999) *Science* 283(5402), 655-61.
4. McDonald, P. H., Chow, C. W., Miller, W. E., Laporte, S. A., Field, M. E., Lin, F., T., Davis, R. J., and Lefkowitz, R. J. (2000) *Science* 290(5496), 1574-7.
5. Luttrell, L. M., Roudabush, F. L., Choy, E. W., Miller, W. E., Field, M. E., Pierce, K. L., and Lefkowitz, R. J. (2001) *Proc Natl Acad Sci USA* 98(5), 2449-54.
6. Krupnick, J. G., Goodman, O. B., Jr., Keen, J. H., and Benovic, J. L. (1997) *J Biol Chem* 272(23), 15011-6.
7. Laporte, S. A., Oakley, R. H., Zhang, J., Holt, J. A., Ferguson, S. S., Caron, M., G., and Barak, L. S. (1999) *Proc Natl Acad Sci USA* 96(7), 3712-7.
8. Claing, A. Chen, W. Miller, W. E. Vitale, N. Moss, J. Premont, R. T. Lefkowitz, R. J (2001) *J Biol Chem* 276(45), 42509-13.
9. Hicke, L., and Riezman, H. (1996) *Cell* 84(2), 277-87.
10. Roth, A. F., and Davis, N. G. (1996) *J Cell Biol* 134(3), 661-74.
11. Mori, S., Tanaka, K., Omura, S., and Saito, Y. (1995) *J Biol Chem* 270(49), 29447-52.
12. Mori, S., Tanaka, K., Kanaki, H., Nakao, M., Anan, T., Yokote, K., Tamura, K., and Saito, Y. (1997) *Eur J Biochem* 247.7(3), 1190-6.
13. Govers, R., ten Broeke, T., van Kerkhof, P., Schwartz, A. L., and Strous, G. J. (1999) *Embo J* 18(1), 28-36.
14. Shenoy, S. K., McDonald, P. H., Kohout, T. A., and Lefkowitz, R. J. (2001) *Science* 294(5545), 1307-13.
15. Oakley, R. H., Laporte, S. A., Holt, J. A., Caron, M. G., and Barak, L. S. (2000) *J Biol Chem* 275(22), 17201-10.
16. Oakley, R. H., Laporte, S. A., Holt, J. A., Barak, L. S., and Caron, M. G. (1999) *J Biol Chem* 274(45), 32248-57.
17. Oakley, R. H., Laporte, S. A., Holt, J. A., Barak, L. S., and Caron, M. G. (2001) *J Biol Chem* 276(22), 19452-60.
18. Hershko, A., and Ciechanover, A. (1998) *Annu Rev Biochem* 67, 425-79.
19. Phonphok, Y and Rosenthal, K. S (1991) *FEBS Lett.* 281, 188-190.
20. Cong, M., Perry, S. J., Hu, L. A., Hanson, P. I., Claing, A., and Lefkowitz, R. J. (2001) *J Biol Chem* 276(48), 45145-52.
21. Zheng, B., Ma, Y. C., Ostrom, R. S., Lavoie, C., Gill, G. N., Insel, P. A., Huang, X. Y., and Farquhar, M. G. (2001) *Science* 294(5548), 1939-42.
22. Wang, Y., Zhou, Y., Szabo, K., Haft, C. R., and Trejo, J. (2002) *Mol Biol Cell* 13(6), 1965-76.
23. Wang, C., Deng, L., Hong, M., Akkaraju, G. R., Inoue, J., and Chen, Z. J. (2001) *Nature* 412(6844), 346-51.
24. Tohgo, A., Pierce, K. L., Choy, E. W., Lefkowitz, R. J., and Luttrell, L. M. (2002) *J Biol Chem* 277(11), 9429-36.
25. Molecular Biology of the Cell, Alberts, et al 4th edition copyright 2002, 359360
26. Shenoy, S., McDonald, P., Kohout, T., Lefkowitz, R. (2001) *Science* Vol 294, 1307-1313

What is claimed is:

1. An arrestin chimera comprising a naturally occurring beta-arrestin-2 and a naturally occurring ubiquitin moiety, wherein the arrestin chimera has an increased affinity for a GPCR, as compared to the affinity of a wild-type arrestin for a GPCR, and wherein increased affinity means that the arrestin chimera remains associated with the GPCR and traffics with the GPCR into endosomes, and wherein the arrestin chimera does not dissociate from the GPCR at or near the plasma membrane.

2. The arrestin chimera of claim 1, wherein the naturally occurring ubiquitin moiety or fragment of ubiquitin is fused in frame to the naturally occurring beta-arrestin-2.

3. The arrestin chimera of claim 1, wherein the naturally occurring ubiquitin moiety is not susceptible to deubiquitination.

4. The arrestin chimera of claim 1, wherein the naturally occurring ubiquitin moiety is linked to the 5' or 3' end of the arrestin.

5. The arrestin chimera of claim 1, wherein the chimera further comprises a label, and wherein the label is a radioisotope, an epitope tag, an affinity label, an enzyme, a fluorescent group, or a chemiluminescent group.

6. The arrestin chimera of claim 1, wherein the arrestin chimera comprises the amino acid sequence of SEQ ID NO:2.

7. The arrestin chimera of claim 1, wherein the ubiquitin moiety comprises one or more ubiquitin chains.

8. The arrestin chimera of claim 1, wherein the GPCR is a class A GPCR.

9. The arrestin chimera of claim 1, wherein the arrestin chimera increases the internalization of the GPCR.

* * * * *

SEQUENCE LISTING

```
<160> NUMBER OF SEQ ID NOS: 45

<210> SEQ ID NO 1
<211> LENGTH: 1581
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(1575)

<400> SEQUENCE: 1 ctg ctg gag ttc gtg acc gcc gcc ggg atc act ctc ggc atg gac gag      48
Leu Leu Glu Phe Val Thr Ala Ala Gly Ile Thr Leu Gly Met Asp Glu
1               5                   10                  15 ctg tac aag tcc gga ctc aga tct cga gct caa gct tcg aat tct gca      96
Leu Tyr Lys Ser Gly Leu Arg Ser Arg Ala Gln Ala Ser Asn Ser Ala
            20                  25                  30 gtc gac ggt acc acg cgc acc atg ggt gaa aaa ccc ggg acc agg gtc     144
Val Asp Gly Thr Thr Arg Thr Met Gly Glu Lys Pro Gly Thr Arg Val
        35                  40                  45 ttc aag aag tcg agc cct aac tgc aag ctc acc gtg tac ttg ggc aag     192
Phe Lys Lys Ser Ser Pro Asn Cys Lys Leu Thr Val Tyr Leu Gly Lys
    50                  55                  60 cgt gac ttt gtg gat cac ttg gac aaa gtg gat cct gtc gat ggt gtg     240
Arg Asp Phe Val Asp His Leu Asp Lys Val Asp Pro Val Asp Gly Val
65                  70                  75                  80 gtg ctt gtg gat cct gac tac ttg aag gac cgg aaa gtg ttt gtg acc     288
Val Leu Val Asp Pro Asp Tyr Leu Lys Asp Arg Lys Val Phe Val Thr
                85                  90                  95
```

| | | |
|---|---|---|
| ctc acc tgt gcc ttc cgc tat ggc cga gaa gac ctg gat gta ctg ggc<br>Leu Thr Cys Ala Phe Arg Tyr Gly Arg Glu Asp Leu Asp Val Leu Gly<br>100 105 110 | | 336 |
| ctg tct ttc cgc aaa gat ctg ttc atc gcc acc tac cag gcc ttc ccc<br>Leu Ser Phe Arg Lys Asp Leu Phe Ile Ala Thr Tyr Gln Ala Phe Pro<br>115 120 125 | | 384 |
| ccc atg ccc aac cca cct cgg ccc ccc acc cgc cta cag gac cga ctg<br>Pro Met Pro Asn Pro Pro Arg Pro Pro Thr Arg Leu Gln Asp Arg Leu<br>130 135 140 | | 432 |
| ctg aag aag ttg ggc cag cat gcc cac ccc ttt ttt ttc aca ata ccc<br>Leu Lys Lys Leu Gly Gln His Ala His Pro Phe Phe Phe Thr Ile Pro<br>145 150 155 160 | | 480 |
| cag aat ttg cct tgc tcc gtc aca ctg cag cca gga ccg gag gac aca<br>Gln Asn Leu Pro Cys Ser Val Thr Leu Gln Pro Gly Pro Glu Asp Thr<br>165 170 175 | | 528 |
| ggg aag gcc tgt gga gta gac ttt gag att cga gcc ttc tgt gcc aaa<br>Gly Lys Ala Cys Gly Val Asp Phe Glu Ile Arg Ala Phe Cys Ala Lys<br>180 185 190 | | 576 |
| tct ata gaa gaa aaa agc cac aaa agg aac tcc gtg cgg ctt atc atc<br>Ser Ile Glu Glu Lys Ser His Lys Arg Asn Ser Val Arg Leu Ile Ile<br>195 200 205 | | 624 |
| aga aag gta cag ttt gct cct gag aca ccc ggc ccc cag cca tca gct<br>Arg Lys Val Gln Phe Ala Pro Glu Thr Pro Gly Pro Gln Pro Ser Ala<br>210 215 220 | | 672 |
| gaa acc aca cgc cac ttc ctc atg tct gac cgg agg tcc ctg cac cta<br>Glu Thr Thr Arg His Phe Leu Met Ser Asp Arg Arg Ser Leu His Leu<br>225 230 235 240 | | 720 |
| gag gct tcc ctg gac aaa gag ctg tac tac cat ggg gaa ccc ctc aat<br>Glu Ala Ser Leu Asp Lys Glu Leu Tyr Tyr His Gly Glu Pro Leu Asn<br>245 250 255 | | 768 |
| gtc aac gtc cac gtc acc aac aat tct gcc aag acc gtc aag aag atc<br>Val Asn Val His Val Thr Asn Asn Ser Ala Lys Thr Val Lys Lys Ile<br>260 265 270 | | 816 |
| aga gtg tct gtg aga cag tat gcc gac att tgc ctc ttc agc acc gcg<br>Arg Val Ser Val Arg Gln Tyr Ala Asp Ile Cys Leu Phe Ser Thr Ala<br>275 280 285 | | 864 |
| cag tac aag tgt cct gtg gct cag ctt gaa caa gat gac cag gtg tct<br>Gln Tyr Lys Cys Pro Val Ala Gln Leu Glu Gln Asp Asp Gln Val Ser<br>290 295 300 | | 912 |
| ccc agt tcc aca ttc tgc aag gtg tac acc ata acc ccg ctg ctc agt<br>Pro Ser Ser Thr Phe Cys Lys Val Tyr Thr Ile Thr Pro Leu Leu Ser<br>305 310 315 320 | | 960 |
| gac aac cca gag aag cgt ggc ctt gcc ctt gat ggg caa ctc aag cac<br>Asp Asn Pro Glu Lys Arg Gly Leu Ala Leu Asp Gly Gln Leu Lys His<br>325 330 335 | | 1008 |
| caa gac acc aac ctg gct tcc agc acc att gtg aag gag gga gcc aac<br>Gln Asp Thr Asn Leu Ala Ser Ser Thr Ile Val Lys Glu Gly Ala Asn<br>340 345 350 | | 1056 |
| aag gag gtg ctg gga atc cta gta tcc tac agg gtc aac gtg aag ctg<br>Lys Glu Val Leu Gly Ile Leu Val Ser Tyr Arg Val Asn Val Lys Leu<br>355 360 365 | | 1104 |
| gtg gtg tct cca ggc ggc gat gtc tcc gtg gag cta cct ttc gtc cta<br>Val Val Ser Pro Gly Gly Asp Val Ser Val Glu Leu Pro Phe Val Leu<br>370 375 380 | | 1152 |
| atg cac ccc aag ccc cac gac cac atc acc ctt ccc cga ccc cag tca<br>Met His Pro Lys Pro His Asp His Ile Thr Leu Pro Arg Pro Gln Ser<br>385 390 395 400 | | 1200 |
| gcc ccc cgg gaa ata gac atc cct gtg gat acc aac ctc att gaa ttc<br>Ala Pro Arg Glu Ile Asp Ile Pro Val Asp Thr Asn Leu Ile Glu Phe | | 1248 |

-continued

```
                  405                 410                 415
gat acc aac tat gcc aca gac gac gac atc gtg ttt gag gac ttt gcg       1296
Asp Thr Asn Tyr Ala Thr Asp Asp Asp Ile Val Phe Glu Asp Phe Ala
            420                 425                 430 agg ctt cgg ctg aag ggg atg aag gat gac gac tgt gat gac cag ttc       1344
Arg Leu Arg Leu Lys Gly Met Lys Asp Asp Asp Cys Asp Asp Gln Phe
            435                 440                 445 tgc gtc gac cag atc ttc gtg aag act ctg act ggt aag acc atc acc       1392
Cys Val Asp Gln Ile Phe Val Lys Thr Leu Thr Gly Lys Thr Ile Thr
450                 455                 460 ctc gag gtg gag ccc agt gac acc atc gag aat gtc aag gca aag atc       1440
Leu Glu Val Glu Pro Ser Asp Thr Ile Glu Asn Val Lys Ala Lys Ile
465                 470                 475                 480 caa gat aag gaa ggc att cct cct gat cag cag agg ttg atc ttt gcc       1488
Gln Asp Lys Glu Gly Ile Pro Pro Asp Gln Gln Arg Leu Ile Phe Ala
                485                 490                 495 gga aaa cag ctg gaa gat ggt cgt acc ctg tct gac tac aac atc cag       1536
Gly Lys Gln Leu Glu Asp Gly Arg Thr Leu Ser Asp Tyr Asn Ile Gln
            500                 505                 510 aaa gag tcc acc ttg cac ctg gta ctc cgt ctc aga ggt gggtga            1581
Lys Glu Ser Thr Leu His Leu Val Leu Arg Leu Arg Gly
            515                 520                 525
```

<210> SEQ ID NO 2
<211> LENGTH: 525
<212> TYPE: PRT
<213> ORGANISM: Artificial
<220> FEATURE:
<223> OTHER INFORMATION: Synthetic Construct

<400> SEQUENCE: 2

```
Leu Leu Glu Phe Val Thr Ala Ala Gly Ile Thr Leu Gly Met Asp Glu
1               5                   10                  15

Leu Tyr Lys Ser Gly Leu Arg Ser Arg Ala Gln Ala Ser Asn Ser Ala
            20                  25                  30

Val Asp Gly Thr Thr Arg Thr Met Gly Glu Lys Pro Gly Thr Arg Val
        35                  40                  45

Phe Lys Lys Ser Ser Pro Asn Cys Lys Leu Thr Val Tyr Leu Gly Lys
    50                  55                  60

Arg Asp Phe Val Asp His Leu Asp Lys Val Asp Pro Val Asp Gly Val
65                  70                  75                  80

Val Leu Val Asp Pro Asp Tyr Leu Lys Asp Arg Lys Val Phe Val Thr
                85                  90                  95

Leu Thr Cys Ala Phe Arg Tyr Gly Arg Glu Asp Leu Asp Val Leu Gly
            100                 105                 110

Leu Ser Phe Arg Lys Asp Leu Phe Ile Ala Thr Tyr Gln Ala Phe Pro
        115                 120                 125

Pro Met Pro Asn Pro Pro Arg Pro Pro Thr Arg Leu Gln Asp Arg Leu
    130                 135                 140

Leu Lys Lys Leu Gly Gln His Ala His Pro Phe Phe Thr Ile Pro
145                 150                 155                 160

Gln Asn Leu Pro Cys Ser Val Thr Leu Gln Pro Gly Pro Glu Asp Thr
                165                 170                 175

Gly Lys Ala Cys Gly Val Asp Phe Glu Ile Arg Ala Phe Cys Ala Lys
            180                 185                 190

Ser Ile Glu Glu Lys Ser His Lys Arg Asn Ser Val Arg Leu Ile Ile
        195                 200                 205
```

```
Arg Lys Val Gln Phe Ala Pro Glu Thr Pro Gly Pro Gln Pro Ser Ala
    210                 215                 220

Glu Thr Thr Arg His Phe Leu Met Ser Asp Arg Arg Ser Leu His Leu
225                 230                 235                 240

Glu Ala Ser Leu Asp Lys Glu Leu Tyr Tyr His Gly Glu Pro Leu Asn
                245                 250                 255

Val Asn Val His Val Thr Asn Asn Ser Ala Lys Thr Val Lys Lys Ile
            260                 265                 270

Arg Val Ser Val Arg Gln Tyr Ala Asp Ile Cys Leu Phe Ser Thr Ala
        275                 280                 285

Gln Tyr Lys Cys Pro Val Ala Gln Leu Glu Gln Asp Gln Val Ser
    290                 295                 300

Pro Ser Ser Thr Phe Cys Lys Val Tyr Thr Ile Thr Pro Leu Leu Ser
305                 310                 315                 320

Asp Asn Pro Glu Lys Arg Gly Leu Ala Leu Asp Gly Gln Leu Lys His
                325                 330                 335

Gln Asp Thr Asn Leu Ala Ser Ser Thr Ile Val Lys Glu Gly Ala Asn
            340                 345                 350

Lys Glu Val Leu Gly Ile Leu Val Ser Tyr Arg Val Asn Val Lys Leu
        355                 360                 365

Val Val Ser Pro Gly Gly Asp Val Ser Val Glu Leu Pro Phe Val Leu
370                 375                 380

Met His Pro Lys Pro His Asp His Ile Thr Leu Pro Arg Pro Gln Ser
385                 390                 395                 400

Ala Pro Arg Glu Ile Asp Ile Pro Val Asp Thr Asn Leu Ile Glu Phe
                405                 410                 415

Asp Thr Asn Tyr Ala Thr Asp Asp Ile Val Phe Glu Asp Phe Ala
            420                 425                 430

Arg Leu Arg Leu Lys Gly Met Lys Asp Asp Cys Asp Asp Gln Phe
        435                 440                 445

Cys Val Asp Gln Ile Phe Val Lys Thr Leu Thr Gly Lys Thr Ile Thr
    450                 455                 460

Leu Glu Val Glu Pro Ser Asp Thr Ile Glu Asn Val Lys Ala Lys Ile
465                 470                 475                 480

Gln Asp Lys Glu Gly Ile Pro Pro Asp Gln Gln Arg Leu Ile Phe Ala
                485                 490                 495

Gly Lys Gln Leu Glu Asp Gly Arg Thr Leu Ser Asp Tyr Asn Ile Gln
            500                 505                 510

Lys Glu Ser Thr Leu His Leu Val Leu Arg Leu Arg Gly
        515                 520                 525

<210> SEQ ID NO 3
<211> LENGTH: 1581
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(1581)

<400> SEQUENCE: 3 ctg ctg gag ttc gtg acc gcc gcc ggg atc act ctc ggc atg gac gag     48
Leu Leu Glu Phe Val Thr Ala Ala Gly Ile Thr Leu Gly Met Asp Glu
1               5                   10                  15 ctg tac aag tcc gga ctc aga tct cga gct caa gct tcg aat tct gca     96
Leu Tyr Lys Ser Gly Leu Arg Ser Arg Ala Gln Ala Ser Asn Ser Ala
```

-continued

|  | 20 | 25 | 30 |  |
|---|---|---|---|---|
| gtc gac ggt acc acg cgc acc atg ggt gaa aaa ccc ggg acc agg gtc | | | | 144 |
| Val Asp Gly Thr Thr Arg Thr Met Gly Glu Lys Pro Gly Thr Arg Val | | | | |
| 35 | | 40 | 45 | |
| ttc aag aag tcg agc cct aac tgc aag ctc acc gtg tac ttg ggc aag | | | | 192 |
| Phe Lys Lys Ser Ser Pro Asn Cys Lys Leu Thr Val Tyr Leu Gly Lys | | | | |
| 50 | | 55 | 60 | |
| cgt gac ttt gtg gat cac ttg gac aaa gtg gat cct gtc gat ggt gtg | | | | 240 |
| Arg Asp Phe Val Asp His Leu Asp Lys Val Asp Pro Val Asp Gly Val | | | | |
| 65 | 70 | 75 | 80 | |
| gtg ctt gtg gat cct gac tac ttg aag gac cgg aaa gtg ttt gtg acc | | | | 288 |
| Val Leu Val Asp Pro Asp Tyr Leu Lys Asp Arg Lys Val Phe Val Thr | | | | |
| | 85 | 90 | 95 | |
| ctc acc tgt gcc ttc cgc tat ggc cga gaa gac ctg gat gta ctg ggc | | | | 336 |
| Leu Thr Cys Ala Phe Arg Tyr Gly Arg Glu Asp Leu Asp Val Leu Gly | | | | |
| | 100 | 105 | 110 | |
| ctg tct ttc cgc aaa gat ctg ttc atc gcc acc tac cag gcc ttc ccc | | | | 384 |
| Leu Ser Phe Arg Lys Asp Leu Phe Ile Ala Thr Tyr Gln Ala Phe Pro | | | | |
| | 115 | 120 | 125 | |
| ccc atg ccc aac cca cct cgg ccc ccc acc cgc cta cag gac cga ctg | | | | 432 |
| Pro Met Pro Asn Pro Pro Arg Pro Pro Thr Arg Leu Gln Asp Arg Leu | | | | |
| | 130 | 135 | 140 | |
| ctg aag aag ttg ggc cag cat gcc cac ccc ttt ttt ttc aca ata ccc | | | | 480 |
| Leu Lys Lys Leu Gly Gln His Ala His Pro Phe Phe Phe Thr Ile Pro | | | | |
| 145 | 150 | 155 | 160 | |
| cag aat ttg cct tgc tcc gtc aca ctg cag cca gca ccg gag gac aca | | | | 528 |
| Gln Asn Leu Pro Cys Ser Val Thr Leu Gln Pro Ala Pro Glu Asp Thr | | | | |
| | 165 | 170 | 175 | |
| ggg aag gcc tgt gga gta gac ttt gag att cga gcc ttc tgt gcc aaa | | | | 576 |
| Gly Lys Ala Cys Gly Val Asp Phe Glu Ile Arg Ala Phe Cys Ala Lys | | | | |
| | 180 | 185 | 190 | |
| tct ata gaa gaa aaa agc cac aaa agg aac tcc gtg cgg ctt atc atc | | | | 624 |
| Ser Ile Glu Glu Lys Ser His Lys Arg Asn Ser Val Arg Leu Ile Ile | | | | |
| | 195 | 200 | 205 | |
| aga aag gta cag ttt gct cct gag aca ccc ggc ccc cag cca tca gct | | | | 672 |
| Arg Lys Val Gln Phe Ala Pro Glu Thr Pro Gly Pro Gln Pro Ser Ala | | | | |
| 210 | | 215 | 220 | |
| gaa acc aca cgc cac ttc ctc atg tct gac cgg agg tcc ctg cac cta | | | | 720 |
| Glu Thr Thr Arg His Phe Leu Met Ser Asp Arg Arg Ser Leu His Leu | | | | |
| 225 | | 230 | 235 | 240 |
| gag gct tcc ctg gac aaa gag ctg tac tac cat ggg gaa ccc ctc aat | | | | 768 |
| Glu Ala Ser Leu Asp Lys Glu Leu Tyr Tyr His Gly Glu Pro Leu Asn | | | | |
| | 245 | 250 | 255 | |
| gtc aac gtc cac gtc acc aac aat tct gcc aag acc gtc aag aag atc | | | | 816 |
| Val Asn Val His Val Thr Asn Asn Ser Ala Lys Thr Val Lys Lys Ile | | | | |
| | 260 | 265 | 270 | |
| aga gtg tct gtg aga cag tat gcc gac att tgc ctc ttc agc acc gcg | | | | 864 |
| Arg Val Ser Val Arg Gln Tyr Ala Asp Ile Cys Leu Phe Ser Thr Ala | | | | |
| | 275 | 280 | 285 | |
| cag tac aag tgt cct gtg gct cag ctt gaa caa gat gac cag gtg tct | | | | 912 |
| Gln Tyr Lys Cys Pro Val Ala Gln Leu Glu Gln Asp Asp Gln Val Ser | | | | |
| | 290 | 295 | 300 | |
| ccc agt tcc aca ttc tgc aag gtg tac acc ata acc ccg ctg ctc agt | | | | 960 |
| Pro Ser Ser Thr Phe Cys Lys Val Tyr Thr Ile Thr Pro Leu Leu Ser | | | | |
| 305 | | 310 | 315 | 320 |
| gac aac cga gag aag cgt ggc ctt gcc ctt gat ggg caa ctc aag cac | | | | 1008 |
| Asp Asn Arg Glu Lys Arg Gly Leu Ala Leu Asp Gly Gln Leu Lys His | | | | |
| | 325 | 330 | 335 | |
| gaa gac acc aac ctg gct tcc agc acc att gtg aag gag gga ccc aac | | | | 1056 |

```
Glu Asp Thr Asn Leu Ala Ser Ser Thr Ile Val Lys Glu Gly Pro Asn
            340                 345                 350 aac gag gtg ctg gga atc cta gta tcc tac agc gtc aag ctg aag ctg      1104
Asn Glu Val Leu Gly Ile Leu Val Ser Tyr Ser Val Lys Leu Lys Leu
        355                 360                 365 gtg gtg tct cga cgc ggg gat gtc tcc gtg gag cta cct ttc ctc cta      1152
Val Val Ser Arg Arg Gly Asp Val Ser Val Glu Leu Pro Phe Leu Leu
    370                 375                 380 atg cac ccc aag ccc cac cac cac atc acc ctt ccc cga ccc cag tca      1200
Met His Pro Lys Pro His His His Ile Thr Leu Pro Arg Pro Gln Ser
385                 390                 395                 400 gcc ccc cgg gaa ata gac atc cct gtg gat acc aac ctc att gaa ttc      1248
Ala Pro Arg Glu Ile Asp Ile Pro Val Asp Thr Asn Leu Ile Glu Phe
                405                 410                 415 gat acc aac tat gcc aca gac gac gac atc gtg ttt gag gac ttt gcg      1296
Asp Thr Asn Tyr Ala Thr Asp Asp Asp Ile Val Phe Glu Asp Phe Ala
            420                 425                 430 agg ctt cgg ctg aag ggg atg aag gat gac gac tct gat gac cag ttc      1344
Arg Leu Arg Leu Lys Gly Met Lys Asp Asp Asp Ser Asp Asp Gln Phe
        435                 440                 445 tgc gtc gac cag att ttc gtc aag act ttg acc ggt aaa acc ata aca      1392
Cys Val Asp Gln Ile Phe Val Lys Thr Leu Thr Gly Lys Thr Ile Thr
    450                 455                 460 ttg gaa gtt gaa tct tcc gat acc atc gac aac gtt aag tcg aaa att      1440
Leu Glu Val Glu Ser Ser Asp Thr Ile Asp Asn Val Lys Ser Lys Ile
465                 470                 475                 480 caa gac aag gaa ggt atc cct cca gat caa caa aga ttg atc ttt gcc      1488
Gln Asp Lys Glu Gly Ile Pro Pro Asp Gln Gln Arg Leu Ile Phe Ala
                485                 490                 495 ggt agg cag cta gaa gac ggt aga acg ctg tct gat tac aac att cag      1536
Gly Arg Gln Leu Glu Asp Gly Arg Thr Leu Ser Asp Tyr Asn Ile Gln
            500                 505                 510 aag gag tcc acc tta cat ctt gtg cta agg cta aga ggt ggt tga          1581
Lys Glu Ser Thr Leu His Leu Val Leu Arg Leu Arg Gly Gly
        515                 520                 525

<210> SEQ ID NO 4
<211> LENGTH: 526
<212> TYPE: PRT
<213> ORGANISM: Artificial
<220> FEATURE:
<223> OTHER INFORMATION: Synthetic Construct

<400> SEQUENCE: 4

Leu Leu Glu Phe Val Thr Ala Ala Gly Ile Thr Leu Gly Met Asp Glu
1               5                   10                  15

Leu Tyr Lys Ser Gly Leu Arg Ser Arg Ala Gln Ala Ser Asn Ser Ala
            20                  25                  30

Val Asp Gly Thr Thr Arg Thr Met Gly Glu Lys Pro Gly Thr Arg Val
        35                  40                  45

Phe Lys Lys Ser Ser Pro Asn Cys Lys Leu Thr Val Tyr Leu Gly Lys
    50                  55                  60

Arg Asp Phe Val Asp His Leu Asp Lys Val Asp Pro Val Asp Gly Val
65                  70                  75                  80

Val Leu Val Asp Pro Asp Tyr Leu Lys Asp Arg Lys Val Phe Val Thr
                85                  90                  95

Leu Thr Cys Ala Phe Arg Tyr Gly Arg Glu Asp Leu Asp Val Leu Gly
            100                 105                 110

Leu Ser Phe Arg Lys Asp Leu Phe Ile Ala Thr Tyr Gln Ala Phe Pro
```

```
                115              120              125
    Pro Met Pro Asn Pro Pro Arg Pro Pro Thr Arg Leu Gln Asp Arg Leu
        130                 135                 140
    Leu Lys Lys Leu Gly Gln His Ala His Pro Phe Phe Thr Ile Pro
    145                 150                 155                 160
    Gln Asn Leu Pro Cys Ser Val Thr Leu Gln Pro Ala Pro Glu Asp Thr
                    165                 170                 175
    Gly Lys Ala Cys Gly Val Asp Phe Glu Ile Arg Ala Phe Cys Ala Lys
                180                 185                 190
    Ser Ile Glu Glu Lys Ser His Lys Arg Asn Ser Val Arg Leu Ile Ile
            195                 200                 205
    Arg Lys Val Gln Phe Ala Pro Glu Thr Pro Gly Pro Gln Pro Ser Ala
        210                 215                 220
    Glu Thr Thr Arg His Phe Leu Met Ser Asp Arg Ser Leu His Leu
    225                 230                 235                 240
    Glu Ala Ser Leu Asp Lys Glu Leu Tyr Tyr His Gly Glu Pro Leu Asn
                    245                 250                 255
    Val Asn Val His Val Thr Asn Asn Ser Ala Lys Thr Val Lys Lys Ile
                260                 265                 270
    Arg Val Ser Val Arg Gln Tyr Ala Asp Ile Cys Leu Phe Ser Thr Ala
            275                 280                 285
    Gln Tyr Lys Cys Pro Val Ala Gln Leu Glu Gln Asp Asp Gln Val Ser
        290                 295                 300
    Pro Ser Ser Thr Phe Cys Lys Val Tyr Thr Ile Thr Pro Leu Leu Ser
    305                 310                 315                 320
    Asp Asn Arg Glu Lys Arg Gly Leu Ala Leu Asp Gly Gln Leu Lys His
                    325                 330                 335
    Glu Asp Thr Asn Leu Ala Ser Ser Thr Ile Val Lys Glu Gly Pro Asn
                340                 345                 350
    Asn Glu Val Leu Gly Ile Leu Val Ser Tyr Ser Val Lys Leu Lys Leu
            355                 360                 365
    Val Val Ser Arg Arg Gly Asp Val Ser Val Glu Leu Pro Phe Leu Leu
        370                 375                 380
    Met His Pro Lys Pro His His Ile Thr Leu Pro Arg Pro Gln Ser
    385                 390                 395                 400
    Ala Pro Arg Glu Ile Asp Ile Pro Val Asp Thr Asn Leu Ile Glu Phe
                    405                 410                 415
    Asp Thr Asn Tyr Ala Thr Asp Asp Ile Val Phe Glu Asp Phe Ala
                420                 425                 430
    Arg Leu Arg Leu Lys Gly Met Lys Asp Asp Ser Asp Asp Gln Phe
            435                 440                 445
    Cys Val Asp Gln Ile Phe Val Lys Thr Leu Thr Gly Lys Thr Ile Thr
        450                 455                 460
    Leu Glu Val Glu Ser Ser Asp Thr Ile Asp Asn Val Lys Ser Lys Ile
    465                 470                 475                 480
    Gln Asp Lys Glu Gly Ile Pro Pro Asp Gln Gln Arg Leu Ile Phe Ala
                    485                 490                 495
    Gly Arg Gln Leu Glu Asp Gly Arg Thr Leu Ser Asp Tyr Asn Ile Gln
                500                 505                 510
    Lys Glu Ser Thr Leu His Leu Val Leu Arg Leu Arg Gly Gly
            515                 520                 525

<210> SEQ ID NO 5
```

<211> LENGTH: 1578
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(1578)

<400> SEQUENCE: 5

```
ctg ctg gag ttc gtg acc gcc gcc ggg atc act ctc ggc atg gac gag      48
Leu Leu Glu Phe Val Thr Ala Ala Gly Ile Thr Leu Gly Met Asp Glu
1               5                   10                  15 ctg tac aag tcc gga ctc aga tct cga gct caa gct tcg aat tct gca      96
Leu Tyr Lys Ser Gly Leu Arg Ser Arg Ala Gln Ala Ser Asn Ser Ala
            20                  25                  30 gtc gac ggt acc acg cgc acc atg ggt gaa aaa ccc ggg acc agg gtc     144
Val Asp Gly Thr Thr Arg Thr Met Gly Glu Lys Pro Gly Thr Arg Val
        35                  40                  45 ttc aag aag tcg agc cct aac tgc aag ctc acc gtg tac ttg ggc aag     192
Phe Lys Lys Ser Ser Pro Asn Cys Lys Leu Thr Val Tyr Leu Gly Lys
    50                  55                  60 cgt gac ttt gtg gat cac ttg gac aaa gtg gat cct gtc gat ggt gtg     240
Arg Asp Phe Val Asp His Leu Asp Lys Val Asp Pro Val Asp Gly Val
65                  70                  75                  80 gtg ctt gtg gat cct gac tac ttg aag gac cgg aaa gtg ttt gtg acc     288
Val Leu Val Asp Pro Asp Tyr Leu Lys Asp Arg Lys Val Phe Val Thr
                85                  90                  95 ctc acc tgt gcc ttc cgc tat ggc cga gaa gac ctg gat gta ctg ggc     336
Leu Thr Cys Ala Phe Arg Tyr Gly Arg Glu Asp Leu Asp Val Leu Gly
            100                 105                 110 ctg tct ttc cgc aaa gat ctg ttc atc gcc acc tac cag gcc ttc ccc     384
Leu Ser Phe Arg Lys Asp Leu Phe Ile Ala Thr Tyr Gln Ala Phe Pro
        115                 120                 125 ccc atg ccc aac cca cct cgg ccc ccc acc cgc cta cag gac cga ctg     432
Pro Met Pro Asn Pro Pro Arg Pro Pro Thr Arg Leu Gln Asp Arg Leu
    130                 135                 140 ctg aag aag ttg ggc cag cat gcc cac ccc ttt ttt ttc aca ata ccc     480
Leu Lys Lys Leu Gly Gln His Ala His Pro Phe Phe Phe Thr Ile Pro
145                 150                 155                 160 cag aat ttg cct tgc tcc gtc aca ctg cag cca gga ccg gag cac aca     528
Gln Asn Leu Pro Cys Ser Val Thr Leu Gln Pro Gly Pro Glu His Thr
                165                 170                 175 gcc aag gcc tgt gga gta gac ttt gag att cga gcc ttc tgt gcc aaa     576
Ala Lys Ala Cys Gly Val Asp Phe Glu Ile Arg Ala Phe Cys Ala Lys
            180                 185                 190 tct ata gaa caa aaa agc cac aaa agg aac tcc gtg cgg ctt atc atc     624
Ser Ile Glu Gln Lys Ser His Lys Arg Asn Ser Val Arg Leu Ile Ile
        195                 200                 205 aga aag gta cag ttt gct cct gag aca ccc ggc ccc cag cca tca gct     672
Arg Lys Val Gln Phe Ala Pro Glu Thr Pro Gly Pro Gln Pro Ser Ala
    210                 215                 220 gaa acc aca cgc cac ttc ctc atg tct gac cgg agg tcc ctg cac cta     720
Glu Thr Thr Arg His Phe Leu Met Ser Asp Arg Arg Ser Leu His Leu
225                 230                 235                 240 gag gct tcc ctg gac aaa gag ctg tac tac cat ggg gaa ccc ctc aat     768
Glu Ala Ser Leu Asp Lys Glu Leu Tyr Tyr His Gly Glu Pro Leu Asn
                245                 250                 255 gtc aac gtc cac gtc acc aac aat tct gcc aag acc gtc aag aag atc     816
Val Asn Val His Val Thr Asn Asn Ser Ala Lys Thr Val Lys Lys Ile
            260                 265                 270
```

```
aga gtg tct gtg aga cag tat gcc gac att tgc ctc ttc agc acc gcg      864
Arg Val Ser Val Arg Gln Tyr Ala Asp Ile Cys Leu Phe Ser Thr Ala
    275                 280                 285 cag tac aag tgt cct gtg gct cag ctt gaa caa gat gac cag gtg tct      912
Gln Tyr Lys Cys Pro Val Ala Gln Leu Glu Gln Asp Asp Gln Val Ser
290                 295                 300 ccc agt tcc aca ttc tgc aag gtg tac acc ata ccg ctg ctc act          960
Pro Ser Ser Thr Phe Cys Lys Val Tyr Thr Ile Thr Pro Leu Leu Thr
305                 310                 315                 320 gac aac cga gag aag cgt ggc ctt gcc ctt cat ggg caa ctc aac cac     1008
Asp Asn Arg Glu Lys Arg Gly Leu Ala Leu His Gly Gln Leu Asn His
                325                 330                 335 gaa cac acc aac ctg gct tcc agc acc att gtg aag gag gga gcc aac     1056
Glu His Thr Asn Leu Ala Ser Ser Thr Ile Val Lys Glu Gly Ala Asn
            340                 345                 350 gag gtc ctg gga atc cta gta tcc tac agg gtc aag gtg aag ctg gtg     1104
Glu Val Leu Gly Ile Leu Val Ser Tyr Arg Val Lys Val Lys Leu Val
        355                 360                 365 gtg tct cca ggc ggg gat ctc tcc gtg gag cta cct ttc gtc cta atg     1152
Val Ser Pro Gly Gly Asp Leu Ser Val Glu Leu Pro Phe Val Leu Met
    370                 375                 380 cac ccc aag ccc cac cac cac atc acc ctt ccc cca ccc cag tca gcc     1200
His Pro Lys Pro His His His Ile Thr Leu Pro Pro Pro Gln Ser Ala
385                 390                 395                 400 ccc cgg gaa ata gac atc cct gtg gat acc aac ctc att gaa ttc gat     1248
Pro Arg Glu Ile Asp Ile Pro Val Asp Thr Asn Leu Ile Glu Phe Asp
                405                 410                 415 acc aac tat gcc aca gac gac gac atc gtg ttt gag gac ttt gcg agg     1296
Thr Asn Tyr Ala Thr Asp Asp Asp Ile Val Phe Glu Asp Phe Ala Arg
            420                 425                 430 ctt cgg ctg aag ggg atg aag gat gac gac tgt gat gac cag ttc tgc     1344
Leu Arg Leu Lys Gly Met Lys Asp Asp Asp Cys Asp Asp Gln Phe Cys
        435                 440                 445 gtc gac cag atc ttc gtg aag act ctg act ggt aag acc atc acc ctc     1392
Val Asp Gln Ile Phe Val Lys Thr Leu Thr Gly Lys Thr Ile Thr Leu
    450                 455                 460 gag gtg gag ccc agt gac acc atc gag aat gtc aag gca aag atc caa     1440
Glu Val Glu Pro Ser Asp Thr Ile Glu Asn Val Lys Ala Lys Ile Gln
465                 470                 475                 480 gat aag gaa ggc att cct cct gat cag cag agg ttg atc ttt gcc gga     1488
Asp Lys Glu Gly Ile Pro Pro Asp Gln Gln Arg Leu Ile Phe Ala Gly
                485                 490                 495 aga cag ctg gaa gat ggt cgt acc ctg tct gac tac aac atc cag aaa     1536
Arg Gln Leu Glu Asp Gly Arg Thr Leu Ser Asp Tyr Asn Ile Gln Lys
            500                 505                 510 gag tcc acc ttg cac ctg gta ctc cgt ctc aga ggt ggg tga             1578
Glu Ser Thr Leu His Leu Val Leu Arg Leu Arg Gly Gly
        515                 520                 525

<210> SEQ ID NO 6
<211> LENGTH: 525
<212> TYPE: PRT
<213> ORGANISM: Artificial
<220> FEATURE:
<223> OTHER INFORMATION: Synthetic Construct

<400> SEQUENCE: 6

Leu Leu Glu Phe Val Thr Ala Ala Gly Ile Thr Leu Gly Met Asp Glu
1               5                   10                  15

Leu Tyr Lys Ser Gly Leu Arg Ser Arg Ala Gln Ala Ser Asn Ser Ala
            20                  25                  30
```

-continued

```
Val Asp Gly Thr Thr Arg Thr Met Gly Glu Lys Pro Gly Thr Arg Val
        35                  40                  45

Phe Lys Lys Ser Ser Pro Asn Cys Lys Leu Thr Val Tyr Leu Gly Lys
 50                  55                  60

Arg Asp Phe Val Asp His Leu Asp Lys Val Asp Pro Val Asp Gly Val
 65                  70                  75                  80

Val Leu Val Asp Pro Asp Tyr Leu Lys Asp Arg Lys Val Phe Val Thr
                 85                  90                  95

Leu Thr Cys Ala Phe Arg Tyr Gly Arg Glu Asp Leu Asp Val Leu Gly
            100                 105                 110

Leu Ser Phe Arg Lys Asp Leu Phe Ile Ala Thr Tyr Gln Ala Phe Pro
        115                 120                 125

Pro Met Pro Asn Pro Pro Arg Pro Thr Arg Leu Gln Asp Arg Leu
        130                 135                 140

Leu Lys Lys Leu Gly Gln His Ala His Pro Phe Phe Thr Ile Pro
145                 150                 155                 160

Gln Asn Leu Pro Cys Ser Val Thr Leu Gln Pro Gly Pro Glu His Thr
                165                 170                 175

Ala Lys Ala Cys Gly Val Asp Phe Glu Ile Arg Ala Phe Cys Ala Lys
            180                 185                 190

Ser Ile Glu Gln Lys Ser His Lys Arg Asn Ser Val Arg Leu Ile Ile
        195                 200                 205

Arg Lys Val Gln Phe Ala Pro Glu Thr Pro Gly Pro Gln Pro Ser Ala
    210                 215                 220

Glu Thr Thr Arg His Phe Leu Met Ser Asp Arg Arg Ser Leu His Leu
225                 230                 235                 240

Glu Ala Ser Leu Asp Lys Glu Leu Tyr Tyr His Gly Glu Pro Leu Asn
                245                 250                 255

Val Asn Val His Val Thr Asn Asn Ser Ala Lys Thr Val Lys Lys Ile
            260                 265                 270

Arg Val Ser Val Arg Gln Tyr Ala Asp Ile Cys Leu Phe Ser Thr Ala
        275                 280                 285

Gln Tyr Lys Cys Pro Val Ala Gln Leu Glu Gln Asp Asp Gln Val Ser
    290                 295                 300

Pro Ser Ser Thr Phe Cys Lys Val Tyr Thr Ile Thr Pro Leu Leu Thr
305                 310                 315                 320

Asp Asn Arg Glu Lys Arg Gly Leu Ala Leu His Gly Gln Leu Asn His
                325                 330                 335

Glu His Thr Asn Leu Ala Ser Ser Thr Ile Val Lys Glu Gly Ala Asn
            340                 345                 350

Glu Val Leu Gly Ile Leu Val Ser Tyr Arg Val Lys Val Lys Leu Val
        355                 360                 365

Val Ser Pro Gly Gly Asp Leu Ser Val Glu Leu Pro Phe Val Leu Met
    370                 375                 380

His Pro Lys Pro His His Ile Thr Leu Pro Pro Gln Ser Ala
385                 390                 395                 400

Pro Arg Glu Ile Asp Ile Pro Val Asp Thr Asn Leu Ile Glu Phe Asp
                405                 410                 415

Thr Asn Tyr Ala Thr Asp Asp Ile Val Phe Glu Asp Phe Ala Arg
            420                 425                 430

Leu Arg Leu Lys Gly Met Lys Asp Asp Cys Asp Asp Gln Phe Cys
        435                 440                 445
```

```
Val Asp Gln Ile Phe Val Lys Thr Leu Thr Gly Lys Thr Ile Thr Leu
    450                 455                 460

Glu Val Glu Pro Ser Asp Thr Ile Glu Asn Val Lys Ala Lys Ile Gln
465                 470                 475                 480

Asp Lys Glu Gly Ile Pro Pro Asp Gln Gln Arg Leu Ile Phe Ala Gly
                485                 490                 495

Arg Gln Leu Glu Asp Gly Arg Thr Leu Ser Asp Tyr Asn Ile Gln Lys
            500                 505                 510

Glu Ser Thr Leu His Leu Val Leu Arg Leu Arg Gly Gly
        515                 520                 525
```

<210> SEQ ID NO 7
<211> LENGTH: 43
<212> TYPE: PRT
<213> ORGANISM: Homo sapiens

<400> SEQUENCE: 7

```
Asn Pro Ile Val Tyr Ala Phe Arg Ile Gly Lys Phe Arg Val Thr Phe
1               5                   10                  15

Leu Lys Ile Trp Asn Asp His Phe Arg Cys Gln Pro Ala Pro Pro Ile
            20                  25                  30

Asp Glu Asp Ile Pro Glu Glu Arg Pro Asp
        35                  40
```

<210> SEQ ID NO 8
<211> LENGTH: 177
<212> TYPE: PRT
<213> ORGANISM: Homo sapiens

<400> SEQUENCE: 8

```
Asn Pro Ile Ile Tyr Pro Glu Ser Ser Lys Glu Phe Lys Arg Ala Phe
1               5                   10                  15

Val Arg Ile Leu Gly Glu Gly Cys Arg Gly Arg Gly Arg Arg Arg
            20                  25                  30

Arg Arg Arg Arg Arg Leu Gly Gly Cys Ala Tyr Thr Tyr Arg Pro Trp
        35                  40                  45

Thr Arg Gly Gly Ser Leu Glu Arg Ser Gly Ser Arg Lys Asp Ser Leu
    50                  55                  60

Asp Asp Ser Gly Ser Cys Leu Ser Gly Ser Gln Leu Thr Leu Pro Ser
65                  70                  75                  80

Ala Ser Pro Ser Pro Gly Tyr Leu Gly Arg Gly Ala Pro Pro Val
                85                  90                  95

Glu Leu Cys Ala Phe Pro Glu Trp Lys Ala Pro Gly Ala Leu Leu Ser
            100                 105                 110

Ile Pro Ala Pro Glu Pro Pro Gly Arg Arg Gly Arg His Asp Ser Gly
        115                 120                 125

Pro Leu Phe Thr Phe Lys Leu Leu Thr Glu Pro Glu Ser Pro Gly Thr
    130                 135                 140

Asp Gly Gly Ala Ser Asn Gly Gly Cys Glu Ala Ala Asp Val Ala
145                 150                 155                 160

Asn Gly Gly Pro Gly Phe Lys Ser Met Asn Pro Leu Ala Pro Gly Gln
                165                 170                 175

Phe
```

<210> SEQ ID NO 9
<211> LENGTH: 30
<212> TYPE: PRT

<213> ORGANISM: Homo sapiens

<400> SEQUENCE: 9

Asn Pro Val Ile Tyr Thr Ile Phe Asn His Asp Phe Arg Arg Ala Phe
1               5                   10                  15

Lys Lys Ile Leu Cys Arg Gly Asp Arg Leu Cys Arg Ile Val
            20                  25                  30

<210> SEQ ID NO 10
<211> LENGTH: 29
<212> TYPE: PRT
<213> ORGANISM: Homo sapiens

<400> SEQUENCE: 10

Asn Pro Val Ile Tyr Thr Ile Phe Asn Gln Asp Phe Arg Arg Ala Phe
1               5                   10                  15

Arg Arg Ile Leu Cys Arg Pro Trp Thr Gln Thr Ala Trp
            20                  25

<210> SEQ ID NO 11
<211> LENGTH: 30
<212> TYPE: PRT
<213> ORGANISM: Homo sapiens

<400> SEQUENCE: 11

Asn Pro Val Ile Tyr Thr Val Phe Asn Gln Asp Phe Arg Pro Ser Phe
1               5                   10                  15

Lys His Ile Leu Phe Arg Arg Arg Arg Gly Phe Arg Gln
            20                  25                  30

<210> SEQ ID NO 12
<211> LENGTH: 105
<212> TYPE: PRT
<213> ORGANISM: Homo sapiens

<400> SEQUENCE: 12

Asn Pro Ile Ile Tyr Cys Arg Ser Pro Asp Phe Arg Lys Ala Phe Gln
1               5                   10                  15

Gly Leu Leu Cys Cys Ala Arg Arg Ala Ala Arg Arg Arg His Ala Thr
            20                  25                  30

His Gly Asp Arg Pro Arg Ala Ser Gly Cys Leu Ala Arg Pro Gly Pro
        35                  40                  45

Pro Pro Ser Pro Gly Ala Ala Ser Asp Asp Asp Asp Asp Val Val
    50                  55                  60

Gly Ala Thr Pro Pro Ala Arg Leu Leu Glu Pro Trp Ala Gly Cys Asn
65                  70                  75                  80

Gly Gly Ala Ala Ala Asp Ser Asp Ser Ser Leu Asp Glu Pro Cys Arg
                85                  90                  95

Pro Gly Phe Ala Ser Glu Ser Lys Val
            100                 105

<210> SEQ ID NO 13
<211> LENGTH: 92
<212> TYPE: PRT
<213> ORGANISM: Homo sapiens

<400> SEQUENCE: 13

Asn Pro Leu Ile Tyr Cys Arg Ser Pro Asp Phe Arg Ile Ala Phe Gln
1               5                   10                  15

Glu Leu Leu Cys Leu Arg Arg Ser Ser Leu Lys Ala Tyr Gly Asn Gly

```
            20                  25                  30
Tyr Ser Ser Asn Gly Asn Thr Gly Glu Gln Ser Gly Tyr His Val Glu
        35                  40                  45
Gly Glu Lys Glu Asn Lys Leu Leu Cys Glu Asp Leu Pro Gly Thr Glu
    50                  55                  60
Asp Phe Val Gly His Gln Gly Thr Val Pro Ser Asp Asn Ile Asp Ser
65                  70                  75                  80
Gln Gly Arg Asn Cys Ser Thr Asn Asp Ser Leu Leu
                85                  90

<210> SEQ ID NO 14
<211> LENGTH: 120
<212> TYPE: PRT
<213> ORGANISM: Homo sapiens

<400> SEQUENCE: 14

Asn Pro Ile Ile Tyr Ala Phe Asn Ala Asp Phe Arg Lys Ala Phe Ser
1               5                   10                  15
Thr Leu Leu Gly Cys Tyr Arg Leu Cys Pro Ala Thr Asn Asn Ala Ile
            20                  25                  30
Glu Thr Val Ser Ile Asn Asn Asn Gly Ala Ala Met Phe Ser Ser His
        35                  40                  45
His Glu Pro Arg Gly Ser Ile Ser Lys Glu Cys Asn Leu Val Tyr Leu
    50                  55                  60
Ile Pro His Ala Val Gly Ser Ser Glu Asp Leu Lys Lys Glu Glu Ala
65                  70                  75                  80
Ala Gly Ile Ala Arg Pro Leu Glu Lys Leu Ser Pro Ala Leu Ser Val
                85                  90                  95
Ile Leu Asp Tyr Asp Thr Asp Val Ser Leu Glu Lys Ile Gln Pro Ile
            100                 105                 110
Thr Gln Asn Gly Gln His Pro Thr
        115                 120

<210> SEQ ID NO 15
<211> LENGTH: 22
<212> TYPE: PRT
<213> ORGANISM: Homo sapiens

<400> SEQUENCE: 15

Asn Pro Ile Ile Tyr Thr Thr Phe Asn Ile Glu Phe Arg Lys Ala Phe
1               5                   10                  15
Leu Lys Ile Leu His Cys
            20

<210> SEQ ID NO 16
<211> LENGTH: 22
<212> TYPE: PRT
<213> ORGANISM: Homo sapiens

<400> SEQUENCE: 16

Asn Pro Val Ile Tyr Thr Thr Phe Asn Ile Glu Phe Arg Lys Ala Phe
1               5                   10                  15
Leu Lys Ile Leu Ser Cys
            20

<210> SEQ ID NO 17
<211> LENGTH: 24
<212> TYPE: PRT
<213> ORGANISM: Homo sapiens
```

```
<400> SEQUENCE: 17

Asn Pro Val Ile Tyr Thr Val Phe His Ala Glu Phe Arg Asn Val Phe
1               5                   10                  15

Arg Lys Ala Leu Arg Ala Cys Cys
            20

<210> SEQ ID NO 18
<211> LENGTH: 123
<212> TYPE: PRT
<213> ORGANISM: Homo sapiens

<400> SEQUENCE: 18

Asn Pro Val Ile Tyr Ala Phe Asn Ala Asp Phe Gln Lys Val Phe Ala
1               5                   10                  15

Gln Leu Leu Gly Cys Ser His Phe Cys Ser Arg Thr Pro Val Glu Thr
            20                  25                  30

Val Asn Ile Ser Asn Glu Leu Ile Ser Tyr Asn Gln Asp Ile Val Phe
        35                  40                  45

His Lys Glu Ile Ala Ala Ala Tyr Ile His Met Met Pro Asn Ala Val
    50                  55                  60

Thr Pro Gly Asn Arg Glu Val Asp Asn Asp Glu Glu Gly Pro Phe
65                  70                  75                  80

Asp Arg Met Phe Gln Ile Tyr Gln Thr Ser Pro Asp Gly Asp Pro Val
                85                  90                  95

Ala Glu Ser Val Trp Glu Leu Asp Cys Glu Gly Glu Ile Ser Leu Asp
            100                 105                 110

Lys Ile Thr Pro Phe Thr Pro Asn Gly Phe His
        115                 120

<210> SEQ ID NO 19
<211> LENGTH: 47
<212> TYPE: PRT
<213> ORGANISM: Homo sapiens

<400> SEQUENCE: 19

Asn Pro Met Cys Tyr Ala Leu Cys Asn Lys Ala Phe Arg Asp Thr Phe
1               5                   10                  15

Arg Leu Leu Leu Leu Cys Arg Trp Asp Lys Arg Trp Arg Lys Ile
            20                  25                  30

Pro Lys Arg Pro Gly Ser Val His Arg Thr Pro Ser Arg Gln Cys
        35                  40                  45

<210> SEQ ID NO 20
<211> LENGTH: 31
<212> TYPE: PRT
<213> ORGANISM: Homo sapiens

<400> SEQUENCE: 20

Asn Pro Ala Cys Tyr Ala Leu Cys Asn Ala Thr Phe Lys Lys Thr Phe
1               5                   10                  15

Lys His Leu His Met Cys His Tyr Lys Asn Ile Gly Ala Thr Arg
            20                  25                  30

<210> SEQ ID NO 21
<211> LENGTH: 50
<212> TYPE: PRT
<213> ORGANISM: Homo sapiens

<400> SEQUENCE: 21
```

```
Asn Pro Val Cys Tyr Ala Leu Cys Asn Lys Thr Phe Arg Thr Thr Phe
1               5                   10                  15

Met Leu Leu Cys Gln Cys Asp Lys Lys Arg Arg Lys Gln Gln
            20                  25                  30

Tyr Gln Gln Arg Gln Ser Val Ile Phe His Lys Arg Ala Pro Glu Gln
                35                  40                  45

Ala Leu
    50

<210> SEQ ID NO 22
<211> LENGTH: 31
<212> TYPE: PRT
<213> ORGANISM: Homo sapiens

<400> SEQUENCE: 22

Asn Pro Ala Cys Tyr Ala Leu Cys Asn Ala Thr Phe Lys Lys Thr Phe
1               5                   10                  15

Arg His Leu Leu Leu Cys Gln Tyr Arg Asn Ile Gly Thr Ala Arg
            20                  25                  30

<210> SEQ ID NO 23
<211> LENGTH: 42
<212> TYPE: PRT
<213> ORGANISM: Homo sapiens

<400> SEQUENCE: 23

Asn Pro Ile Cys Tyr Ala Leu Cys Asn Arg Thr Phe Arg Lys Thr Phe
1               5                   10                  15

Lys Met Leu Leu Leu Cys Arg Trp Lys Lys Lys Val Glu Glu Lys
            20                  25                  30

Leu Tyr Trp Gln Gly Asn Ser Lys Leu Pro
            35                  40

<210> SEQ ID NO 24
<211> LENGTH: 24
<212> TYPE: PRT
<213> ORGANISM: Homo sapiens

<400> SEQUENCE: 24

Asn Pro Val Ile Tyr Ala Tyr Phe Asn Lys Asp Phe Gln Asn Ala Phe
1               5                   10                  15

Lys Lys Ile Ile Lys Cys Lys Phe
            20

<210> SEQ ID NO 25
<211> LENGTH: 26
<212> TYPE: PRT
<213> ORGANISM: Homo sapiens

<400> SEQUENCE: 25

Asn Pro Ile Ile Tyr Thr Met Ser Asn Glu Asp Phe Lys Gln Ala Phe
1               5                   10                  15

His Lys Leu Ile Arg Phe Lys Cys Thr Ser
            20                  25

<210> SEQ ID NO 26
<211> LENGTH: 24
<212> TYPE: PRT
<213> ORGANISM: Homo sapiens

<400> SEQUENCE: 26
```

```
Asn Pro Leu Leu Tyr Thr Ser Phe Asn Glu Asp Phe Lys Leu Ala Phe
  1               5                  10                  15
Lys Lys Leu Ile Arg Cys Arg Glu
             20

<210> SEQ ID NO 27
<211> LENGTH: 37
<212> TYPE: PRT
<213> ORGANISM: Homo sapiens

<400> SEQUENCE: 27

Asn Pro Ile Ile Tyr Cys Leu Arg Asn Gln Glu Val Lys Arg Ala Leu
  1               5                  10                  15
Cys Cys Ile Leu His Leu Tyr Gln His Gln Asp Pro Asp Pro Lys Lys
             20                  25                  30
Gly Ser Arg Asn Val
             35

<210> SEQ ID NO 28
<211> LENGTH: 27
<212> TYPE: PRT
<213> ORGANISM: Homo sapiens

<400> SEQUENCE: 28

Asn Pro Leu Ile Tyr Thr Leu Arg Asn Met Glu Val Lys Gly Ala Leu
  1               5                  10                  15
Arg Arg Leu Leu Gly Lys Gly Arg Glu Val Gly
             20                  25

<210> SEQ ID NO 29
<211> LENGTH: 62
<212> TYPE: PRT
<213> ORGANISM: Homo sapiens

<400> SEQUENCE: 29

Asn Pro Leu Phe Tyr Gly Phe Leu Gly Lys Lys Phe Lys Arg Tyr Phe
  1               5                  10                  15
Leu Gln Leu Leu Lys Tyr Ile Pro Pro Lys Ala Lys Ser His Ser Asn
             20                  25                  30
Leu Ser Thr Lys Met Ser Thr Leu Ser Tyr Arg Pro Ser Asp Asn Val
             35                  40                  45
Ser Ser Ser Thr Lys Lys Pro Ala Pro Cys Phe Glu Val Glu
             50                  55                  60

<210> SEQ ID NO 30
<211> LENGTH: 50
<212> TYPE: PRT
<213> ORGANISM: Homo sapiens

<400> SEQUENCE: 30

Asn Pro Phe Leu Tyr Cys Phe Val Gly Asn Arg Phe Gln Gln Lys Leu
  1               5                  10                  15
Arg Ser Val Phe Arg Val Pro Ile Thr Trp Leu Gln Gly Lys Arg Glu
             20                  25                  30
Ser Met Ser Cys Arg Lys Ser Ser Leu Arg Glu Met Glu Thr Phe
             35                  40                  45
Val Ser
     50
```

```
<210> SEQ ID NO 31
<211> LENGTH: 51
<212> TYPE: PRT
<213> ORGANISM: Homo sapiens

<400> SEQUENCE: 31

Asn Pro Leu Ile Tyr Ala Phe Ile Gly Gln Lys Phe Arg His Gly Leu
1               5                   10                  15

Leu Lys Ile Leu Ala Ile His Gly Leu Ile Ser Lys Asp Ser Leu Pro
            20                  25                  30

Lys Asp Ser Arg Pro Ser Phe Val Gly Ser Ser Gly His Thr Ser
        35                  40                  45

Thr Thr Leu
    50

<210> SEQ ID NO 32
<211> LENGTH: 67
<212> TYPE: PRT
<213> ORGANISM: Homo sapiens

<400> SEQUENCE: 32

Asn Pro Leu Ile Tyr Ala Phe Ala Gly Glu Lys Phe Arg Arg Tyr Leu
1               5                   10                  15

Tyr His Leu Tyr Gly Lys Cys Leu Ala Val Leu Cys Gly Arg Ser Val
            20                  25                  30

His Val Asp Phe Ser Ser Ser Glu Ser Gln Arg Ser Arg His Gly Ser
        35                  40                  45

Val Leu Ser Ser Asn Phe Thr Tyr His Thr Ser Asp Gly Asp Ala Leu
    50                  55                  60

Leu Leu Leu
65

<210> SEQ ID NO 33
<211> LENGTH: 59
<212> TYPE: PRT
<213> ORGANISM: Homo sapiens

<400> SEQUENCE: 33

Asn Pro Ile Leu Tyr Asn Leu Val Ser Ala Asn Phe Arg His Ile Phe
1               5                   10                  15

Leu Ala Thr Leu Ala Cys Leu Cys Pro Val Trp Arg Arg Arg Arg Lys
            20                  25                  30

Arg Pro Ala Phe Ser Arg Lys Ala Asp Ser Val Ser Ser Asn His Thr
        35                  40                  45

Leu Ser Ser Asn Ala Thr Arg Glu Thr Leu Tyr
    50                  55

<210> SEQ ID NO 34
<211> LENGTH: 107
<212> TYPE: PRT
<213> ORGANISM: Homo sapiens

<400> SEQUENCE: 34

Asn Pro Ile Ile Tyr Cys Cys Leu Asn Asp Arg Phe Arg Leu Gly Phe
1               5                   10                  15

Lys His Ala Phe Arg Cys Cys Pro Phe Ile Ser Ala Gly Asp Tyr Glu
            20                  25                  30

Gly Leu Glu Met Lys Ser Thr Arg Tyr Leu Gln Thr Gln Gly Ser Val
        35                  40                  45
```

```
Tyr Lys Val Ser Arg Leu Glu Thr Thr Ile Ser Thr Val Val Gly Ala
    50                  55                  60

His Glu Glu Pro Glu Asp Gly Pro Lys Ala Thr Pro Ser Ser Leu
 65              70                  75                  80

Asp Leu Thr Ser Asn Cys Ser Ser Arg Ser Asp Ser Lys Thr Met Thr
                85                  90                  95

Glu Ser Phe Ser Phe Ser Ser Asn Val Leu Ser
           100                 105

<210> SEQ ID NO 35
<211> LENGTH: 51
<212> TYPE: PRT
<213> ORGANISM: Homo sapiens

<400> SEQUENCE: 35

Asn Pro Trp Ile Tyr Ala Ser Phe Ser Ser Val Ser Ser Glu Leu
 1               5                  10                  15

Arg Ser Leu Leu Cys Cys Ala Arg Gly Arg Thr Pro Pro Ser Leu Gly
                20                  25                  30

Pro Gln Asp Glu Ser Cys Thr Thr Ala Ser Ser Ser Leu Ala Lys Asp
            35                  40                  45

Thr Ser Ser
    50

<210> SEQ ID NO 36
<211> LENGTH: 83
<212> TYPE: PRT
<213> ORGANISM: Homo sapiens

<400> SEQUENCE: 36

Asn Pro Val Ile Tyr Asn Leu Met Ser Gln Lys Phe Arg Ala Ala Phe
 1               5                  10                  15

Arg Lys Leu Cys Asn Cys Lys Gln Lys Pro Thr Glu Lys Pro Ala Asn
                20                  25                  30

Tyr Ser Val Ala Leu Asn Tyr Ser Val Ile Lys Glu Ser Asp His Phe
            35                  40                  45

Ser Thr Glu Leu Asp Asp Ile Thr Val Thr Asp Thr Tyr Leu Ser Ala
    50                  55                  60

Thr Lys Val Ser Phe Asp Asp Thr Cys Leu Ala Ser Glu Val Ser Phe
 65                  70                  75                  80

Ser Gln Ser

<210> SEQ ID NO 37
<211> LENGTH: 65
<212> TYPE: PRT
<213> ORGANISM: Homo sapiens

<400> SEQUENCE: 37

Asn Pro Trp Ile Tyr Met Leu Phe Thr Gly His Leu Phe His Glu Leu
 1               5                  10                  15

Val Gln Arg Phe Leu Cys Cys Ser Ala Ser Tyr Leu Lys Gly Arg Arg
                20                  25                  30

Leu Gly Glu Thr Ser Ala Ser Lys Lys Ser Asn Ser Ser Ser Phe Val
            35                  40                  45

Leu Ser His Arg Ser Ser Ser Gly Arg Ser Cys Ser Gln Pro Ser Thr
    50                  55                  60

Ala
 65
```

<210> SEQ ID NO 38
<211> LENGTH: 74
<212> TYPE: PRT
<213> ORGANISM: Homo sapiens

<400> SEQUENCE: 38

Asn Pro Val Leu Tyr Ser Leu Met Ser Ser Arg Phe Glu Thr Phe Gln
1               5                   10                  15

Glu Ala Leu Cys Leu Gly Ala Cys Cys His Arg Leu Arg Pro Arg His
            20                  25                  30

Ser Ser His Ser Leu Ser Arg Met Thr Thr Gly Ser Thr Leu Cys Asp
        35                  40                  45

Val Gly Ser Leu Gly Ser Trp Val His Pro Leu Ala Gly Asn Asp Gly
    50                  55                  60

Pro Glu Ala Gln Gln Glu Thr Asp Pro Ser
65                  70

<210> SEQ ID NO 39
<211> LENGTH: 62
<212> TYPE: PRT
<213> ORGANISM: Homo sapiens

<400> SEQUENCE: 39

Asn Pro Leu Val Tyr Cys Phe Met His Arg Arg Phe Arg Gln Ala Cys
1               5                   10                  15

Leu Glu Thr Cys Ala Arg Cys Cys Pro Arg Pro Arg Ala Arg Pro
            20                  25                  30

Arg Ala Leu Pro Asp Glu Asp Pro Pro Thr Pro Ser Ile Ala Ser Leu
            35                  40                  45

Ser Arg Leu Ser Tyr Thr Thr Ile Ser Thr Leu Gly Pro Gly
        50                  55                  60

<210> SEQ ID NO 40
<211> LENGTH: 82
<212> TYPE: PRT
<213> ORGANISM: Homo sapiens

<400> SEQUENCE: 40

Asn Pro Leu Val Tyr Ala Leu Ala Ser Arg His Phe Arg Ala Arg Phe
1               5                   10                  15

Arg Arg Leu Trp Pro Cys Gly Arg Arg Arg His Arg Ala Arg Arg
            20                  25                  30

Ala Leu Arg Arg Val Arg Pro Ala Ser Ser Gly Pro Pro Gly Cys Pro
        35                  40                  45

Gly Asp Ala Arg Pro Ser Gly Arg Leu Leu Ala Gly Gly Gln Gly
    50                  55                  60

Pro Glu Pro Arg Glu Gly Pro Val His Gly Gly Glu Ala Ala Arg Gly
65                  70                  75                  80

Pro Glu

<210> SEQ ID NO 41
<211> LENGTH: 76
<212> TYPE: PRT
<213> ORGANISM: Homo sapiens

<400> SEQUENCE: 41

Asn Pro Ile Ile Tyr Thr Leu Thr Asn Lys Glu Met Arg Arg Ala Phe
1               5                   10                  15

```
Ile Arg Ile Met Ser Cys Cys Lys Cys Pro Ser Gly Asp Ser Ala Gly
            20                  25                  30

Lys Phe Lys Arg Pro Ile Ile Ala Gly Met Glu Phe Ser Arg Ser Lys
            35                  40                  45

Ser Asp Asn Ser Ser His Pro Gln Lys Asp Glu Gly Asp Asn Pro Glu
 50                  55                  60

Thr Ile Met Ser Ser Gly Asn Val Asn Ser Ser Ser
 65                  70                  75
```

<210> SEQ ID NO 42
<211> LENGTH: 80
<212> TYPE: PRT
<213> ORGANISM: Homo sapiens

<400> SEQUENCE: 42

```
Asn Pro Ile Ile Tyr Ala Leu Arg Ser Lys Asp Leu Arg His Ala Phe
 1               5                  10                  15

Arg Ser Met Phe Pro Ser Cys Glu Gly Thr Ala Gln Pro Leu Asp Asn
            20                  25                  30

Ser Met Gly Asp Ser Asp Cys Leu His Lys His Ala Asn Asn Ala Ala
            35                  40                  45

Ser Val His Arg Ala Ala Glu Ser Cys Ile Lys Ser Thr Val Lys Ile
 50                  55                  60

Ala Lys Val Thr Met Ser Val Ser Thr Asp Thr Ser Ala Glu Ala Leu
 65                  70                  75                  80
```

<210> SEQ ID NO 43
<211> LENGTH: 59
<212> TYPE: PRT
<213> ORGANISM: Homo sapiens

<400> SEQUENCE: 43

```
Asn Pro Val Leu Tyr Ala Phe Leu Asp Glu Asn Phe Lys Arg Cys Phe
 1               5                  10                  15

Arg Gly Leu Cys Arg Lys Pro Cys Gly Arg Pro Asp Pro Ser Ser Phe
            20                  25                  30

Ser Arg Pro Arg Glu Ala Thr Ala Arg Glu Arg Val Thr Ala Cys Thr
            35                  40                  45

Pro Ser Asp Gly Pro Gly Gly Gly Arg Ala Ala
 50                  55
```

<210> SEQ ID NO 44
<211> LENGTH: 58
<212> TYPE: PRT
<213> ORGANISM: Homo sapiens

<400> SEQUENCE: 44

```
Asp Pro Phe Val Tyr Tyr Phe Val Ser His Asp Phe Arg Asp His Ala
 1               5                  10                  15

Lys Asn Ala Leu Leu Cys Arg Ser Val Arg Thr Val Lys Gln Met Gln
            20                  25                  30

Val Ser Leu Thr Ser Lys Lys His Ser Arg Lys Ser Ser Ser Tyr Ser
            35                  40                  45

Ser Ser Ser Thr Thr Val Lys Thr Ser Tyr
 50                  55
```

<210> SEQ ID NO 45
<211> LENGTH: 66

```
<212> TYPE: PRT
<213> ORGANISM: Rattus norvegicus

<400> SEQUENCE: 45

Asn Gly Glu Val Gln Ala Glu Leu Arg Arg Lys Trp Arg Arg Trp His
1               5                   10                  15

Leu Gln Gly Val Leu Gly Trp Ser Ser Lys Ser Gln His Pro Trp Gly
            20                  25                  30

Gly Ser Asn Gly Ala Thr Cys Ser Thr Gln Val Ser Met Leu Thr Arg
            35                  40                  45

Val Ser Pro Ser Ala Arg Arg Ser Ser Ser Phe Gln Ala Glu Val Ser
        50                  55                  60

Leu Val
65
```